US012485123B2

(12) United States Patent
Zhang et al.

(10) Patent No.: US 12,485,123 B2
(45) Date of Patent: Dec. 2, 2025

(54) **1*H*-PYRAZOLO[4,3-*d*]PYRIMIDINE COMPOUNDS AS TOLL-LIKE RECEPTOR 7 (TLR7) AGONISTS**

(71) Applicant: BRISTOL-MYERS SQUIBB COMPANY, Princeton, NJ (US)

(72) Inventors: Qian Zhang, Danville, CA (US); Sanjeev Gangwar, Foster City, CA (US); Ashvinikumar V. Gavai, Princeton Junction, NJ (US); Qiang Cong, Palo Alto, CA (US); Yam B. Poudel, Fremont, CA (US); Liqi He, San Jose, CA (US); Prasanna Sivaprakasam, Plainsboro, NJ (US); Christine M. Tarby, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 711 days.

(21) Appl. No.: 17/792,878

(22) PCT Filed: Jan. 26, 2021

(86) PCT No.: PCT/US2021/014979
§ 371 (c)(1),
(2) Date: Jul. 14, 2022

(87) PCT Pub. No.: WO2021/154665
PCT Pub. Date: Aug. 5, 2021

(65) Prior Publication Data

US 2023/0130516 A1 Apr. 27, 2023

Related U.S. Application Data

(60) Provisional application No. 63/057,661, filed on Jul. 28, 2020, provisional application No. 62/966,092, filed on Jan. 27, 2020.

(51) Int. Cl.

| | |
|---|---|
| ***A61K 31/519*** | (2006.01) |
| ***A61K 31/5377*** | (2006.01) |
| ***A61K 39/395*** | (2006.01) |
| ***C07D 487/04*** | (2006.01) |
| ***C07D 519/00*** | (2006.01) |

(52) U.S. Cl.
CPC ........ *A61K 31/519* (2013.01); *A61K 31/5377* (2013.01); *A61K 39/3955* (2013.01); *C07D 487/04* (2013.01); *C07D 519/00* (2013.01)

(58) Field of Classification Search
CPC ................ C07D 519/00; C07D 487/04; A61K 39/3955; A61K 31/5377; A61K 31/519
See application file for complete search history.

(56) References Cited

U.S. PATENT DOCUMENTS

| | | | |
|---|---|---|---|
| 6,028,076 | A | 2/2000 | Hirota et al. |
| 6,376,501 | B1 | 4/2002 | Isobe et al. |
| 7,241,890 | B2 | 7/2007 | Kasibhatla et al. |
| 7,521,454 | B2 | 4/2009 | Isobe et al. |
| 7,642,350 | B2 | 1/2010 | Pryde |
| 7,691,877 | B2 | 4/2010 | Jones et al. |
| 7,919,498 | B2 | 4/2011 | Chen et al. |
| 8,148,371 | B2 | 4/2012 | Isobe et al. |
| 8,729,088 | B2 | 5/2014 | Carson et al. |
| 8,993,755 | B2 | 3/2015 | Graupe et al. |
| 9,050,376 | B2 | 6/2015 | Carson et al. |
| 9,127,006 | B2 | 9/2015 | Desai et al. |
| 9,161,934 | B2 | 10/2015 | Halcomb et al. |
| 9,173,935 | B2 | 11/2015 | Maj et al. |
| 9,295,732 | B2 | 3/2016 | Lioux et al. |
| 9,499,549 | B2 | 11/2016 | McGowan et al. |
| 9,662,336 | B2 | 5/2017 | Coe et al. |
| 9,902,730 | B2 | 2/2018 | Li et al. |
| 9,944,649 | B2 | 4/2018 | Cortez et al. |
| 10,457,681 | B2 | 10/2019 | Young et al. |
| 10,472,361 | B2 | 11/2019 | Poudel et al. |

(Continued)

FOREIGN PATENT DOCUMENTS

| | | | |
|---|---|---|---|
| EP | 3546457 | A1 | 10/2019 |
| JP | 2004137157 | A | 5/2004 |

(Continued)

OTHER PUBLICATIONS

Akinbobuyi et al.; "Synthesis of Functionalize Dpurine Analogs for Antibody Conjugation"; 2015 Joint Southwestern Regional Meeting 392; 2015.
Akinbobuyi et al.; "Synthesis and immunostimulatory activity of substituted TLR7 agonists"; Bioorganic & Medicinal Chemistry Letters; 26; 4246-4249; 2016.
Beesu et al.; "Identification of High-Potency Human TLR8 and Dual TLR7/TLR8 Agonists in Pyrimidine-2,4-diamines"; J Med Chem; 60; 2084-2098; 2017.
Berghofer et al.; "Natural and Synthetic TLR7 Ligands Inhibit CpG-A- and CpG-C-Oligodeoxynucleotide- Induced IFN α-Production"; The Journal of Immunology; 178; 4072-4079; 2007.

(Continued)

*Primary Examiner* — Renee Claytor
*Assistant Examiner* — Christopher Lindsay Johnson
(74) *Attorney, Agent, or Firm* — Joseph F. Reidy

(57) ABSTRACT

Compounds according to formula I are useful as agonists of Toll-like receptor 7 (TLR7). Such compounds can be used in cancer treatment, especially in combination with an anti-cancer immunotherapy agent, or as a vaccine adjuvant.

(I)

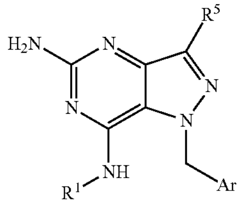

10 Claims, No Drawings

(56) References Cited

U.S. PATENT DOCUMENTS

| | | | |
|---|---|---|---|
| 10,487,084 | B2 | 11/2019 | He et al. |
| 10,494,370 | B2 | 12/2019 | Poudel et al. |
| 10,508,115 | B2 | 12/2019 | He et al. |
| 2007/0225303 | A1 | 9/2007 | Ogita et al. |
| 2009/0105212 | A1 | 4/2009 | Isobe et al. |
| 2009/0118263 | A1 | 5/2009 | Hashimoto et al. |
| 2011/0028715 | A1 | 2/2011 | Isobe et al. |
| 2012/0003298 | A1 | 1/2012 | Barberis et al. |
| 2012/0083473 | A1 | 4/2012 | Holldack et al. |
| 2012/0231023 | A1 | 9/2012 | Zurawski et al. |
| 2012/0302598 | A1 | 11/2012 | Jones et al. |
| 2013/0202629 | A1 | 8/2013 | Carson et al. |
| 2014/0141033 | A1 | 5/2014 | Vernejoul et al. |
| 2014/0323441 | A1 | 10/2014 | Bonfanti et al. |
| 2015/0299221 | A1 | 10/2015 | Bonfanti et al. |
| 2016/0168150 | A1 | 6/2016 | McGowan et al. |
| 2016/0199499 | A1 | 7/2016 | Carson et al. |
| 2016/0304531 | A1 | 10/2016 | Bonfanti et al. |
| 2017/0121421 | A1 | 5/2017 | Cortez et al. |
| 2017/0273983 | A1 | 9/2017 | Ding et al. |
| 2020/0038403 | A1 | 2/2020 | Poudel et al. |
| 2020/0039986 | A1 | 2/2020 | Poudel et al. |

FOREIGN PATENT DOCUMENTS

| | | | |
|---|---|---|---|
| WO | 2007028129 | A1 | 3/2007 |
| WO | 2015036044 | A1 | 3/2015 |
| WO | 2016107536 | A1 | 7/2016 |
| WO | 2017076346 | A1 | 5/2017 |
| WO | 2017216293 | A1 | 12/2017 |
| WO | 2018095426 | A1 | 5/2018 |
| WO | 2019124500 | A1 | 6/2019 |
| WO | 2019209811 | A1 | 10/2019 |
| WO | 2020028608 | A1 | 2/2020 |

OTHER PUBLICATIONS

Chan et al.; "Synthesis and Characterization of PEGylated Toll Like Receptor 7 Ligands"; Bioconugate Chemistry; 22; 445-454; 2011.

Chan et al.; "Synthesis and Immunological Characterization of Toll-Like Receptor 7 Agonistic Conjugates"; Bioconjugate Chemistry; vol. 20; 1194-1200; 2009.

Cortez et al.; "Recent advances in Small-Molecule TLR7 Agonists for Drug Discovery"; Medicinal Chemistry Reviews; 481-502; 2018.

Embrechts et al.; "2,4-Diaminoquinazolines as Dual Toll-like Receptor (TLR) 7/8 Modulators for the Treatment of Hepatitis B Virus"; Journal of Medicinal Chemistry; 61; 6236-6246; 2018.

Gadd et al.; "Targeted Activation of Toll-Like Receptors: Conjugation of a Toll-Like Receptor 7 Agonist to a Monoclonal Antibody Maintains Antigen Binding and Specificity"; Bioconjugate Chemistry; 26; 1743-1752; 2015.

International Search Authority; International Search Report and Written Opinion; WIPO; 11 Pages; Apr. 1, 2021.

Isobe et al.; "Synthesis and Biological Evaluation of Novel 9-Substituted-8-Hydroxyadenine Derivatives as Potent Interferon Inducers"; J Med Chem; 49; 2088-2095; 2006.

Koga-Yamakawa et al.; "Intratracheal and Oral Administration of SM-276001: A Selective TLR7 Agonist, Leads to Antitumor Efficacy in Primary and Metastatic Models of Cancer"; IJC Cancer; 132; 580-590; 2013.

Lund et al.; "Recognition of Single-Stranded RNA Viruses by Toll-like receptor 7"; Proc Nat'l Acad. Sci; 101:15; 5598-5603; 2004.

McGowan et al.; "Identification and Optimization of Pyrrolo[3,2-d]pyrimidine Toll-like Receptor 7 (TLR7) Selective Agonists for the Treatment of Hepatitis B"; J Med Chem; 60; 6137-6151; 2017.

Musmuca et al.; "Small-Molecule Interferon Inducers. Toward the Comprehension of the Molecular Determinants through Ligand-Based Approaches"; J Chem Inform Model; 49; 1777-1786; 2009.

Nakamura et al.; "Synthesis and Evaluation of 8-oxoadenine Derivatives as Potent Toll-like Receptor 7 Agonists with High Water Solubility"; Bioorganic Medical Chemistry Letters; 23; 669-672; 2013.

Sato-Kaneko et al.; "Combination Immunotherapy with TLR Agonists and Checkpoint Inhibitors Suppresses Head and Neck Cancer"; JCI Insight; 2:18; 93397; 2017.

Smitts et al.; "The Use of TLR7 and TLR8 Ligands for the Enhancement of Cancer Immunotherapy"; The Oncologist; 13; 859-875; 2008.

Vakslakos et al.; "The Use of Toll-like Receptor 7/8 Agonists as Vaccine Adjuvants"; Expert Review of Vaccines; 12;7; 809-819; 2013.

Yoshiaki; JP2004137157 abstract; 2004.

Yu et al.; "Toll-Like Receptor 7 Agonists: Chemical Feature Based Pharmacophore Identification and Molecular Docking Studies"; Plossone; 1-12; 2013.

Zhang et al.; "Structural Analysis Reveals that Toll-like Receptor 7 Is a Dual Receptor for Guanosine and Single-Stranded RNA"; Immunity; 45; 737-748; 2016.

1*H*-PYRAZOLO[4,3-*d*]PYRIMIDINE COMPOUNDS AS TOLL-LIKE RECEPTOR 7 (TLR7) AGONISTS

CROSS-REFERENCE TO RELATED APPLICATIONS

This application claims the benefit under 35 U.S.C. § 119(e) of U.S. Provisional Application Ser. No. 63/057,661, filed Jul. 28, 2020, and U.S. Provisional Application Ser. No. 62/966,092, filed Jan. 27, 2020; the disclosures of which are incorporated herein by reference.

BACKGROUND OF THE DISCLOSURE

This disclosure relates to Toll-like receptor 7 ("TLR7") agonists and conjugates thereof, and methods for the preparation and use of such agonists and their conjugates.

Toll-like receptors ("TLRs") are receptors that recognize pathogen-associated molecular patterns ("PAMPs"), which are small molecular motifs conserved in certain classes of pathogens. TLRs can be located either on a cell's surface or intracellularly. Activation of a TLR by the binding of its cognate PAMP signals the presence of the associated pathogen inside the host—i.e., an infection—and stimulates the host's immune system to fight the infection. Humans have 10 TLRs, named TLR1, TLR2, TLR3, and so on.

The activation of a TLR—with TLR7 being the most studied—by an agonist can have a positive effect on the action of vaccines and immunotherapy agents in treating a variety of conditions other than actual pathogen infection, by stimulating the immune response overall. Thus, there is considerable interest in the use of TLR7 agonists as vaccine adjuvants or as enhancers in cancer immunotherapy. See, for example, Vasilakos and Tomai 2013, Sato-Kaneko et al. 2017, Smits et al. 2008, and Ota et al. 2019.

TLR7, an intracellular receptor located on the membrane of endosomes, recognizes PAMPs associated with single-stranded RNA viruses. Its activation induces secretion of Type I interferons such as IFNα and IFNβ (Lund et al. 2004). TLR7 has two binding sites, one for single stranded RNA ligands (Berghöfer et al. 2007) and one for small molecules such as guanosine (Zhang et al. 2016).

TLR7 can bind to, and be activated by, guanosine-like synthetic agonists such as imiquimod, resiquimod, and gardiquimod, which are based on a 1H-imidazo[4,5-c]quinoline scaffold. For a review of small-molecule TLR7 agonists, see Cortez and Va 2018.

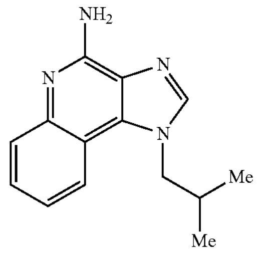

Imiquimod

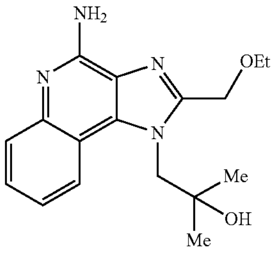

Resiquimod

-continued

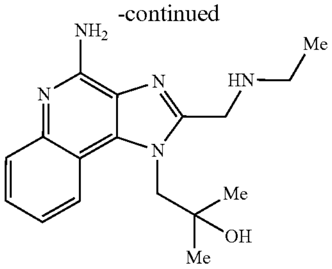

Gardiquimod

Synthetic TLR7 agonists based on a pteridinone molecular scaffold are also known, as exemplified by vesatolimod (Desai et al. 2015).

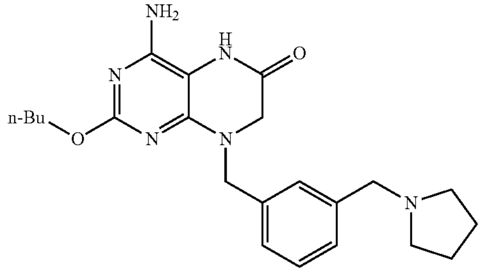

Vesatolimod

Other synthetic TLR7 agonists based on a purine-like scaffold have been disclosed, frequently according to the general formula (A):

(A)

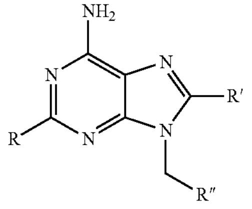

where R, R', and R" are structural variables, with R" typically containing an unsubstituted or substituted aromatic or heteroaromatic ring.

Disclosures of bioactive molecules having a purine-like scaffold and their uses in treating conditions such as fibrosis, inflammatory disorders, cancer, or pathogenic infections include: Akinbobuyi et al. 2015 and 2016; Barberis et al. 2012; Carson et al. 2014; Ding et al. 2016, 2017a, and 2017b; Graupe et al. 2015; Hashimoto et al. 2009; He et al. 2019a and 2019b; Holldack et al. 2012; Isobe et al. 2009a and 2012; Poudel et al. 2019a and 2019b; Pryde 2010; and Young et al. 2019.

The group R" can be pyridyl: Bonfanti et al. 2015a and 2015b; Halcomb et al. 2015; Hirota et al. 2000; Isobe et al. 2002, 2004, 2006, 2009a, 2009b, 2011, and 2012; Kasibhatla et al. 2007; Koga-Yamakawa et al. 2013; Musmuca et al. 2009; Nakamura 2012; Ogita et al. 2007; and Yu et al. 2013.

There are disclosures of related molecules in which the 6,5-fused ring system of formula (A)—a pyrimidine six member ring fused to an imidazole five member ring—is modified. (a) Dellaria et al. 2007, Jones et al. 2010 and 2012, and Pilatte et al. 2017 disclose compounds in which the pyrimidine ring is replaced by a pyridine ring. (b) Chen et al. 2011, Coe et al. 2017, Poudel et al. 2020a and 2020b, and Zhang et al. 2018 disclose compounds in which the imidazole ring is replaced by a pyrazole ring. (c) Cortez et al. 2017 and 2018; Li et al. 2018; and McGowan et al. 2016a, 2016b, and 2017 disclose compounds in which the imidazole ring is replaced by a pyrrole ring.

Bonfanti et al. 2015b and 2016 and Purandare et al. 2019 disclose TLR7 modulators in which the two rings of a purine moiety are spanned by a macrocycle:

A TLR7 agonist can be conjugated to a partner molecule, which can be, for example, a phospholipid, a poly(ethylene glycol) ("PEG"), an antibody, or another TLR (commonly TLR2). Exemplary disclosures include: Carson et al. 2013, 2015, and 2016, Chan et al. 2009 and 2011, Cortez et al. 2017, Gadd et al. 2015, Lioux et al. 2016, Maj et al. 2015, Vernejoul et al. 2014, and Zurawski et al. 2012. A frequent conjugation site is at the R" group of formula (A).

Jensen et al. 2015 discloses the use of cationic lipid vehicles for the delivery of TLR7 agonists.

Some TLR7 agonists, including resiquimod are dual TLR7/TLR8 agonists. See, for example, Beesu et al. 2017, Embrechts et al. 2018, Lioux et al. 2016, and Vernejoul et al. 2014.

Full citations for the documents cited herein by first author or inventor and year are listed at the end of this specification.

BRIEF SUMMARy OF THE DISCLOSURE

This specification relates to compounds having a 1H-pyrazolo[4,3d]pyrimidine aromatic system, having activity as TLR7 agonists.

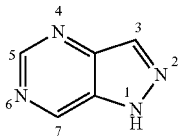

1H-pyrazolo[4,3-d] pyridimidine

In one aspect, there is provided a compound with a structure according to formula I (I)

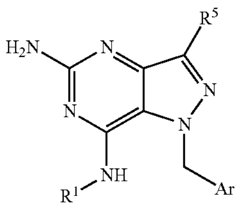

wherein

Ar is

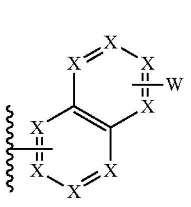

or

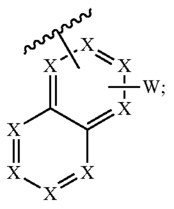

W is H, halo, $C_1$-$C_3$ alkyl, CN, ($C_1$-$C_4$ alkanediyl)OH,

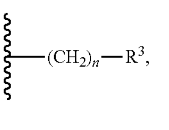

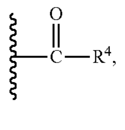

or

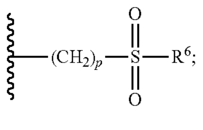

each X is independently N or $CR^2$;

$R^1$ is ($C_1$-$C_5$ alkyl),
($C_2$-$C_5$ alkenyl),
($C_1$-$C_8$ alkanediyl)$_{0-1}$($C_3$-$C_6$ cycloalkyl),
($C_1$-$C_8$ alkanediyl)$_{0-1}$($C_5$-$C_{10}$ spiroalkyl),
($C_2$-$C_8$ alkanediyl)OH,
($C_2$-$C_8$ alkanediyl)O($C_1$-$C_3$ alkyl),
($C_1$-$C_4$ alkanediyl)$_{0-1}$(5-6 membered heteroaryl),
($C_1$-$C_4$ alkanediyl)$_{0-1}$phenyl,
($C_1$-$C_4$ alkanediyl)$CF_3$,
($C_2$-$C_8$ alkanediyl)N[C(=O)]($C_1$-$C_3$ alkyl),
or
($C_2$-$C_8$ alkanediyl)$NR^xR^y$;

each $R^2$ is independently H, O($C_1$-$C_3$ alkyl), S($C_1$-$C_3$ alkyl), $SO_2$($C_1$-$C_3$ alkyl), $C_1$-$C_3$ alkyl, O($C_3$-$C_4$ cycloalkyl), S($C_3$-$C_4$ cycloalkyl), $SO_2$($C_3$-$C_4$ cycloalkyl), $C_3$-$C_4$ cycloalkyl, Cl, F, CN, or $[C(=O)]_{0-1}NR^xR^y$;

$R^3$ is H, halo, OH, CN,
$NH_2$,
$NH[C(=O)]_{0-1}$($C_1$-$C_5$ alkyl),
N($C_1$-$C_5$ alkyl)$_2$,
$NH[C(=O)]_{0-1}$($C_1$-$C_4$ alkanediyl)$_{0-1}$($C_3$-$C_5$ cycloalkyl),
$NH[C(=O)]_{0-1}$($C_1$-$C_4$ alkanediyl)$_{0-1}$($C_4$-$C_{10}$ bicycloalkyl),
$NH[C(=O)]_{0-1}$($C_1$-$C_4$ alkanediyl)$_{0-1}$($C_5$-$C_{10}$ spiroalkyl),
N($C_3$-$C_6$ cycloalkyl)$_2$,
O($C_1$-$C_4$ alkanediyl)$_{0-1}$($C_3$-$C_5$ cycloalkyl),
O($C_1$-$C_4$ alkanediyl)$_{0-1}$($C_4$-$C_5$ bicycloalkyl),
O($C_1$-$C_4$ alkanediyl)$_{0-1}$($C_5$-$C_{10}$ spiroalkyl),
O($C_1$-$C_4$ alkanediyl)$_{0-1}$($C_1$-$C_6$ alkyl),
N[$C_1$-$C_3$ alkyl]C(=O)($C_1$-$C_6$ alkyl),
NH($SO_2$)($C_1$-$C_5$ alkyl),
NH($SO_2$)($C_1$-$C_4$ alkanediyl)$_{0-1}$($C_3$-$C_5$ cycloalkyl),
NH($SO_2$)($C_1$-$C_4$ alkanediyl)$_{0-1}$($C_4$-$C_{10}$ bicycloalkyl),
NH($SO_2$)($C_1$-$C_4$ alkanediyl)$_{0-1}$($C_5$-$C_{10}$ spiroalkyl),
a 6-membered aromatic or heteroaromatic moiety,
a 5-membered heteroaromatic moiety, or
a moiety having the structure

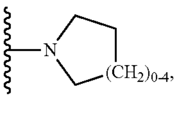

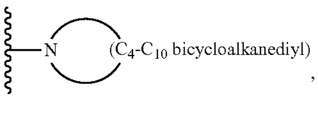

, or

-continued

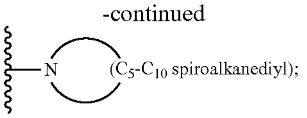

$R^4$ is $NH_2$,
$NH(C_1$-$C_5$ alkyl),
$N(C_1$-$C_5$ alkyl$)_2$,
$NH(C_1$-$C_4$ alkanediyl$)_{0\text{-}1}(C_3$-$C_5$ cycloalkyl),
$NH(C_1$-$C_4$ alkanediyl$)_{0\text{-}1}(C_4$-$C_{10}$ bicycloalkyl),
$NH(C_1$-$C_4$ alkanediyl$)_{0\text{-}1}(C_5$-$C_{10}$ spiroalkyl),
$N(C_3$-$C_6$ cycloalkyl$)_2$,
or
a moiety having the structure

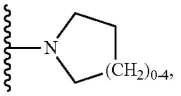 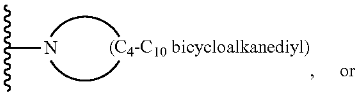 , or

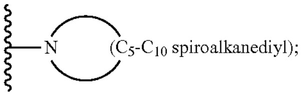

$R^5$ is H, $C_1$-$C_5$ alkyl, $C_2$-$C_5$ alkenyl, $C_3$-$C_6$ cycloalkyl, halo, $O(C_1$-$C_5$ alkyl), $(C_1$-$C_4$ alkanediyl)OH, $(C_1$-$C_4$ alkanediyl)$O(C_1$-$C_3$ alkyl), phenyl, $NH(C_1$-$C_5$ alkyl), 5 or 6 membered heteroaryl,

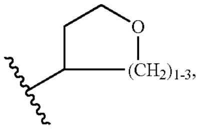 or 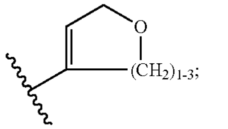

$R^6$ is $NH_2$,
$(NH)_{0\text{-}1}(C_1$-$C_5$ alkyl),
$N(C_1$-$C_5$ alkyl$)_2$,
$(NH)_{0\text{-}1}(C_1$-$C_4$ alkanediyl$)_{0\text{-}1}(C_3$-$C_5$ cycloalkyl),
$(NH)_{0\text{-}1}(C_1$-$C_4$ alkanediyl$)_{0\text{-}1}(C_4$-$C_{10}$ bicycloalkyl),
$(NH)_{0\text{-}1}(C_1$-$C_4$ alkanediyl$)_{0\text{-}1}(C_5$-$C_{10}$ spiroalkyl),
$N(C_3$-$C_6$ cycloalkyl$)_2$,
or
a moiety having the structure

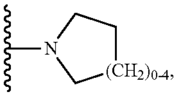 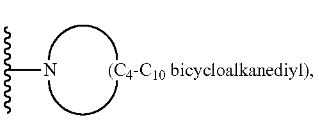 or

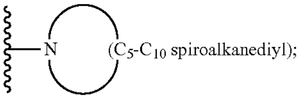

$R^x$ and $R^y$ are independently H or $C_1$-$C_3$ alkyl or $R^x$ and $R^y$ combine with the nitrogen to which they are bonded to form a 3- to 7-membered heterocycle;
n is 1, 2, or 3;
and
p is 0, 1, 2, or 3;
wherein in $R^1$, $R^2$, $R^3$, $R^4$, $R^5$, and $R^6$
an alkyl, cycloalkyl, alkanediyl, bicycloalkyl, spiroalkyl, cyclic amine, 6-membered aromatic or heteroaromatic moiety, 5-membered heteroaromatic moiety or a moiety of the formula

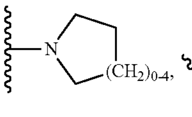 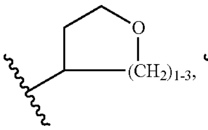 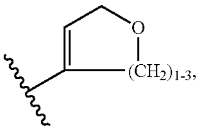

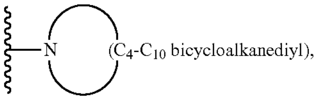 or

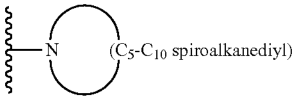

is optionally substituted with one or more substituents selected from OH, halo, CN, $(C_1$-$C_3$ alkyl), $O(C_1$-$C_3$ alkyl), $C(=O)(C_1$-$C_3$ alkyl), $SO_2(C_1$-$C_3$ alkyl), $NR^xR^y$, $(C_1$-$C_4$ alkanediyl)OH, $(C_1$-$C_4$ alkanediyl)$O(C_1$-$C_3$ alkyl);
and
an alkyl, alkanediyl, cycloalkyl, bicycloalkyl, spiroalkyl, or a moiety of the formula

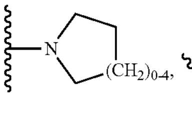 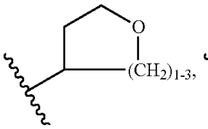 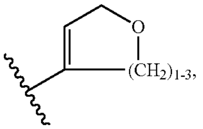

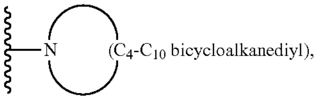 or

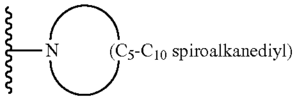

may have a $CH_2$ group replaced by O, $SO_2$, $CF_2$, $C(=O)$, NH,
$N[C(=O)]_{0\text{-}1}(C_1$-$C_3$ alkyl),
$N[C(=O)]_{0\text{-}1}(C_1$-$C_4$ alkanediyl$)_{0\text{-}1}CF_3$,
or
$N[C(=O)]_{0\text{-}1}(C_1$-$C_4$ alkanediyl$)_{0\text{-}1}(C_3$-$C_5$ cycloalkyl).

Compounds disclosed herein have activity as TLR7 agonists and some can be conjugated to an antibody for targeted delivery to a target tissue or organ of intended action. They can also be PEGylated, to modulate their pharmaceutical properties.

Compounds disclosed herein, or their conjugates or their PEGylated derivatives, can be used in the treatment of a subject suffering from a condition amenable to treatment by activation of the immune system, by administering to such subject a therapeutically effective amount of such a compound or a conjugate thereof or a PEGylated derivative thereof, especially in combination with a vaccine or a cancer immunotherapy agent.

DETAILED DESCRIPTION OF THE DISCLOSURE

Compounds

In one aspect, one X in the moiety Ar of formula (I) is N and the remaining ones are CH, with one CH having the H replaced by W.

In one aspect, W is

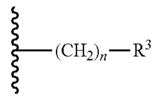

(preferably n equals 1) or

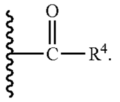

In one aspect, compounds of this disclosure are according to formula (Ia), wherein $R^1$, $R^5$, and W are as defined in respect of formula (I):

(Ia)

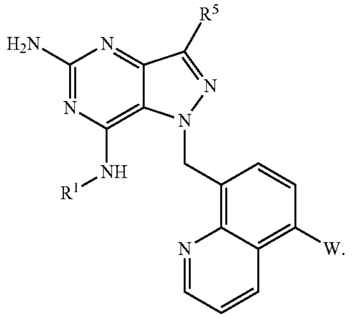

In another aspect, compounds of this disclosure are according to formula (Ib), wherein $R^1$, $R^3$, and $R^5$ are as defined in respect of formula (I):

(Ib)

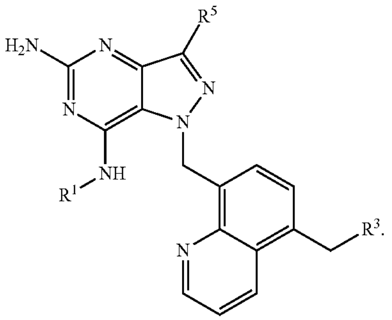

In one embodiment of compounds according to formula (Ib), $R^3$ is $NH(C_1\text{-}C_5\ alkyl)$, $N(C_1\text{-}C_5\ alkyl)_2$, $NH(C_1\text{-}C_4\ alkanediyl)_{0\text{-}1}(C_3\text{-}C_8\ cycloalkyl)$, $NH(C_1\text{-}C_4\ alkanediyl)_{0\text{-}1}(C_4\text{-}C_{10}\ bicycloalkyl)$, $NH(C_1\text{-}C_4\ alkanediyl)_{0\text{-}1}(C_5\text{-}C_{10}\ spiroalkyl)$, $N(C_3\text{-}C_6\ cycloalkyl)_2$, $N[C_1\text{-}C_3\ alkyl](C_1\text{-}C_6\ alkyl)$, or a moiety having the structure

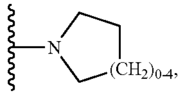

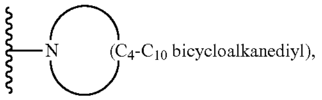

or

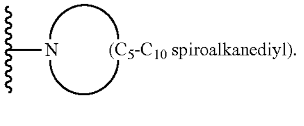

In another embodiment of compounds according to formula (Ib), $R^3$ is $NH[C(=O)](C_1\text{-}C_5\ alkyl)$, $NH[C(=O)](C_1\text{-}C_4\ alkanediyl)_{0\text{-}1}(C_3\text{-}C_5\ cycloalkyl)$, $NH[C(=O)](C_1\text{-}C_4\ alkanediyl)_{0\text{-}1}(C_4\text{-}C_{10}\ bicycloalkyl)$, $NH[C(=O)](C_1\text{-}C_4\ alkanediyl)_{0\text{-}1}(C_5\text{-}C_{10}\ spiroalkyl)$, or $N[C_1\text{-}C_3\ alkyl]C(=O)(C_1\text{-}C_6\ alkyl)$.

In another embodiment of compounds according to formula (Ib), $R^3$ is $O(C_1\text{-}C_4\ alkanediyl)_{0\text{-}1}(C_3\text{-}C_5\ cycloalkyl)$, $O(C_1\text{-}C_4\ alkanediyl)_{0\text{-}1}(C_4\text{-}C_5\ bicycloalkyl)$, $O(C_1\text{-}C_4\ alkanediyl)_{0\text{-}1}(C_5\text{-}C_{10}\ spiroalkyl)$, or $O(C_1\text{-}C_4\ alkanediyl)_{0\text{-}1}(C_1\text{-}C_6\ alkyl)$.

In another aspect, compounds of this disclosure are according to formula (Ic), wherein $R^1$, $R^4$ and $R^5$ are as defined in respect of formula (I):

(Ic)

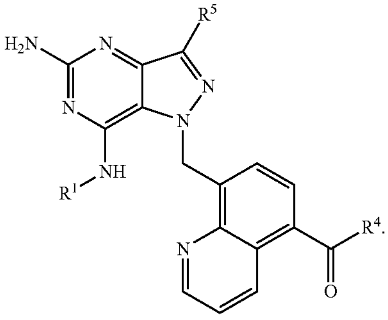

In one aspect, this disclosure provides a compound having a structure according to formula (Id)

(Id)

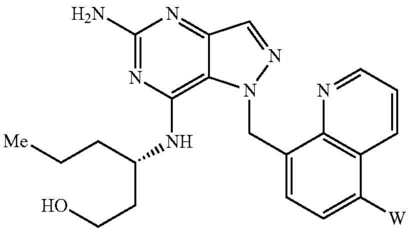

wherein W is

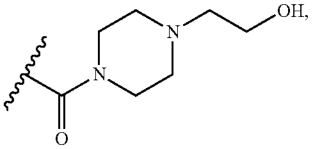

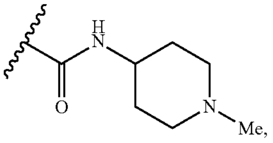

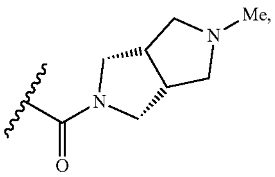

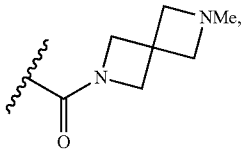 or 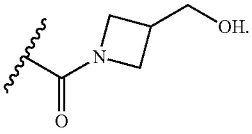

In one embodiment, where W is $$-(CH_2)_n-R^3,$$

n is 1, 2, or 3.

In another embodiment, compounds of this disclosure are according to formula (Ie)

(Ie)

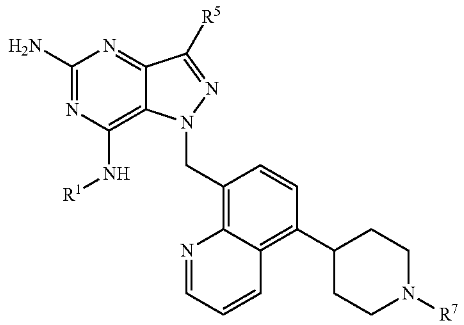

wherein $R^1$ is

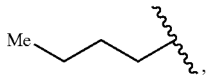, 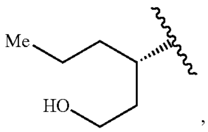,

-continued

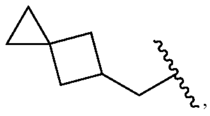, or 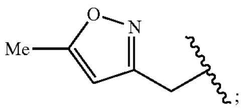;

$R^5$ is H or Me; and $R^7$ is H, $C_1$-$C_5$ alkyl, or $C_3$-$C_6$ cycloalkyl; wherein the cycloalkyl group optionally has a $CH_2$ group replaced by O, NH, or $N(C_1$-$C_3)$alkyl.

Examples of groups $R^1$ are

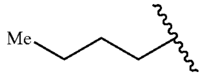, (n-Bu)

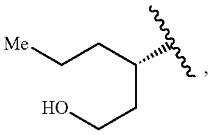,

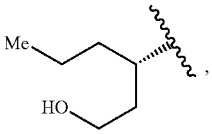, 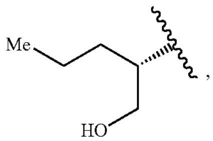,

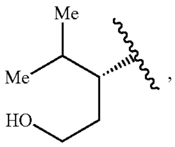, 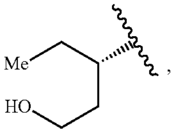,

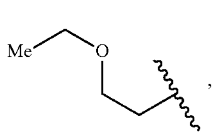, 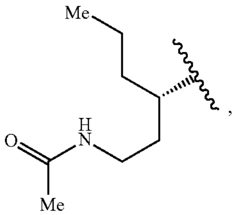,

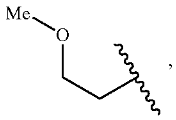, 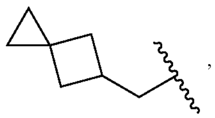,

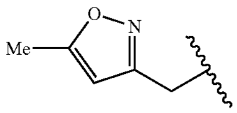, and 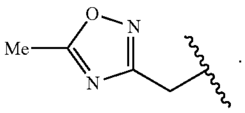.

Preferably, $R^1$ is selected from the following group ("preferred $R^1$ group"), consisting of:

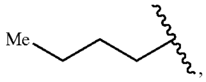, 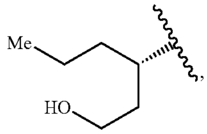,

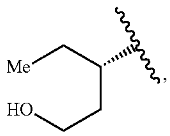, 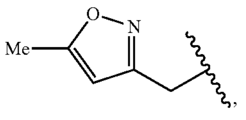, and

-continued
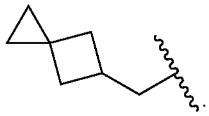
Examples of groups $R^3$ include
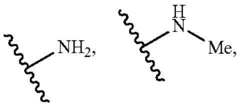
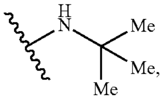
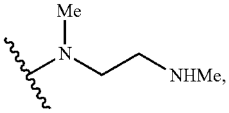
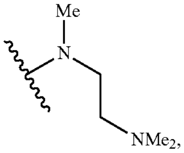
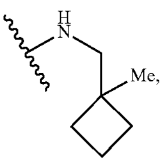
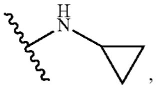
,
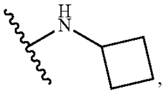
,
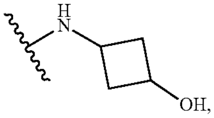
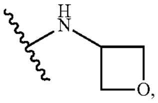
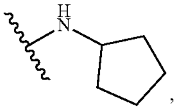
,
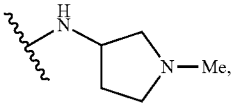
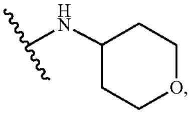
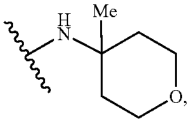
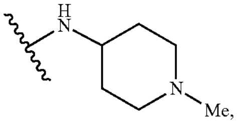
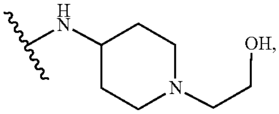
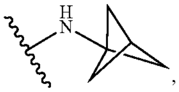
,
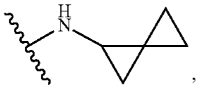
,
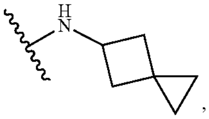
,
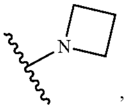
,
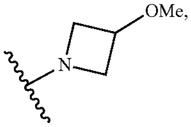
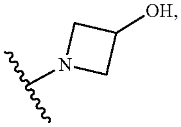
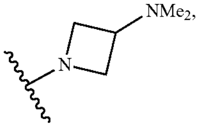
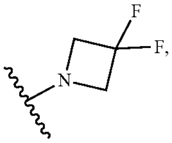
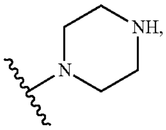
-continued
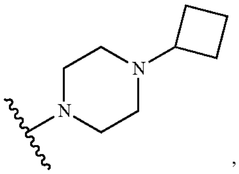
,
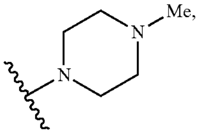
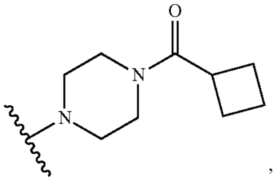
,
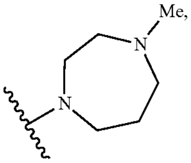
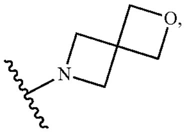
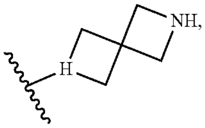
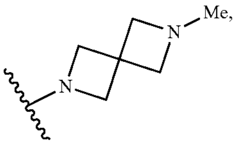
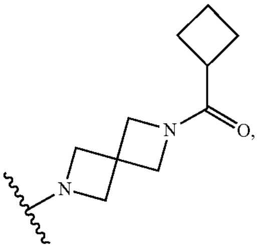
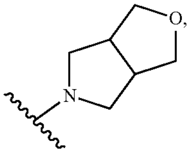
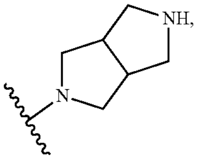
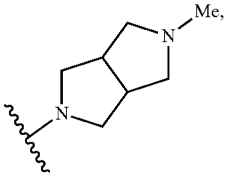
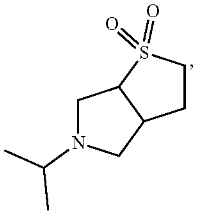
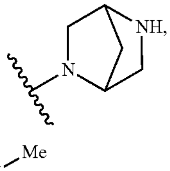
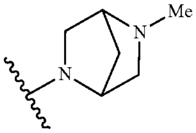
,
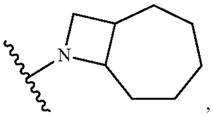
, -continued
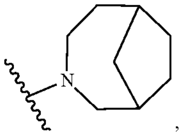,
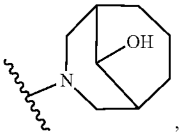,
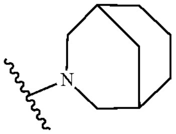,
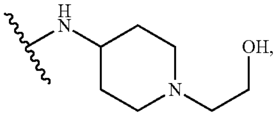
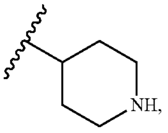
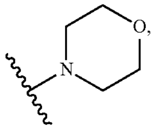
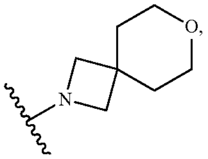
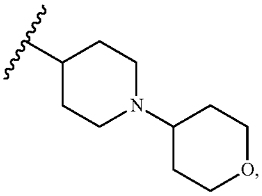 and
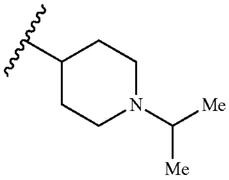
Preferably $R^3$ is selected from the following group ("preferred $R^3$ group"), consisting of
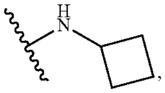
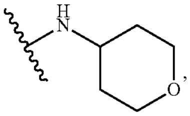,
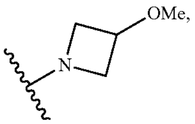
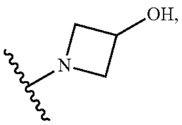
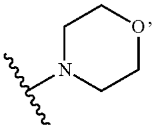, and
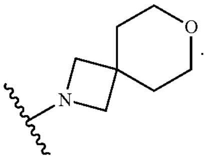
Examples of groups $R^4$ include:
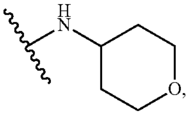
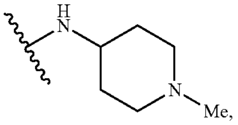
-continued
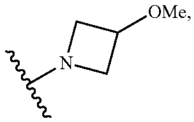
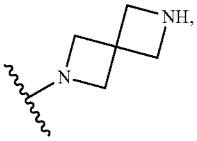
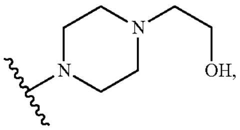
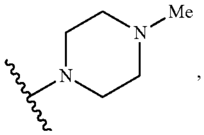,
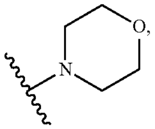
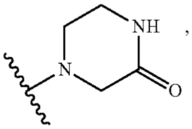,
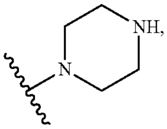
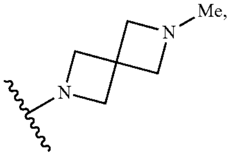
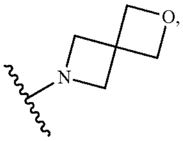
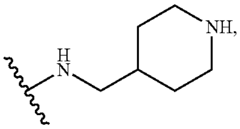
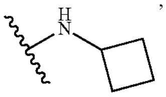,
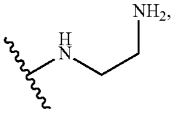
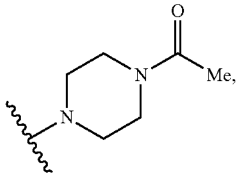
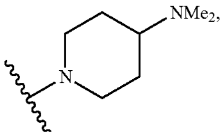
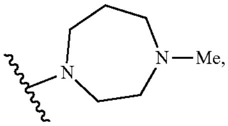
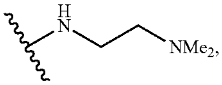
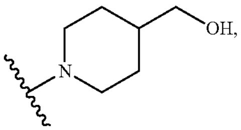
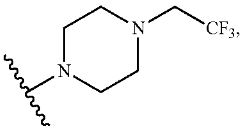
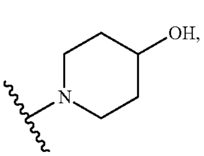
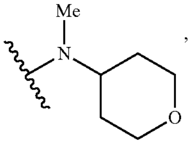,
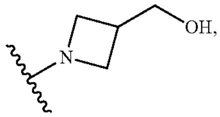
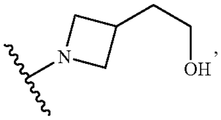, -continued

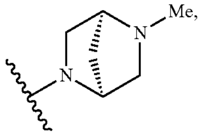 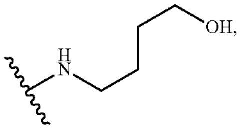

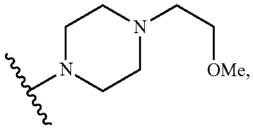 and

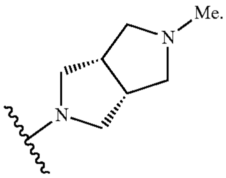

Preferably, $R^4$ is selected from the following group ("preferred $R^4$ group"), consisting of

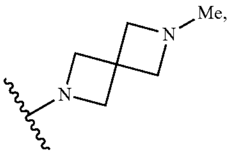 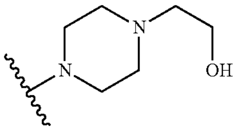 ,

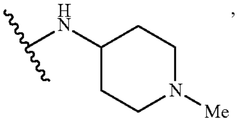 , 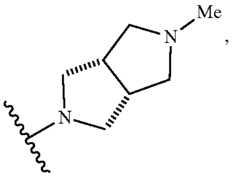 , and

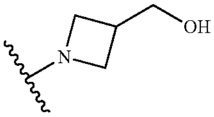

Examples of groups, $R^5$ are H,

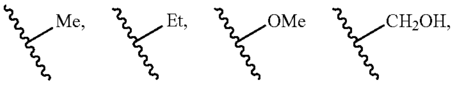

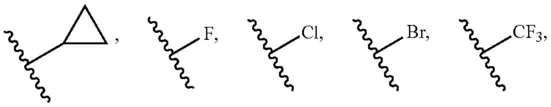

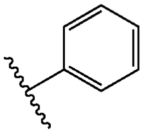 , 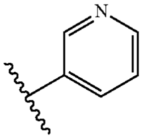 , 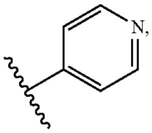

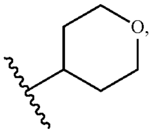 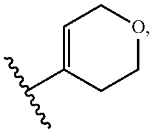 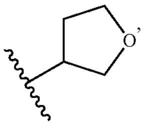

-continued

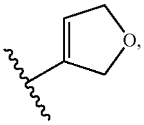 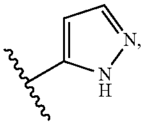 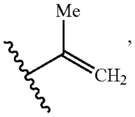 , and

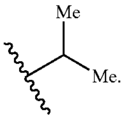

Preferably, $R^5$ is H or Me.

In one embodiment, compounds according to formula (Ib) have $R^1$ selected from the preferred $R^1$ group, $R^3$ selected from the preferred $R^3$ group, and $R^5$ equals H or Me.

In one embodiment, compounds according to formula (Ic) have $R^1$ selected from the preferred $R^1$ group, $R^4$ selected from the preferred $R^4$ group, and $R^5$ equals H or Me.

By way of exemplification and not of limitation, moieties of the formula

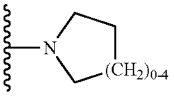 [SMILES: *N1CCCC1]

include

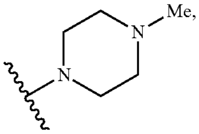 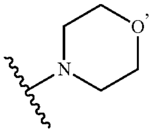 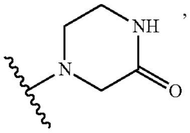 ,

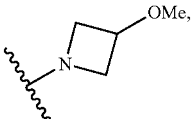 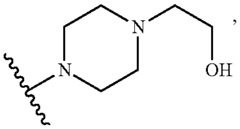 ,

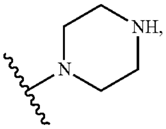 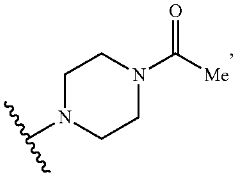 , 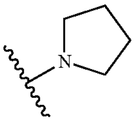 ,

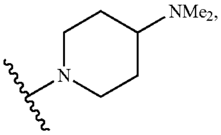 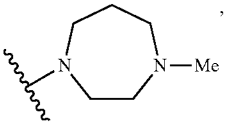 ,

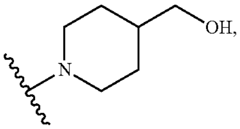 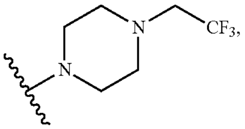

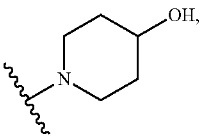 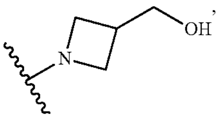

-continued
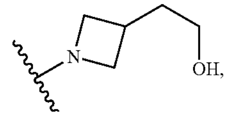
,
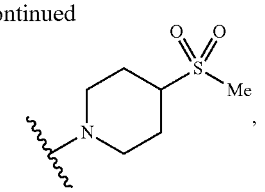
,
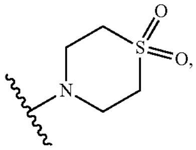
,
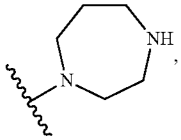
,
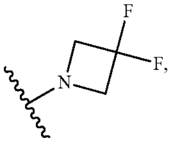
, and
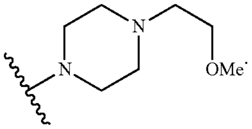
.
By way of exemplification and not of limitation, spiroalkyl groups include
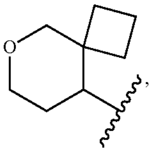
,
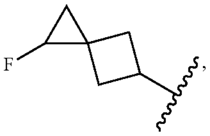
,
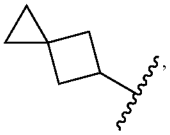
,
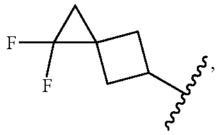
,
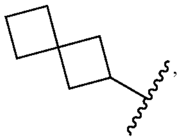
,
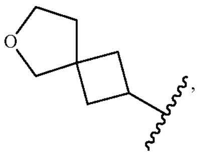
,
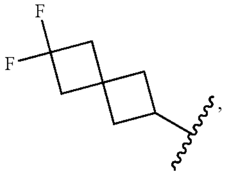
, and
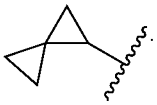
.
By way of exemplification and not of limitation, moieties of the formula
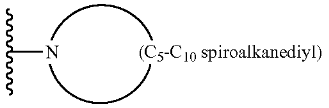
include
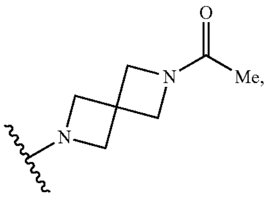
,
-continued
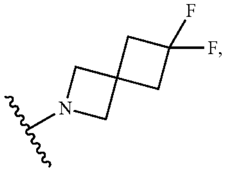
,
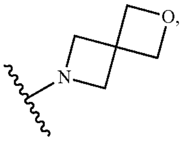
,
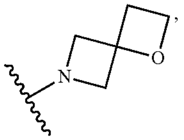
,
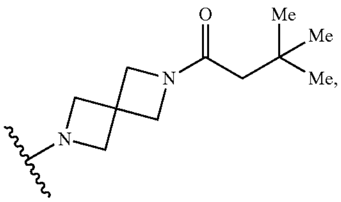
,
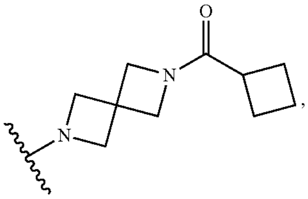
,
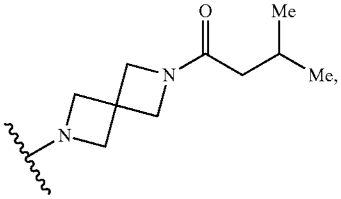
,
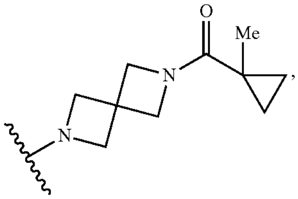
,
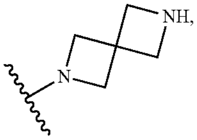
,
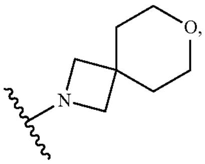
,
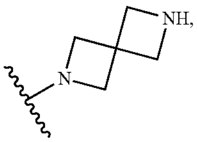
,
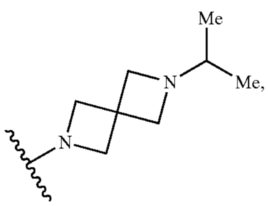
,
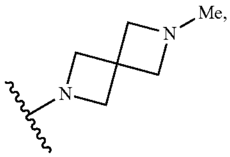
,
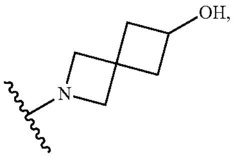
, -continued
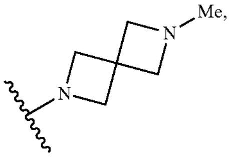
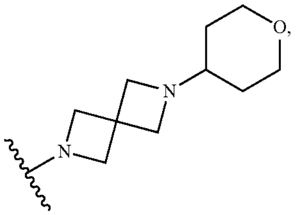
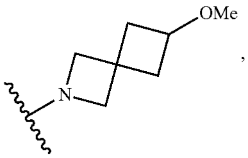 , 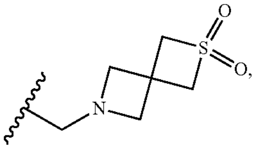
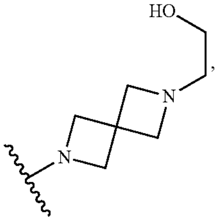 , 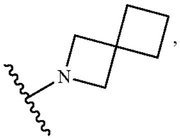 ,
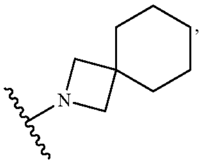 , 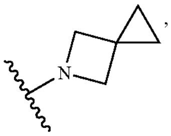 , and
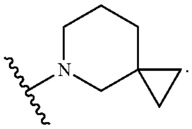
By way of exemplification and not of limitation, bicycloalkyl groups include
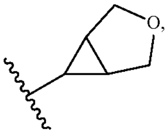 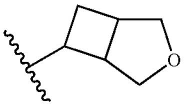 , and 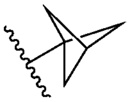 .
By way of exemplification and not of limitation, moieties of the formula
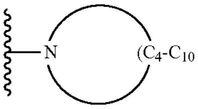 ($C_4$-$C_{10}$ bicycloalkanediyl)
include
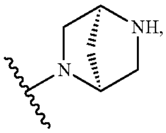 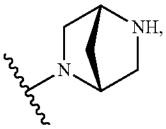
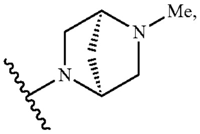 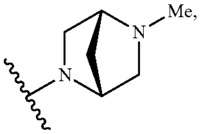
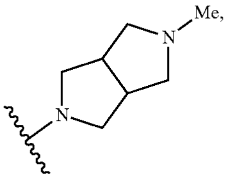 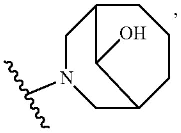 ,
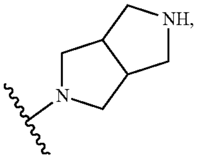 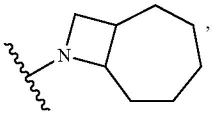 ,
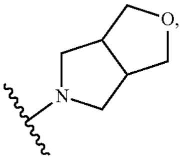 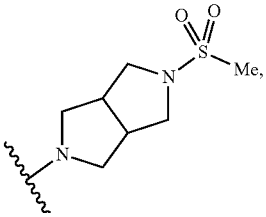
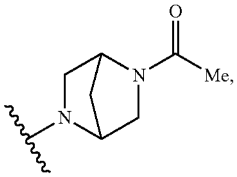 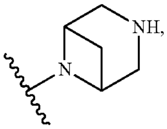
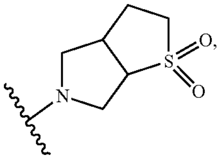 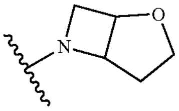 ,
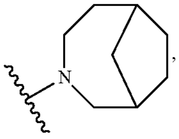 , 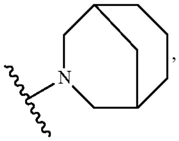 ,
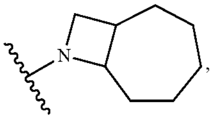 , 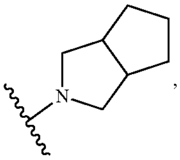 , and
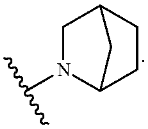

In one aspect, W is $-CH_2-NH[C(=O)]_{0-1}(C_1-C_4 \text{ alkanediyl})_{0-1}(C_3-C_8 \text{ cycloalkyl})$, especially $-CH_2-NH(C_3-C_8 \text{ cycloalkyl})$, with specific exemplary embodiments being

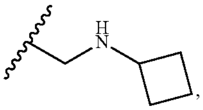,
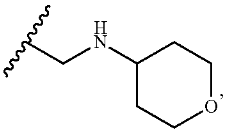, and
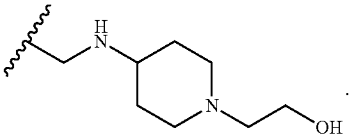.

In one aspect, W is $-CH_2-NH[C(=O)]_{0-1}(C_1-C_4 \text{ alkanediyl})_{0-1}(C_4-C_{10} \text{ bicycloalkyl})$, especially $-CH_2-NH(C_4-C_{10} \text{ bicycloalkyl})$, with a specific exemplary embodiment being

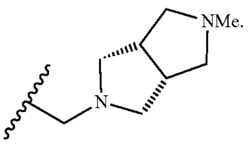

In one aspect, W is $-(C_3-C_8 \text{ cycloalkyl})$, with specific exemplary embodiments being

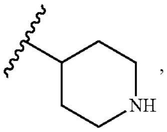,
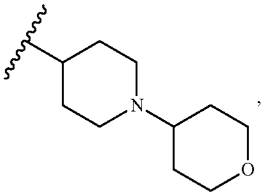, and
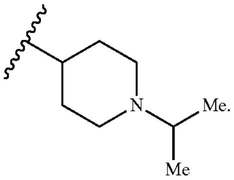

In one aspect, W is

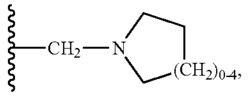

with specific exemplary embodiments being

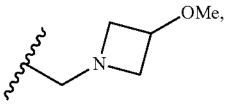
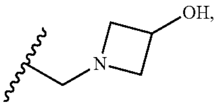 and
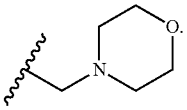

In one aspect, W is

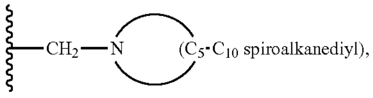

with a specific exemplary embodiment being

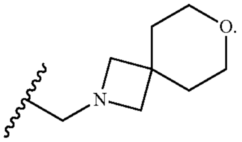 [SMILES: *CN1CC2(CCOCC2)C1]

In one aspect, W is

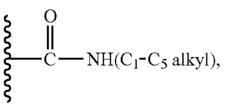

with specific exemplary embodiments being
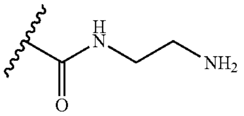
and
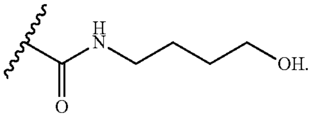
In one aspect, W is
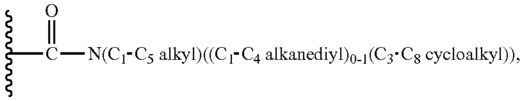
especially
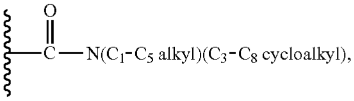
with a specific exemplary embodiment being
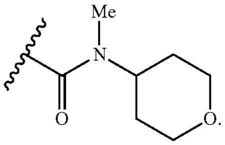 [SMILES: *C(=O)N(C)C1CCOCC1]
In one aspect, W is
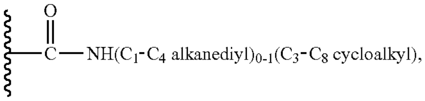
especially
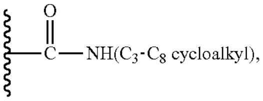
with specific exemplary embodiments being
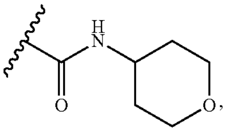
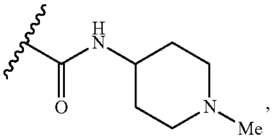
, and
-continued
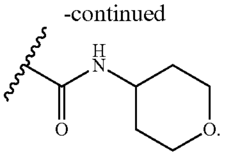
In one aspect, W is
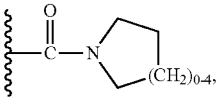
with specific exemplary embodiments being
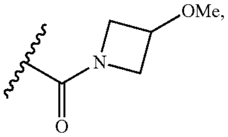
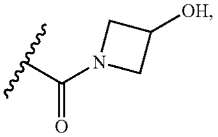
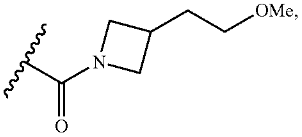
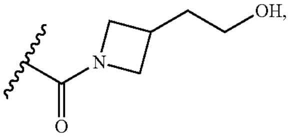
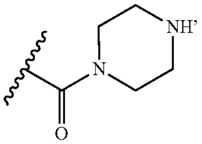
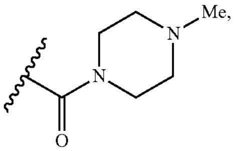
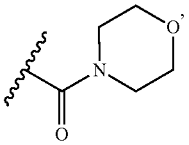
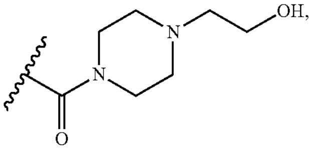
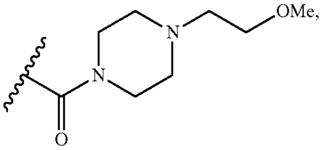
and
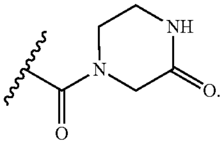
In one aspect, W is
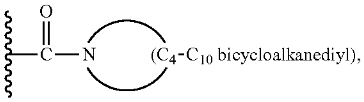

with specific exemplary embodiments being

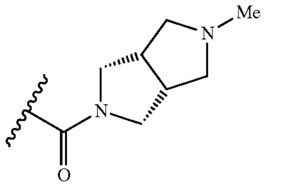

and

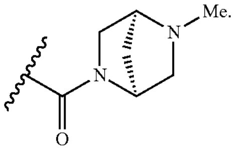

In one aspect, W is

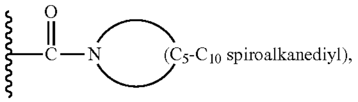 [SMILES: *C(N)=O ; "(C5-C10 spiroalkanediyl),"]

with specific exemplary embodiments being

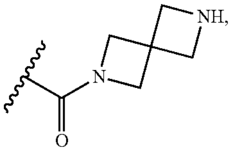

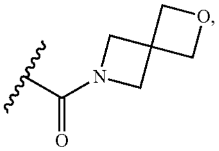

and

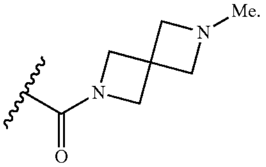

In one aspect, compounds of this disclosure are according to formula (Ia)

(Ia)

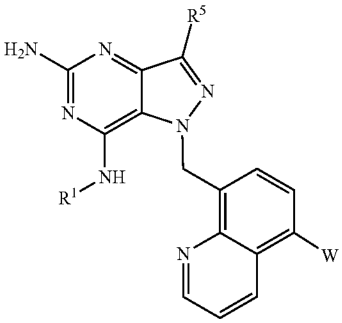

wherein $R^1$ is

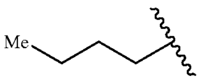

,

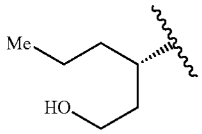

,

-continued

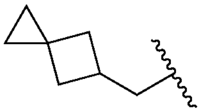

, or

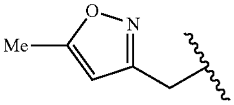

;

$R^5$ is H (preferably) or Me; and

W is

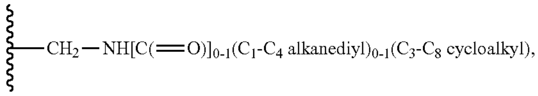

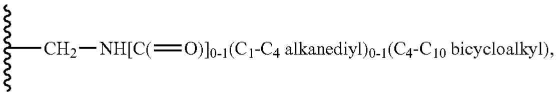

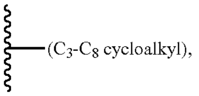

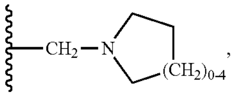

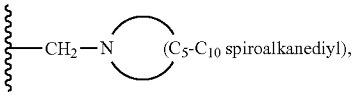

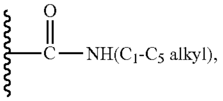

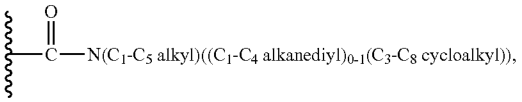

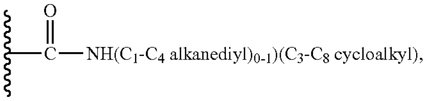

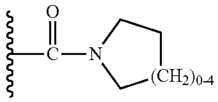

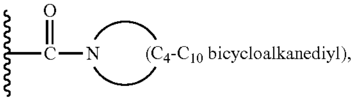

or

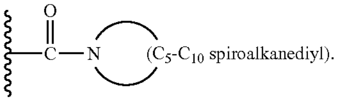

Some of the above exemplary alkyl, cycloalkyl, spiroalkyl, bicyloalkyl, etc., groups and moieties of the formula

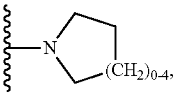

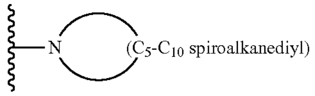

and

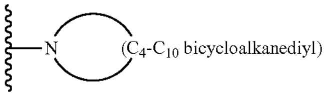

bear optional substituents and/or optionally have one or more $CH_2$ groups replaced by 0, $SO_2$, etc., as described in the BRIEF SUMMARY OF THE DISCLOSURE above.

Specific examples of compounds disclosed herein are shown in the following Table A. The table also provides data relating to biological activity: human TLR7 agonism reporter assay and/or induction of the CD69 gene in human whole blood, determined per the procedures provided hereinbelow. The right-most column contains analytical data (mass spectrum, LC/MS retention time, and NMR). In one embodiment, a compound of this disclosure has (a) a human TLR7 (hTLR7) Reporter Assay $EC_{50}$ value of less than 1,000 nM and (b) a human whole blood (hWB) CD69 induction $EC_{50}$ value of less than 1,000 nM. (Where an assay was performed multiple times, the reported value is an average.)

(Ia)

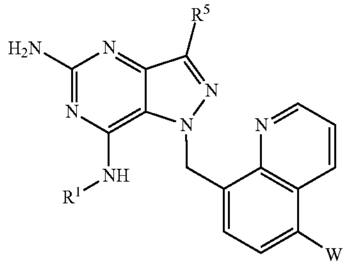

TABLE A

| Cpd. No. | Structure ($R^5$ = H unless noted otherwise) | TLR7 Agonism $EC_{50}$ (nM) | hWB CD69 $EC_{50}$ (nM) | Analytical Data (Mass spectrum, LC/MS Retention Time, $^1$H NMR (500 MHz, DMSO-d6)) |
|---|---|---|---|---|
| | Compounds According to Formula (Ia) | | | |
| 101 | 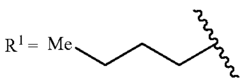 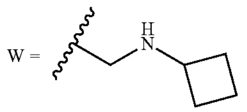 [SMILES: *CNC1CCC1] N7-butyl-1-({5-[(cyclobutyl-amino)methyl]quinolin-8-yl}methyl)-1H-pyrazolo[4,3-d]pyrimidine-5,7-diamine | 93.3 | 47.1 | LC/MS [M + H]$^+$ 430.9 LC/MS RT (min)/Method: 1.17/D δ 9.21 (s, 1H), 9.02 (d, J = 4.2 Hz, 1H), 8.75-8.69 (m, 1H), 7.79-7.72 (m, 3H), 7.67 (d, J = 7.3 Hz, 1H), 6.22 (s, 2H), 4.53 (s, 2H), 3.84-3.75 (m, 1H), 3.66-3.59 (m, 1H), 3.15 (s, 1H), 2.16 (q, J = 10.7, 9.7 Hz, 4H), 1.82-1.72 (m, 2H), 1.58 (q, J = 7.5 Hz, 2H), 1.28 (q, J = 7.4 Hz, 2H), 0.86 (t, J = 7.4 Hz, 3H). |
| 102 | 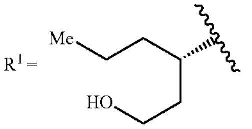 [SMILES: *[C@@H](CCC)CCO] 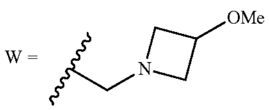 [SMILES: *CN1CC(OC)C1] (3S)-3-{[5-amino-1-({5-[(3-methoxyazetidin-1-yl)methyl]quinolin-8-yl}methyl)-1H-pyrazolo[4,3-d]pyrimidin-7-yl]amino}hexan-1-ol | 30.8 | 12.2 | LC/MS [M + H]$^+$: 490.9 LC/MS RT (min)/Method: 1.09/D δ 9.04-8.99 (m, 1H), 8.69 (dd, J = 8.7, 1.7 Hz, 1H), 7.67 (dd, J = 8.5, 4.3 Hz, 1H), 7.60 (s, 1H), 7.46 (d, J = 7.4 Hz, 1H), 7.12 (d, J = 7.3 Hz, 1H), 6.33-6.24 (m, 2H), 6.10 (d, J = 16.7 Hz, 1H), 5.62 (s, 2H), 4.24 (s, 1H), 3.98-3.89 (m, 2H), 3.20 (qd, J = 13.5, 12.2, 6.1 Hz, 2H), 3.10 (s, 3H), 2.87 (q, J = 6.9 Hz, 2H), 1.89 (s, 2H), 1.52 (dd, J = 13.0, 6.3 Hz, 2H), 1.34-1.20 (m, 2H), 1.02 (dt, J = 13.9, 7.3 Hz, 1H), 0.80 (s, 1H), 0.59 (t, J = 7.3 Hz, 3H) |
| 103 | 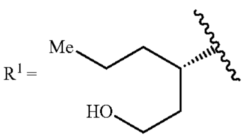 [SMILES: *[C@@H](CCC)CCO] 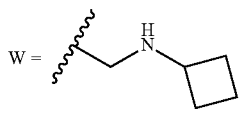 [SMILES: *CNC1CCC1] (3S)-3-{[5-amino-1-({5-[(cyclobutylamino)methyl]-quinolin-8-yl}methyl)-1H-pyrazolo[4,3-d]pyrimidin-7-yl]amino}hexan-1-ol | 13.8 | 10.6 | LC/MS [M + H]$^+$: 475.2 LC/MS RT (min)/Method: 1.11/D δ 9.01 (dd, J = 4.2, 1.7 Hz, 1H), 8.72 (dd, J = 8.6, 1.8 Hz, 1H), 7.66 (dd, J = 8.5, 4.3 Hz, 1H), 7.60 (s, 1H), 7.48 (d, J = 7.4 Hz, 1H), 7.15 (d, J = 7.4 Hz, 1H), 6.31-6.24 (m, 2H), 6.11 (d, J = 16.5 Hz, 1H), 5.60 (s, 2H), 4.29-4.19 (m, 1H), 4.01 (s, 1H), 3.21-3.11 (m, 2H), 2.04 (d, J = 9.5 Hz, 3H), 1.89 (s, 3H), 1.66 (t, J = 9.2 Hz, 2H), 1.52 (ddt, J = 26.4, 18.3, 8.8 Hz, 3H), 1.36-1.18 (m, 2H), 1.02 (dd, J = 13.9, 8.6 Hz, 1H), 0.84 (s, 2H), 0.61 (t, J = 7.3 Hz, 3H) |

TABLE A-continued

Compounds According to Formula (Ia)

| Cpd. No. | Structure ($R^5$ = H unless noted otherwise) | TLR7 Agonism $EC_{50}$ (nM) | hWB CD69 $EC_{50}$ (nM) | Analytical Data (Mass spectrum, LC/MS Retention Time, $^1$H NMR (500 MHz, DMSO-d6)) |
|---|---|---|---|---|
| 104 | $R^1$ = 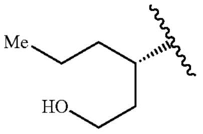 W = 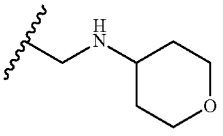 (3S)-3-({5-amino-1-[(5-{[(oxan-4-yl)amino]-methyl}quinolin-8-yl)methyl]-1H-pyrazolo[4,3-d]pyrimidin-7-yl}amino)hexan-1-ol | 44.8 | 13.4 | LC/MS [M + H]$^+$: 505.2 LC/MS RT (min)/Method: 0.87/D δ 9.02 (d, J = 4.2 Hz, 1H), 8.72 (d, J = 8.5 Hz, 1H), 7.68 (dd, J = 8.6, 4.2 Hz, 1H), 7.62-7.53 (m, 2H), 7.20 (d, J = 7.3 Hz, 1H), 6.39 (d, J = 8.9 Hz, 1H), 6.27 (d, J = 16.6 Hz, 1H), 6.12 (d, J = 16.4 Hz, 1H), 5.64 (s, 2H), 4.27-4.18 (m, 3H), 3.81 (d, J = 11.5 Hz, 2H), 3.29-3.21 (m, 2H), 3.18 (s, 1H), 3.22-3.13 (m, 1H), 2.77 (s, 1H), 1.86 (d, J = 32.1 Hz, 4H), 1.58-1.48 (m, 1H), 1.31 (s, 4H), 1.12-1.00 (m, 1H), 0.85 (s, 2H), 0.62 (t, J = 7.3 Hz, 3H) |
| 105 | $R^1$ = 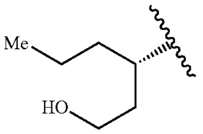 W = 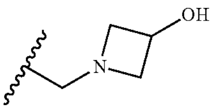 1-({8-[(5-amino-7-{[(3S)-1-hydroxyhexan-3-yl]amino}-1H-pyrazolo[4,3-d]pyrimidin-1-yl)methyl]quinolin-5-yl}methyl)azetidin-3-ol | 49.4 | 13.8 | LC/MS [M + H]$^+$: 477.1 LC/MS RT (min)/Method: 1.13/D δ 9.02 (d, J = 4.1 Hz, 1H), 8.69 (d, J = 8.8 Hz, 1H), 7.67 (dd, J = 8.5, 4.2 Hz, 1H), 7.60 (s, 1H), 7.44 (d, J = 7.3 Hz, 1H), 7.12 (d, J = 7.3 Hz, 1H), 6.33-6.21 (m, 2H), 6.11 (d, J = 16.5 Hz, 1H), 5.60 (s, 2H), 4.25 (s, 1H), 4.14 (t, J = 6.2 Hz, 1H), 3.95 (d, J = 5.3 Hz, 2H), 3.89 (s, 1H), 3.20 (s, 2H), 2.80 (t, J = 7.0 Hz, 2H), 1.85 (s, 3H), 1.51 (s, 1H), 1.28 (s, 2H), 1.07-0.95 (m, 1H), 0.88-0.75 (m, 2H), 0.60 (t, J = 7.3 Hz, 3H) |
| 106 | $R^1$ = 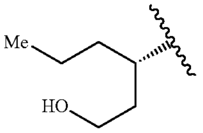 W = 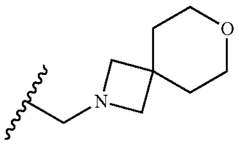 (3S)-3-[(5-amino-1-{[5-({7-oxa-2-azaspiro[3.5]nonan-2-yl}methyl)quinolin-8-yl]methyl}-1H-pyrazolo[4,3-d]pyrimidin-7-yl)amino]hexan-1-ol | 19.3 | 48.1 | LC/MS [M + H]$^+$: 531.2 LC/MS RT (min)/Method: 0.87/D δ 9.01 (dd, J = 4.3, 1.6 Hz, 1H), 8.71 (d, J = 8.5 Hz, 1H), 7.68 (dd, J = 8.6, 4.3 Hz, 1H), 7.63 (s, 1H), 7.49 (d, J = 7.3 Hz, 1H), 7.15 (d, J = 7.3 Hz, 1H), 6.52-6.47 (s, 1H), 6.31 (d, J = 16.6 Hz, 1H), 6.11 (d, J = 16.7 Hz, 1H), 5.88 (s, 1H), 4.30-4.23 (m, 2H), 4.10-4.01 (m, 2H), 3.20 (d, J = 6.7 Hz, 4H), 3.07 (s, 2H), 1.62 (t, J = 5.2 Hz, 5H), 1.54 (dd, J = 13.0, 6.1 Hz, 1H), 1.27 (s, 2H), 1.05 (s, 1H), 0.84 (s, 2H), 0.60 (t, J = 7.3 Hz, 3H). |
| 107 | $R^1$ = 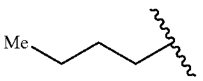 W = 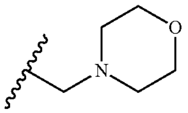 | 155.6 | 320.6 | LC/MS [M + H]$^+$: 447.1 LC/MS RT (min)/Method: 1.13/D δ 9.02 (dd, J = 4.3, 1.6 Hz, 1H), 8.80 (dd, J = 8.5, 1.8 Hz, 1H), 7.68 (dd, J = 8.6, 4.2 Hz, 1H), 7.57 (s, 1H), 7.48 (d, J = 7.3 Hz, 1H), 7.27 (d, J = 7.3 Hz, 1H), 6.15 (s, 2H), 5.64 (s, 2H), 3.85 (s, 2H), 3.48(s, 4H), 2.36 (s, 4H), 1.90 (s, 2H), 1.37 (p, J = 7.2 Hz, 2H), 1.06 (p, J = 7.4 Hz, 2H), 0.73 (t, J = 7.4 Hz, 3H) |

TABLE A-continued

Compounds According to Formula (Ia)

| Cpd. No. | Structure ($R^5$ = H unless noted otherwise) | TLR7 Agonism $EC_{50}$ (nM) | hWB CD69 $EC_{50}$ (nM) | Analytical Data (Mass spectrum, LC/MS Retention Time, $^1H$ NMR (500 MHz, DMSO-d6)) |
|---|---|---|---|---|
| | N7-butyl-1-({5-[(morpholin-4-yl)methyl]quinolin-8-yl}methyl)-1H-pyrazolo[4,3-d]pyrimidine-5,7-diamine | | | |
| 108 | $R^1$ = 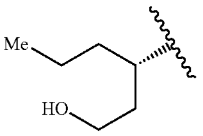 W = 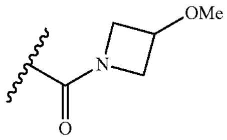 (3S)-3-[(5-amino-1-{[5-(3-methoxyazetidine-1-carbonyl)quinolin-8-yl]methyl}-1H-pyrazolo[4,3-d]pyrimidin-7-yl)amino]hexan-1-ol | 67.6 | 109.9 | LC/MS [M + H]$^+$: 505.2 LC/MS RT (min)/Method: 1.23/D δ 9.06 (d, J = 4.0 Hz, 1H), 8.57 (d, J = 8.7 Hz, 1H), 7.72 (dd, J = 8.7, 4.2 Hz, 1H), 7.62 (d, J = 9.4 Hz, 2H), 7.09 (t, J = 6.9 Hz, 1H), 6.35 (dd, J = 17.1, 10.7 Hz, 1H), 6.22 (ddd, J = 39.7, 16.0, 7.5 Hz, 2H), 5.61 (s, 2H), 4.34-4.26 (m, 1H), 4.24 (s, 1H), 4.19 (s, 1H), 4.09-4.00 (m, 1H), 3.92-3.88 (m, 1H), 3.14 (s, 4H), 1.88 (s, 2H), 1.54-1.48 (m, 1H), 1.36-1.20 (m, 2H), 1.12-1.00 (m, 1H), 0.82 (d, J = 17.1 Hz, 2H), 0.58 (q, J = 7.7 Hz, 3H). |
| 109 | $R^1$ = 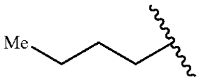 W = 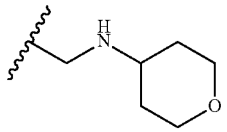 N7-butyl-1-[(5-{[(oxan-4-yl)amino]methyl}quinolin-8-yl)methyl]-1H-pyrazolo[4,3-d]pyrimidine-5,7-diamine | 55.2 | 41.5 | LC/MS [M + H]$^+$: 461.2 LC/MS RT (min)/Method: 1.16/E δ 9.20 (s, 1H), 9.03 (dd, J = 4.1, 1.5 Hz, 1H), 8.74 (dd, J = 8.5, 1.8 Hz, 1H), 7.82-7.72 (m, 3H), 7.69 (d, J = 7.4 Hz, 1H), 6.24 (s, 2H), 4.69 (s, 2H), 3.95 (dd, J = 11.5, 4.3 Hz, 2H), 3.64 (q, J = 6.9 Hz, 1H), 3.36-3.31(m, 1H), 2.09 (d, J = 12.4 Hz, 2H), 1.71-1.56 (m, 4H), 1.30 (h, J = 7.4 Hz, 2H), 0.87 (t, J = 7.4 Hz, 3H) |
| 110 | $R^1$ = 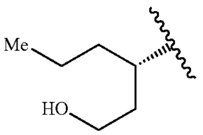 W = H (3S)-3-({5-amino-1-[(quinolin-8-yl)methyl]-1H-pyrazolo[4,3-d]pyrimidin-7-yl}amino)-hexan-1-ol | 286.9 | 729.2 | LC/MS [M + H]$^+$: 392.2 LC/MS RT(min)/Method: 1.32 δ 9.04 (dd, J = 4.2, 1.7 Hz, 1H), 8.48 (dd, J = 8.4, 1.7 Hz, 1H), 7.97 (d, J = 8.2 Hz, 1H), 7.67 (dd, J = 8.3, 4.2 Hz, 1H), 7.61 (s, 1H), 7.55 (t, J = 7.7 Hz, 1H), 7.22 (d, J = 7.2 Hz, 1H), 6.37-6.27 (m, 2H), 6.14 (d, J = 16.7 Hz, 1H), 5.62 (s, 2H), 4.25 (s, 1H), 3.25-3.14 (m, 1H), 1.57-1.49 (m, 1H), 1.38 (s, 2H), 1.27 (s, 1H), 1.04 (d, J = 8.8 Hz, 1H), 0.85 (s, 2H), 0.80 (s, 1H), 0.60 (t, J = 7.3 Hz, 3H). |
| 111 | $R^1$ = 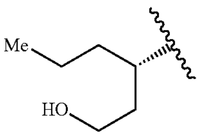 W = 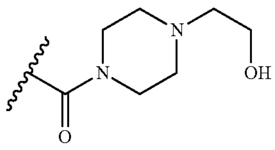 (3S)-3-{[5-amino-1-({5-[4-(2-hydroxyethyl)piperazine-1-carbonyl]quinolin-8-yl}me- | 66.0 | 57.7 | LC/MS [M + H]$^+$: 548.1 LC/MS RT (min)/Method: 1.02/D δ 9.09-9.04 (m, 1H), 8.27 (dd, J = 8.5, 1.7 Hz, 1H), 7.76-7.66 (m, 2H), 7.49 (d, J = 7.2 Hz, 1H), 7.20 (s, 1H), 6.39 (s, 1H), 6.31 (s, 2H), 6.17 (s, 1H), 4.32 (s, 1H), 3.27 (s, 1H), 3.10 (s, 1H), 3.04 (s, 1H), 2.60 (s, 2H), 2.44 (s, 2H), 2.36 (s, 1H), 1.89 (s, 1H), 1.57 (s, 2H), 1.46 (s, 1H), 1.33 (s, 2H), 1.21 (s, 2H), 0.91 (s, 2H), 0.64 (s, 3H). |

TABLE A-continued

Compounds According to Formula (Ia)

| Cpd. No. | Structure ($R^5$ = H unless noted otherwise) | TLR7 Agonism $EC_{50}$ (nM) | hWB CD69 $EC_{50}$ (nM) | Analytical Data (Mass spectrum, LC/MS Retention Time, $^1H$ NMR (500 MHz, DMSO-d6)) |
|---|---|---|---|---|
| | thyl)-1H-pyrazolo[4,3-d] pyrimidin-7-yl]amino} hexan-1-ol | | | |
| 112 | $R^1$ = 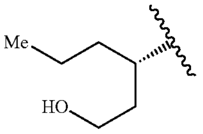<br>W = 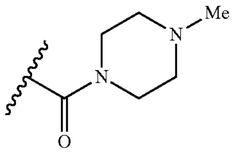<br>(3S)-3-[(5-amino-1-{[5-(4-methylpiperazine-1-carbonyl) quinolin-8-yl]methyl}-1H-pyrazolo[4,3-d]pyrimidin-7-yl)amino]hexan-1-ol | 4.9 | 5.1 | LC/MS [M + H]$^+$: 518.1<br>LC/MS RT (min)/Method: 1.00/D<br>δ 9.08- 9.03 (m, 1H), 8.27 (dd, J = 8.5, 1.9 Hz, 1H), 7.73 (dd, J = 8.6, 4.2 Hz, 1H), 7.51 (d, J = 7.4 Hz, 1H), 7.25(s, 1H), 7.11 (s, 1H), 6.57 (s, 1H), 6.35(s, 2H), 6.19 (s, 2H), 4.36 (s, 1H), 3.85 (s, 1H), 3.56-3.47 (m, 1H), 3.32-3.22 (m, 1H), (s, 1H), 3.15 (s, 1H), 2.97 (s, 3H), 2.26 (s, 2H), 1.75 (d, J = 9.2 Hz, 1H), 1.56 (s, 2H), 1.42-1.33 (m, 2H), 1.31-1.19 (m, 2H), 0.94 (s, 2H), 0.65 (s, 3H). |
| 113 | $R^1$ = 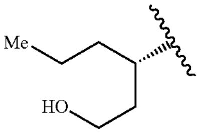<br>W = 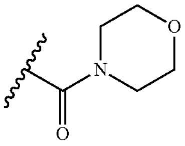<br>(3S)-3-[(5-amino-1-{[5-(morpholine-4-carbonyl) quinolin-8-yl]methyl}-1H-pyrazolo[4,3-d]pyrimidin-7-yl)amino]hexan-1-ol | 186.3 | 131.6 | LC/MS [M + H]$^+$: 505.1<br>LC/MS RT (min)/Method: 1.22/D<br>δ 9.10-9.05 (m, 1H), 8.32 (dd, J = 8.5, 1.9 Hz, 1H), 7.73 (dd, J = 8.6, 4.2 Hz, 1H), 7.67 (s, 1H), 7.52 (d, J = 7.4 Hz, 1H), 7.18 (s, 1H), 6.37 (s, 2H), 6.16 (s, 2H), 4.31 (s, 1H), 3.71 (s, 1H), 3.15 (s, 1H), 3.11 (s, 1H), 3.02 (s, 1H), 1.89 (d, J = 1.2 Hz, 1H), 1.56 (s, 2H), 1.33 (s, 2H), 1.19 (d, J = 13.3 Hz, 2H), 0.90 (s, 3H), 0.63 (s, 3H). |
| 114 | $R^1$ = 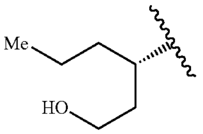<br>W = 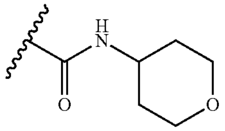<br>8-[(5-amino-7-{[(3S)-1-hydroxyhexan-3-yl]amino}-1H-pyrazolo[4,3-d]pyrimidin-1-yl)methyl]-N-(oxan-4-yl)quinoline-5-carboxamide | 75.2 | 369.3 | LC/MS [M + H]$^+$: 519.2<br>LC/MS RT (min)/Method: 1.25/D<br>δ 9.05 (d, J = 4.0 Hz, 1H), 8.71 (d, J = 8.7 Hz, 1H), 8.54 (d, J = 7.8 Hz, 1H), 7.71 (dd, J = 8.7, 4.3 Hz, 1H), 7.66-7.61 (m, 2H), 7.17 (d, J = 7.4 Hz, 1H), 6.44-6.34 (m, 2H), 6.17 (d, J = 16.6 Hz, 1H), 5.79 (s, 2H), 4.26 (s, 1H), 4.03 (s, 1H), 3.85 (d, J = 11.4 Hz, 2H), 3.41-3.36 (m, 1H), 3.22 (s, 2H), 1.89 (d, J = 1.5 Hz, 1H), 1.80 (s, 2H), 1.51 (s, 3H), 1.41-1.31 (m, 1H), 1.27 (s, 1H), 1.08 (s, 1H), 0.88 (s, 1H), 0.82 (s, 1H), 0.62 (t, J = 7.3 Hz, 3H). |

TABLE A-continued

Compounds According to Formula (Ia)

| Cpd. No. | Structure ($R^5$ = H unless noted otherwise) | TLR7 Agonism $EC_{50}$ (nM) | hWB CD69 $EC_{50}$ (nM) | Analytical Data (Mass spectrum, LC/MS Retention Time, $^1$H NMR (500 MHz, DMSO-d6)) |
|---|---|---|---|---|
| 115 | $R^1$ = 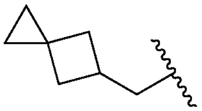<br>W = 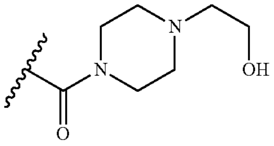<br>2-{4-[8-({5-amino-7-[({spiro-[2.3]hexan-5-yl}methyl)-amino]-1H-pyrazolo[4,3-d]pyrimidin-1-yl}methyl)-quinoline-5-carbonyl]-piperazin-1-yl}ethan-1-ol | 467.6 | 756.2 | LC/MS [M + H]$^+$: 542.3<br>LC/MS RT (min)/Method: 1.22/D<br>δ 9.21 (d, J = 4.3 Hz, 1H), 8.37 (d, J = 7.9 Hz, 1H), 7.84 (dd, 7 = 8.5, 4.1 Hz, 1H), 7.72 (s, 1H), 7.59 (d, J = 7.6 Hz, 1H), 7.32 (d, J = 7.5 Hz, 1H), 6.38 (s, 1H), 6.32 (s, 1H), 5.79 (s, 2H), 3.17-3.12 (m, 2H), 2.49 (t, J = 6.2 Hz, 2H), 2.40 (s, 1H), 2.25 (s, 2H), 1.98-1.86 (m, 10H), 1.70 (s, 2H), 0.95-0.93 (m, 1H), 0.37 (s, 3H). |
| 116 | $R^1$ = 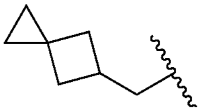<br>W = 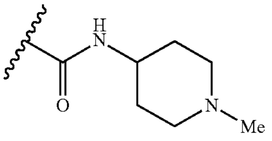<br>8-({5-amino-7-[({spiro-[2.3]hexan-5-yl}methyl)-amino]-1H-pyrazolo[4,3-d]pyrimidin-1-yl}methyl)-N-(1-methylpiperidin-4-yl)quinoline-5-carboxamide | 280.2 | 291.3 | LC/MS [M + H]$^+$: 526.2<br>LC/MS RT (min)/Method: 1.31/D<br>δ 9.15 (s, 1H), 9.01 (d, J = 4.1 Hz, 1H), 8.76 (s, 1H), 8.67 (d, J = 8.6 Hz, 1H), 7.75 (s, 1H), 7.72-7.66 (m, 2H), 7.58 (s, 1H), 6.24 (s, 2H), 4.10-4.01 (m, 1H), 3.78 (s, 2H), 3.45 (s, 2H), 3.15 (s, 1H), 3.10 (s, 1H), 2.75 (s, 3H), 2.10 (s, 2H), 2.00 (s, 2H), 1.84 (d, J = 7.7 Hz, 2H), 1.73 (s, 2H), 0.33 (s, 4H). |
| 117 | $R^1$ = 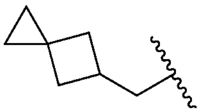<br>W = 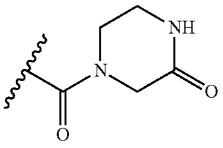<br>4-[8-({5-amino-7-[({spiro-[2.3]hexan-5-yl}methyl)-amino]-1H-pyrazolo[4,3-d]pyrimidin-1-yl}methyl)-quinoline-5-carbonyl]-piperazin-2-one | 447.2 | 266.5 | LC/MS [M + H]$^+$: 512.4<br>LC/MS RT (min)/Method: 1.30/D<br>δ 9.09 (d, J = 4.2 Hz, 1H), 8.34 (d, J = 8.5 Hz, 1H), 8.11 (s, 1H), 7.71 (dd,J = 8.7, 4.3 Hz, 1H), 7.61 (s, 1H), 7.55 (dd, J = 19.4, 7.3 Hz, 1H), 7.37 (s, 1H), 7.22 (dd, J = 21.5, 7.4 Hz, 1H), 6.25 (s, 2H), 5.78 (s, 2H), 4.23 (s, 1H), 3.22 (s, 2H), 3.02 (s, 2H), 1.88 (d, J = 14.1 Hz, 1H), 1.84 (d, J = 9.3 Hz, 2H), 1.62 (d, J = 8.9 Hz, 2H), 0.27 (s, 4H). |

TABLE A-continued

Compounds According to Formula (Ia)

| Cpd. No. | Structure ($R^5$ = H unless noted otherwise) | TLR7 Agonism $EC_{50}$ (nM) | hWB CD69 $EC_{50}$ (nM) | Analytical Data (Mass spectrum, LC/MS Retention Time, $^1H$ NMR (500 MHz, DMSO-d6)) |
|---|---|---|---|---|
| 118 | $R^1$ = 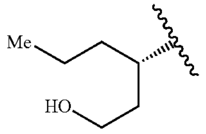<br>W = 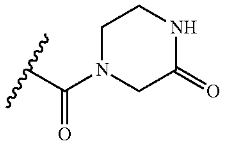<br>4-{8-[(5-amino-7-{[(3S)-1-hydroxyhexan-3-yl]amino}-1H-pyrazolo[4,3-d]pyrimidin-1-yl)methyl]quinoline-5-carbonyl}piperazin-2-one | 311.2 | 208.1 | LC/MS [M + H]+: 517.9<br>LC/MS RT (min)/Method: 1.09/D<br>δ 9.07 (d, J = 4.2 Hz, 1H), 8.33 (d, J = 8.5 Hz, 1H), 8.12 (s, 1H), 7.71 (dd, J = 8.5, 4.2 Hz, 1H), 7.63 (s, 1H), 7.54 (dd, J = 16.8, 7.4 Hz, 1H), 7.18-7.10 (m, 1H), 6.35 (s, 2H), 6.18 (d,J = 17.5 Hz, 1H), 5.66 (s, 1H), 4.23 (s, 1H), 3.69 (s, 3H), 3.34 (s, 1H), 3.24 (s, 2H), 3.06 (s, 2H), 1.53 (s, 1H), 1.29 (s, 2H), 1.16-1.09 (m, 1H), 0.90-0.82 (m, 2H), 0.61 (t, J = 7.6 Hz, 3H) |
| 119 | $R^1$ = 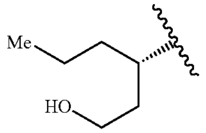<br>W = 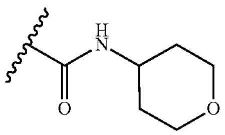<br>$R^5$ = Me<br>8-[(5-amino-7-{[(3S)-1-hydroxyhexan-3-yl]amino}-3-methyl-1H-pyrazolo[4,3-d]pyrimidin-1-yl)methyl]-N-(oxan-4-yl)quinoline-5-carboxamide | 605.5 | 1,000.0 | LC/MS [M + H]+: 533.2<br>LC/MS RT (min)/Method: 1.05/D<br>δ 9.03 (dd, J = 4.4, 1.7 Hz, 1H), 8.70 (dd, J = 8.5, 1.7 Hz, 1H), 8.56 (d, J = 7.7 Hz, 1H), 7.70 (dd, J = 8.7, 4.3 Hz, 1H), 7.64 (d, J = 7.4 Hz, 1H), 7.25 (d, J = 7.4 Hz, 1H), 6.63(s, 1H), 6.25 (d, J = 16.7 Hz, 1H), 6.07 (d, J = 16.5 Hz, 1H), 5.83 (s, 1H), 4.35-4.24 (m, 1H), 4.04 (d, J = 10.5 Hz, 1H), 3.85 (d, J = 11.5 Hz, 2H), 3.59-3.44 (m, 1H), 3.39 (t, J = 11.4 Hz, 1H), 3.30-3.21 (m, 2H), 2.26 (s, 3H), 1.90 (s, 1H), 1.86-1.77 (m, 2H), 1.64-1.46 (m, 3H), 1.45-1.37 (m, 1H), 1.36-1.27 (m, 1H), 1.21-1.10 (m, 1H), 1.01-0.81 (m, 2H), 0.65 (t, J = 7.3 Hz, 3H). |
| 120 | $R^1$ = 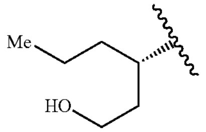<br>W = 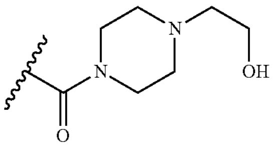<br>$R^5$ = Me<br>(3S)-3-{[5-amino-1-({5-[4-(2-hydroxyethyl)piperazine-1-carbonyl]quinolin-8-yl}methyl)-3-methyl-1H-pyrazolo[4,3-d]pyrimidin-7-yl]amino}hexan-1-ol | 881.5 | 1,000.0 | LC/MS [M + H]+: 562.3<br>LC/MS RT (min)/Method: 1.08/D<br>δ 9.05 (d, J = 4.4 Hz, 1H), 8.26 (d, J = 8.5 Hz, 1H), 7.72 (dd, J = 8.5, 4.1 Hz, 1H), 7.48 (d, J = 7.3 Hz, 1H), 7.21 (s, 1H), 6.68 (s, 1H), 6.26 (s, 1H), 6.16 (s, 2H), 5.96 (s, 1H), 4.32 (s, 2H), 3.53-3.45 (m, 2H), 3.27 (s, 1H), 3.16 (s, 1H), 3.09 (s, 1H), 3.03 (s, 1H), 2.58 (s, 2H), 2.42 (s, 2H), 2.34 (d, J = 15.0 Hz, 1H), 2.27 (s, 3H), 1.89 (s, 1H), 1.57 (s, 2H), 1.45(s, 1H), 1.33 (s, 2H), 1.20 (s, 1H), 0.91 (s, 2H), 0.62 (s, 3H). |

TABLE A-continued

Compounds According to Formula (Ia)

| Cpd. No. | Structure ($R^5$ = H unless noted otherwise) | TLR7 Agonism $EC_{50}$ (nM) | hWB CD69 $EC_{50}$ (nM) | Analytical Data (Mass spectrum, LC/MS Retention Time, $^1H$ NMR (500 MHz, DMSO-d6)) |
|---|---|---|---|---|
| 121 | $R^1$ = 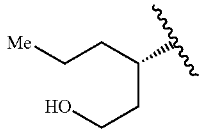 W = 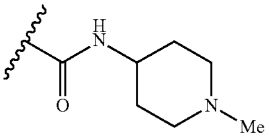 8-[(5-amino-7-{[(3S)-1-hydroxyhexan-3-yl]amino}-1H-pyrazolo[4,3-d]pyrimidin-1-yl)methyl]-N-(1-methyl-piperidin-4-yl)quinoline-5-carboxamide | 267.0 | 152.6 | LC/MS $[M + H]^+$: 532.3 LC/MS RT(min)/Method: 0.76/D δ 9.05 (d, J = 3.4 Hz, 1H), 8.70 (d, J = 8.7 Hz, 1H), 8.46 (d, J = 7.6 Hz, 1H), 7.70 (dd, J = 8.6, 4.2 Hz, 1H), 7.64-7.58 (m, 2H), 7.16 (d, J = 7.4 Hz, 1H), 6.36 (d, J = 16.6 Hz, 1H), 6.30-6.22 (m, 1H), 6.16 (d, J = 16.7 Hz, 1H), 5.60 (s, 2H), 4.24 (d, J = 8.8 Hz, 1H), 3.76 (s, 1H), 3.49 (s, 2H), 3.21 (t, J = 6.5 Hz, 1H), 2.13 (s, 3H), 1.96 (t, J = 11.4 Hz, 2H), 1.85 (s, 1H), 1.80 (s, 2H), 1.63 (s, 1H), 1.52 (m, 5H), 1.06 (d, J = 8.7 Hz, 1H), 0.85 (m, 1H), 0.61 (t, J = 7.3 Hz, 3H). |
| 122 | $R^1$ = 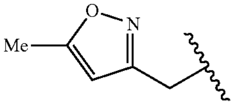 W = 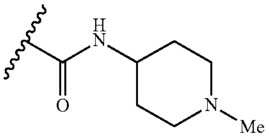 8-[(5-amino-7-{[(5-methyl-1,2-oxazol-3-yl)methyl]-amino}-1H-pyrazolo[4,3-d]pyrimidin-1-yl)methyl]-N-(1-methylpiperidin-4-yl)quinoline-5-carboxamide | 308.7 | 54.0 | LC/MS $[M + H]^+$: 527.3 LC/MS RT (min)/Method: 1.01/D δ 8.84 (dd, J = 4.1, 1.7 Hz, 1H), 8.78 (s, 1H), 8.64 (d, J = 8.9 Hz, 1H), 7.77 (s, 1H), 7.72-7.61 (m, 3H), 6.24 (s, 2H), 6.18 (s, 1H), 4.88 (d, J = 5.4 Hz, 2H), 4.18 (d, J = 5.8 Hz, 1H), 4.06 (s, 1H), 3.10 (s, 1H), 2.33 (s, 3H), 2.11 (s, 3H), 2.00 (s, 2H), 1.73 (d, J = 12.5 Hz, 2H), 1.62 (s, 2H), 1.52 (s, 2H). |
| 123 | $R^1$ = 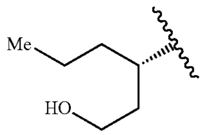 W = 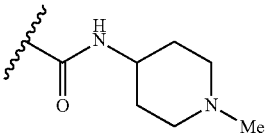 $R^5$ = Me 8-[(5-amino-7-{[(3S)-1-hydroxyhexan-3-yl]amino}-3-methyl-1H-pyrazolo[4,3-d]pyrimidin-1-yl)methyl]-N-(1-methylpiperidin-4-yl)quinoline-5-carboxamide | 731.6 | 660.7 | LC/MS $[M + H]^+$: 546.1 LC/MS RT (min)/Method: 1.12/D δ 9.03 (dd, J = 4.3, 1.6 Hz, 1H), 8.68 (dd, J = 8.7, 1.8 Hz, 1H), 8.47 (d, J = 7.8 Hz, 1H), 7.69 (dd, J = 8.6, 4.2 Hz, 1H), 7.61 (d, J = 7.4 Hz, 1H), 7.20 (d,J = 7.4 Hz, 1H), 6.37 (d, J = 9.1 Hz, 1H), 6.22 (d, J = 16.5 Hz, 1H), 6.06 (d, J = 16.6 Hz, 1H), 5.58 (s, 2H), 4.29-4.21 (m, 1H), 3.77 (s, 1H), 3.63 (s, 1H), 3.56 (d, J = 2.9 Hz, 1H), 3.22 (s, 2H), 2.97 (s, 1H), 2.73 (d, J = 11.0 Hz, 2H), 2.25 (s, 3H), 2.14 (s, 3H), 2.00 (t, J = 11.6 Hz, 2H), 1.81 (s, 2H), 1.60-1.48 (m,3H), 1.29 (dd, J = 14.4, 9.1 Hz, 1H), 0.85 (s, 2H), 0.62 (t, J = 7.4 Hz, 3H). |

TABLE A-continued

Compounds According to Formula (Ia)

| Cpd. No. | Structure ($R^5$ = H unless noted otherwise) | TLR7 Agonism $EC_{50}$ (nM) | hWB CD69 $EC_{50}$ (nM) | Analytical Data (Mass spectrum, LC/MS Retention Time, $^1H$ NMR (500 MHz, DMSO-d6)) |
|---|---|---|---|---|
| 124 | $R^1$ = 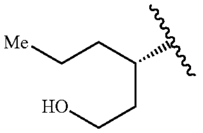<br>W = 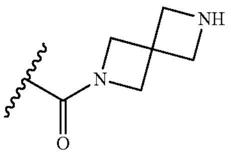<br>(3S)-3-({5-amino-1-[(5-{2,6-diazaspiro[3.3]heptane-2-carbonyl}quinolin-8-yl)methyl]-1H-pyrazolo[4,3-d]pyrimidin-7-yl}amino)hexan-1-ol | 440.2 | 247.9 | LC/MS [M + H]$^+$: 516.2<br>LC/MS RT (min)/Method: 1.05/D<br>δ 9.06 (d, J = 3.5 Hz, 1H), 8.58 (d, J = 8.5 Hz, 1H), 7.71 (dd, J = 8.6, 4.2 Hz, 1H), 7.65-7.57 (m, 2H), 7.07 (d, J = 7.4 Hz, 1H), 6.34 (d, J = 17.0 Hz, 1H), 6.28-6.16 (m, 2H), 5.62 (s, 2H), 4.21 (s, 2H), 4.00 (q, J = 9.5 Hz, 2H), 3.80 (s, 2H), 3.76-3.65 (m, 3H), 3.17 (dd, J = 13.2, 6.2 Hz, 2H), 1.83 (d, J = 3.3 Hz, 3H), 1.52 (s, 1H), 1.27 (s, 2H), 1.08 (dt, J = 14.0, 7.6 Hz, 1H), 0.84 (s, 2H), 0.60 (t, J = 7.3 Hz, 3H) |
| 125 | $R^1$ = 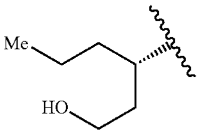<br>W = 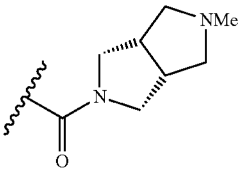<br>(3S)-3-{[1-([5-[(3aR,6aS)-5-methyl-octahydropyrrolo[3,4-c]pyrrole-2-carbonyl]quinolin-8-yl}methyl)-5-amino-1H-pyrazolo[4,3-d]pyrimidin-7-yl]amino}hexan-1-ol | 33.7 | 83.3 | LC/MS [M + H]$^+$: 544.2<br>LC/MS RT (min)/Method: 1.06/D<br>δ 9.03 (d, J = 3.8 Hz, 1H), 8.39 (s, 1H), 8.18 (d, J = 11.9 Hz, 1H), 7.89 (s, 1H), 7.81 (s, 1H), 7.71 (s, 1H), 7.67-7.56 (m, 2H), 7.42 (d, J = 7.3 Hz, 1H), 6.40 (dd, J = 16.1, 6.3 Hz, 1H), 6.26 (t, J = 17.0 Hz, 1H), 4.50 (s, 2H), 3.97 (s, 1H), 3.84(s, 1H), 3.60 (s, 1H), 3.08 (s, 1H), 2.82 (s, 4H), 1.76-1.65(m, 3H), 1.64-1.57 (m, 3H), 1.46 (s, 4H), 1.08 (s, 3H), 0.74 (q, J = 7.1 Hz, 3H). |
| 126 | $R^1$ = 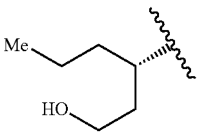<br>W = 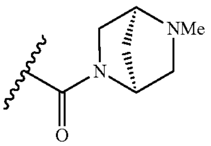<br>(3S)-3-{[5-amino-1-({5-[(1R,4R)-5-methyl-2,5-diazabicyclo[2.2.1]heptane-2-carbonyl]quinolin-8-yl}methyl)-1H-pyrazolo[4,3-d]pyrimidin-7-yl]amino}hexan-1-ol | 191.3 | 49.7 | LC/MS [M + H]$^+$: 530.4<br>LC/MS RT (min)/Method: 1.05/D<br>δ 9.07 (d, J = 4.1 Hz, 1H), 8.34 (t, J = 7.9 Hz, 1H), 7.72 (dt, J = 8.2, 3.6 Hz, 1H), 7.63 (d, J = 2.7 Hz, 1H), 7.54 (d, J = 7.4 Hz, 1H), 7.12 (dd, J = 7.5, 3.8 Hz, 1H), 6.33 (dd, J = 16.6, 10.2 Hz, 2H), 6.21 (dd, J = 16.8, 4.9 Hz, 1H), 5.64 (s, 2H), 4.73 (s, 1H), 4.26 (s, 1H), 3.17 (s, 2H), 3.06-2.94 (m, 1H), 2.88 (d, J = 9.7 Hz, 1H), 2.30 (s, 3H), 2.22 (s, 1H), 1.89 (s, 2H), 1.86 (d, J = 10.0 Hz, 1H), 1.76 (d, J = 9.5 Hz, 1H), 1.69 (s, 1H), 1.52 (dt, J = 12.9, 6.4 Hz, 1H), 1.30 (dq, J = 14.0, 6.9, 5.9 Hz, 1H), 1.14 (dq, J = 15.0, 7.8 Hz, 2H), 0.88 (p, J = 7.8 Hz, 2H), 0.62 (q, J = 7.6 Hz, 3H). |

TABLE A-continued

Compounds According to Formula (Ia)

| Cpd. No. | Structure ($R^5$ = H unless noted otherwise) | TLR7 Agonism $EC_{50}$ (nM) | hWB CD69 $EC_{50}$ (nM) | Analytical Data (Mass spectrum, LC/MS Retention Time, $^1H$ NMR (500 MHz, DMSO-d6)) |
|---|---|---|---|---|
| 127 | 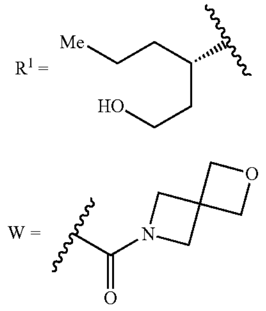<br>(3S)-3-({5-amino-1-[(5-{2-oxa-6-azaspiro[3.3]heptane-6-carbonyl}quinolin-8-yl)methyl]-1H-pyrazolo[4,3-d]pyrimidin-7-yl}amino)hexan-1-ol | 54.8 | 91.9 | LC/MS [M + H]$^+$: 517.2<br>LC/MS RT (min)/Method: 0.96/D<br>δ 9.06 (dd, 7 = 4.2,1.7 Hz, 1H), 8.58 (dd, J = 8.5, 1.7 Hz, 1H), 7.71 (dd, J = 8.6, 4.2 Hz, 1H), 7.65-7.57 (m, 2H), 7.09 (d, J = 7.4 Hz, 1H), 6.38-6.28 (m, 2H), 6.20 (d, J = 17.0 Hz, 1H), 5.69 (s, 2H), 4.66 (dd, J = 6.9, 3.0 Hz, 2H), 4.60-4.54 (m, 2H), 4.28 (s, 2H), 4.11-4.02 (m, 2H), 3.21-3.13 (m, 2H), 1.89 (s, 1H), 1.51 (dt, J = 12.5, 6.4 Hz, 1H), 1.29 (ddt, J = 20.5, 14.3, 7.2 Hz, 2H), 1.11 (dd, J = 14.2, 6.4 Hz, 2H), 0.88 (t, J = 7.5 Hz, 2H), 0.61 (t, J = 7.3 Hz, 3H) |
| 128 | 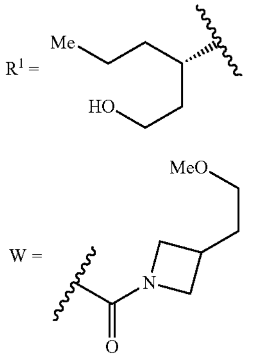<br>(3S)-3-{[5-amino-1-({5-[3-(2-methoxyethyl)azetidine-1-carbonyl]quinolin-8-yl}methyl)-1H-pyrazolo[4,3-d]pyrimidin-7-yl]amino}hexan-1-ol | 54.6 | 102.0 | LC/MS [M + H]$^+$: 533.3<br>LC/MS RT (min)/Method: 1.13<br>δ 9.06 (dd, J = 4.5, 1.6 Hz, 1H), 8.58 (d, J = 8.6 Hz, 1H), 7.72 (dd, J = 8.6, 4.2 Hz, 1H), 7.66-7.58 (m, 2H), 7.12-7.07 (m, 1H), 6.41-6.30 (m, 2H), 6.18 (d, J = 17.0 Hz, 1H), 5.74 (s, 1H), 4.26 (s, 1H), 4.18 (t, J = 9.2 Hz, 1H), 3.92 (dq, J = 18.6, 10.0, 9.3 Hz, 1H), 3.79-3.74 (m, 1H), 3.24 (t, J = 6.2 Hz, 1H), 3.20 (s, 3H), 3.13 (s, 3H), 2.66-2.59 (m,1H), 2.53 (s, 2H), 1.76 (tt, J = 14.2, 7.8 Hz, 2H), 1.53 (dt, J = 13.3, 6.3 Hz, 1H), 1.33 (dq, J = 13.9, 6.0 Hz, 1H), 1.26 (s, 1H), 1.08 (s, 1H), 0.83 (dt, J = 14.5, 7.2 Hz, 2H), 0.59 (td, J = 7.3, 2.6 Hz, 3H) |
| 129 | 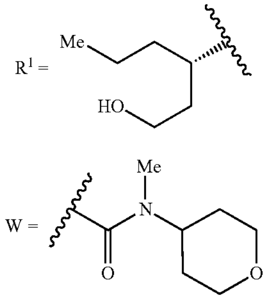<br>8-[(5-amino-7-{[(3S)-1-hydroxyhexan-3-yl]amino}-1H-pyrazolo[4,3-d]pyrimidin-1-yl)methyl]-N-methyl-N-(oxan-4-yl)quinoline-5-carboxamide | 33.7 | 83.3 | LC/MS [M + H]$^+$: 533.1<br>LC/MS RT (min)/Method: 1.31/D<br>δ 9.08 (d, J = 4.4 Hz, 1H), 8.21 (dd, J = 19.3, 8.3 Hz, 1H), 7.75-7.66 (m, 1H), 7.70 (s, 1H), 7.65 (s, 1H), 7.48 (d, J = 7.6 Hz, 1H), 7.18 (d, J = 7.3 Hz, 1H), 6.37 (d, J = 16.9 Hz, 1H), 6.20 (d, J = 17.5 Hz, 1H), 5.91 (s, 1H), 4.30 (s, 2H), 4.00-3.93 (m, 1H), 3.22 (s, 1H), 2.99 (s, 2H), 2.57 (s, 3H), 1.90 (s, 1H), 1.81 (s, 2H), 1.70 (s, 1H), 1.56 (s, 2H), 1.30 (s, 3H), 1.22-1.15 (m, 1H), 1.06 (s, 1H), 0.90 (d, J = 7.3 Hz, 2H), 0.63 (t, J = 7.4 Hz, 3H) |

TABLE A-continued

Compounds According to Formula (Ia)

| Cpd. No. | Structure ($R^5$ = H unless noted otherwise) | TLR7 Agonism $EC_{50}$ (nM) | hWB CD69 $EC_{50}$ (nM) | Analytical Data (Mass spectrum, LC/MS Retention Time, $^1H$ NMR (500 MHz, DMSO-d6)) |
|---|---|---|---|---|
| 130 | $R^1$ = 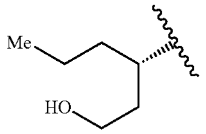<br>W = 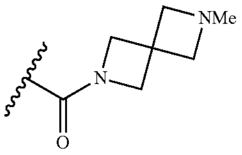<br>(3S)-3-({5-amino-1-[(5-{6-methyl-2,6-diazaspiro-[3.3]heptane-2-carbonyl}-quinolin-8-yl)methyl]-1H-pyrazolo[4,3-d]pyrimidin-7-yl}amino)hexan-1-ol | 191.3 | 49.7 | LC/MS $[M + H]^+$: 530.2<br>LC/MS RT (min)/Method: 1.11/D<br>δ 9.06 (d, J = 4.3 Hz, 1H), 8.62-8.56 (m, 1H), 7.71 (dd, J = 8.5, 4.2 Hz, 1H), 7.65-7.58 (m, 2H), 7.05 (d, J = 7.5 Hz, 1H), 6.36 (d, J = 17.1 Hz, 1H), 6.25-6.16 (m, 2H), 5.63 (s, 2H), 4.24 (s, 2H), 4.17 (s, 2H), 3.95 (q, J = 9.3 Hz, 2H), 3.48 (s, 1H), 3.31 (d, J = 7.3 Hz, 1H), 3.18 (dd, J = 13.5, 7.4 Hz, 3H), 2.15 (s, 3H), 1.89 (s, 2H), 1.52 (dt, J = 13.4, 6.5 Hz, 1H), 1.33-1.24 (m, 1H), 1.09 (dd, J = 14.0, 5.8 Hz, 1H), 0.85 (dd, J = 15.2, 7.7 Hz, 2H), 0.60 (t, J = 7.3 Hz, 3H) |
| 131 | $R^1$ = 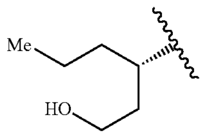<br>W = 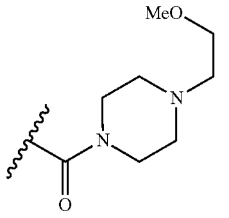<br>(3S)-3-{[5-amino-1-({5-[4-(2-methoxyethyl)piperazine-1-carbonyl]quinolin-8-yl}methyl)-1H-pyrazolo[4,3-d]pyrimidin-7-yl]amino}hexan-1-ol | 54.8 | 91.9 | LC/MS $[M + H]^+$: 562.2<br>LC/MS RT (min)/Method: 1.09/D<br>δ 9.07 (s, 1H), 8.25 (d, J = 8.3 Hz, 1H), 7.72 (dd, J = 8.6, 4.4 Hz, 1H), 7.63 (s, 1H), 7.47 (d, J = 7.2 Hz, 1H), 7.16 (s, 1H), 6.44 (s, 2H), 6.26 (s, 1H), 6.18-6.09 (m, 1H), 5.79 (s, 1H), 4.26 (s, 1H), 3.41-3.35 (m, 2H), 3.24 (s, 1H), 3.17 (s, 3H), 3.07 (s, 1H), 2.96 (s, 2H), 2.49 (s, 2H), 2.30 (s, 1H), 2.16 (s, 2H), 1.89 (s, 1H), 1.53 (s, 2H), 1.29 (s,2H), 1.14 (s, 2H), 0.90 (s, 1H) 0.82 (s, 1H), 0.67-0.53 (m, 4H) |
| 132 | $R^1$ = 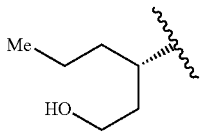<br>W = 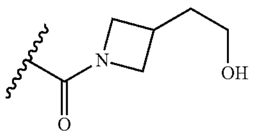<br>(3S)-3-{[5-amino-1-({5-[3-(2-hydroxyethyl)azetidine-1-carbonyl]quinolin-8-yl}me-thyl)-1H-pyrazolo[4,3-d]pyrimidin-7-yl]amino}-hexan-1-ol | 54.6 | 102.0 | LC/MS $[M + H]^+$: 519.0<br>LC/MS RT (min)/Method: 1.19/D<br>δ 9.07-9.02 (m, 1H), 8.56 (d, J = 8.6 Hz, 1H), 7.72 (dd, J = 8.6, 4.2 Hz, 1H), 7.65-7.57 (m, 2H), 7.12 (d, J = 7.9 Hz, 1H), 6.44-6.32 (m, 2H), 6.16 (d, J = 16.9 Hz, 1H), 5.78 (s, 1H), 4.25 (s, 1H), 4.19 (t, J = 9.3 Hz, 1H), 3.93 (dt, J = 17.6, 8.6 Hz, 1H), 3.79-3.65 (m, 2H), 3.57-3.46 (m, 1H), 3.33 (t, J = 6.2 Hz, 2H), 3.19 (q, J = 7.1 Hz, 2H), 2.96(s, 1H), 2.68-2.61 (m, 1H), 1.66 (s, 2H), 1.52 (dt, J = 12.6, 6.5 Hz, 1H), 1.34 (s, 1H), 1.26 (s, 1H), 1.08 (s, 1H), 0.82 (dt, J = 14.9, 7.2 Hz, 2H), 0.58 (td, J = 7.3, 2.8 Hz, 3H). |

TABLE A-continued

Compounds According to Formula (Ia)

| Cpd. No. | Structure ($R^5$ = H unless noted otherwise) | TLR7 Agonism $EC_{50}$ (nM) | hWB CD69 $EC_{50}$ (nM) | Analytical Data (Mass spectrum, LC/MS Retention Time, $^1H$ NMR (500 MHz, DMSO-d6)) |
|---|---|---|---|---|
| 133 | $R^1$ = 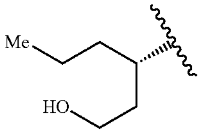<br>W = 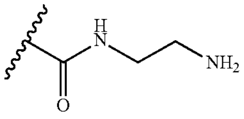<br>8-[(5-amino-7-{[(3S)-1-hydroxyhexan-3-yl]amino}-1H-pyrazolo[4,3-d]pyrimidin-1-yl)methyl]-N-(2-aminoethyl)quinoline-5-carboxamide | 408.7 | 592.8 | LC/MS $[M + H]^+$: 478.0<br>LC/MS RT (min)/Method: 1.05/D<br>δ 9.08 (d, J = 4.2 Hz, 1H), 8.80 (d, J = 8.6 Hz, 1H), 8.75 (s, 1H), 7.77-7.69 (m, 2H), 7.64 (s, 1H), 7.16 (d, J = 7.5 Hz, 1H), 6.36 (t, J = 15.9 Hz, 1H), 6.20 (d, J = 16.7 Hz, 1H), 5.64 (s, 2H), 3.22 (d, J = 6.2 Hz, 2H), 2.85 (s, 2H), 1.87 (s, 3H), 1.59- 1.52 (m, 1H), 1.48 (s, 1H), 1.37 (s, 1H), 1.29 (d, J = 10.8 Hz, 1H), 1.12 (d, J = 8.2 Hz, 1H), 0.96-0.86 (m, 2H), 0.64 (t, J = 7.3 Hz, 3H) |
| 134 | $R^1$ = 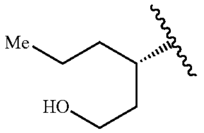<br>W = 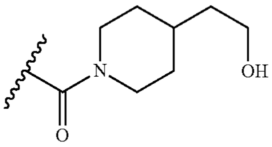<br>(3S)-3-{[5-amino-1-({5-[4-(2-hydroxyethyl)piperidine-1-carbonyl]quinolin-8-yl}methyl)-1H-pyrazolo[4,3-d]pyrimidin-7-yl]amino}hexan-1-ol | 35.4 | 193.5 | LC/MS $[M + H]^+$: 547.2<br>LC/MS RT (min)/Method: 1.26/D<br>δ 9.07 (d, J = 4.2 Hz, 1H), 8.31-8.18 (s, 1H), 7.72 (s, 1H), 7.66 (s, 1H), 7.55-7.40 (m, 1H), 7.16 (s, 1H), 6.56 (s, 1H), 6.46-6.37 (m, 1H), 6.28 (s, 1H), 6.16 (s, 1H), 5.97 (s, 1H), 4.59 (s, 1H), 3.14 (d, J = 13.7 Hz, 1H), 3.00-2.82 (m, 1H), 2.87 (s, 2H), 1.90 (s, 1H), 1.78 (d, J = 13.1 Hz, 1H), 1.63 (s, 2H), 1.45 (s, 2H), 1.33 (s, 5H), 1.17 (s, 3H), 0.93 (s, 1H), 0.85 (s, 1H), 0.66 (s, 2H), 0.60 (s,2H) |
| 135 | $R^1$ = 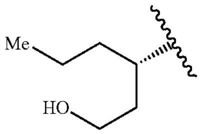<br>W = 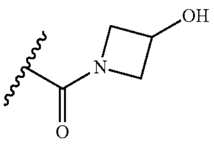<br>1-{8-[(5-amino-7-{[(3S)-1-hydroxyhexan-3-yl]amino}-1H-pyrazolo[4,3-d]pyrimidin-1-yl)methyl]quinoline-5-carbonyl}azetidin-3-ol | 125.7 | 80.1 | LC/MS $[M + H]^+$: 491.0<br>LC/MS RT (min)/Method: 1.15<br>δ 9.07 (d, J = 4.0 Hz, 1H), 8.59 (d, J = 8.5 Hz, 1H), 7.73 (dd, J = 8.5, 4.2 Hz, 1H), 7.66-7.57 (m, 2H), 7.09 (t, J = 7.4 Hz, 1H), 6.34 (tt, J = 23.2, 10.4 Hz, 2H), 6.19 (dd, J = 17.3, 5.3 Hz, 1H), 5.71 (s, 1H), 4.46 (s, 1H), 4.03 (d, J = 10.4 Hz, 1H), 3.84 (d, J = 9.9 Hz, 1H), 3.66 (s, 1H), 3.20 (s, 2H), 1.89 (s, 1H), 1.53 (d, J = 9.2 Hz, 1H), 1.34 (d, J = 6.0 Hz, 1H), 1.28 (s, 1H), 1.11 (s, 1H), 0.85 (s, 3H), 0.60 (q, J = 7.0 Hz, 3H). |

TABLE A-continued

| Compounds According to Formula (Ia) | | | | |
|---|---|---|---|---|
| Cpd. No. | Structure ($R^5$ = H unless noted otherwise) | TLR7 Agonism $EC_{50}$ (nM) | hWB CD69 $EC_{50}$ (nM) | Analytical Data (Mass spectrum, LC/MS Retention Time, $^1H$ NMR (500 MHz, DMSO-d6)) |
| 136 | $R^1$ = 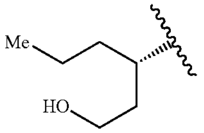<br>W = 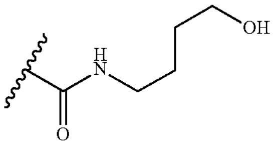<br>8-[(5-amino-7-{[(3S)-1-hydroxyhexan-3-yl]amino}-1H-pyrazolo[4,3-d]pyrimidin-1-yl)methyl]-N-(4-hydroxybutyl) quinoline-5-carboxamide | 230.5 | 418.1 | LC/MS [M + H]$^+$: 506.9<br>LC/MS RT(min)/Method: 1.20<br>δ 9.07-9.02 (m, 1H), 8.72 (d, J = 8.5 Hz, 1H), 8.55 (s, 1H), 7.70 (dd, J = 8.6, 4.2 Hz, 1H), 7.63 (t, J = 3.7 Hz, 2H), 7.16 (d, J = 7.5 Hz, 1H), 6.43-6.33 (m, 2H), 6.17 (d, J = 16.7 Hz, 1H), 5.73 (s, 1H), 4.26 (s, 1H), 3.28 (s, 1H), 3.22 (s, 2H), 1.55 (d, J = 15.8 Hz, 1H), 1.55 (s, 3H), 1.50-1.43 (m, 2H), 1.40-1.32 (m, 2H), 1.28 (s, 2H), 1.09 (d, J = 7.6 Hz, 1H), 0.88 (s, 1H), 0.82 (s, 1H), 0.61 (t, J = 7.3 Hz, 3H) |
| 137 | $R^1$ = 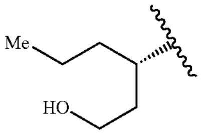<br>W = 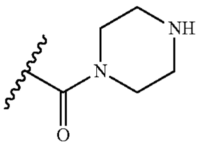<br>(3S)-3-[(5-amino-1-{[5-(piperazine-1-carbonyl) quinolin-8-yl]methyl}-1H-pyrazolo[4,3-d]pyrimidin-7-yl)amino]hexan-1-ol | 60.9 | 20.4 | LC/MS [M + H]$^+$: 504.0<br>LC/MS RT (min)/Method: 1.06/D<br>δ 9.11-9.06 (m, 1H), 8.32-8.26 (m, 1H), 7.72 (dd, J = 8.5, 4.3 Hz, 1H), 7.63 (d, J = 1.9 Hz, 1H), 7.49 (d, J = 7.4 Hz, 1H), 7.14 (s, 1H), 6.27 (s, 2H), 6.13 (s, 1H), 5.65 (s, 1H), 4.26 (s, 1H), 3.77 (s, 1H), 3.28-3.20 (m, 1H), 3.07 (s, 2H), 2.89 (s, 2H), 2.63 (s, 2H), 1.89 (d, J = 1.9 Hz, 2H), 1.53 (s, 1H), 1.40 (s, 1H), 1.28 (s, 2H), 1.14 (s, 1H), 0.95-0.76 (m, 2H), 0.61 (s, 3H). |
| 138 | $R^1$ = 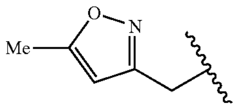<br>W = 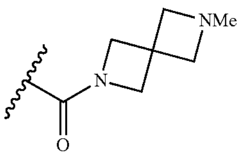<br>N7-[(5-methyl-1,2-oxazol-3-yl)methyl]-1-[(5-{6-methyl-2,6-diazaspiro[3.3]heptane-2-carbonyl}quinolin-8-yl)methyl]-1H-pyrazolo[4,3-d]pyrimidine-5,7-diamine | 274.6 | 41.7 | LC/MS [M + H]$^+$: 524.9<br>LC/MS RT (min)/Method: 1.02/D<br>δ 8.92 (dd, J = 4.1, 1.7 Hz, 1H), 8.57 (d, J = 9.1 Hz, 1H), 7.65 (dt, J = 13.4, 3.9 Hz, 3H), 7.27 (d, J = 7.3 Hz, 1H), 6.21 (s, 2H), 5.93 (s, 1H), 5.77 (s, 2H), 4.67 (d, J = 5.1 Hz, 2H), 4.17 (s, 2H), 3.19 (d, J = 7.6 Hz, 1H), 2.28 (s, 3H), 2.14 (s, 4H), 1.89 (s, 3H). |

TABLE A-continued

Compounds According to Formula (Ia)

| Cpd. No. | Structure ($R^5$ = H unless noted otherwise) | TLR7 Agonism $EC_{50}$ (nM) | hWB CD69 $EC_{50}$ (nM) | Analytical Data (Mass spectrum, LC/MS Retention Time, $^1H$ NMR (500 MHz, DMSO-d6)) |
|---|---|---|---|---|
| 139 | $R^1$ = 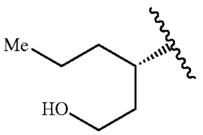<br>W = 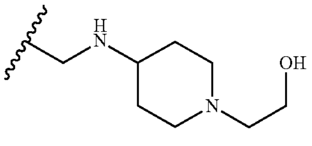<br>(3S)-3-({5-amino-1-[(5-{[4-(2-hydroxyethyl)piperazin-1-yl]methyl}quinolin-8-yl)methyl]-1H-pyrazolo[4,3-d]pyrimidin-7-yl}amino)hexan-1-ol | 5.5 | 16.2 | LC-MS $[M + H]^+$ 534.3<br>LC/MS RT (min)/Method: 1.14/D<br>δ 9.02 (dd, J = 4.3, 1.7 Hz, 1H), 8.79 (dd, J = 8.6, 1.7 Hz, 1H), 7.68 (dd, J = 8.6, 4.2 Hz, 1H), 7.60 (s, 1H), 7.44 (d, J = 7.3 Hz, 1H), 7.09 (d, J = 7.3 Hz, 1H), 6.32 (d, J = 16.7 Hz, 1H), 6.25 (d, J = 8.7 Hz, 1H), 6.11 (d, J = 16.8 Hz, 1H), 5.63 (s, 2H), 4.27-4.21 (m, 1H), 3.91-3.77 (m, 1H), 3.26-3.12 (m, 2H), 2.53 (s, 3H), 2.37 (s, 7H), 2.32 (t, J = 6.3 Hz, 2H), 1.90 (s, 4H), 1.52 (dd, J = 13.4, 6.5 Hz, 1H), 1.27 (ddd, J = 27.4, 13.2, 6.6 Hz, 2H), 1.04 (dt, J = 13.9, 7.2 Hz, 1H), 0.81 (dd, J = 14.9, 7.7 Hz, 2H), 0.58 (t, J = 7.3 Hz, 3H) |
| 140 | $R^1$ = 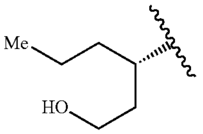<br>W = 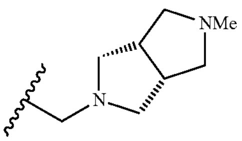<br>(3S)-3-({1-[(5-{[(3aR,6aS)-5-methyl-octahydropyrrolo [3,4-c]pyrrol-2-yl]methyl}-quinolin-8-yl)methyl]-5-amino-1H-pyrazolo[4,3-d]pyrimidin-7-yl}amino)hexan-1-ol | 8.3 | 21.1 | LC-MS $[M + H]^+$ 530.3<br>LC/MS RT (min)/Method: 1.05/D<br>δ 9.01 (dd, 7 = 4.2,1.8 Hz, 1H), 8.81 (dd, J = 8.6, 1.9 Hz, 1H), 7.66 (dd, J = 8.6, 4.1 Hz, 1H), 7.60 (d, J = 3.0 Hz, 1H), 7.45 (d, J = 7.3 Hz, 1H), 7.10 (d, J = 7.3 Hz, 1H), 6.29 (t, J = 12.4 Hz, 2H), 6.10 (d, J = 16.7 Hz, 1H), 5.61 (s, 1H), 4.25 (s, 1H), 3.91 (s, 2H), 3.24-3.13 (m, 2H), 2.41 (s, 2H), 2.20 (d, J = 6.7 Hz, 2H), 2.15-2.07 (m, 5H), 1.87 (s, 4H), 1.51 (d, J = 14.5 Hz, 1H), 1.27 (ddd, J = 35.2, 17.0, 10.2 Hz, 2H), 1.03 (dt, J = 14.4, 7.2 Hz, 1H), 0.81 (dt, J = 15.5, 7.3 Hz, 2H), 0.58 (t, J = 7.3 Hz, 3H). |
| 141 | $R^1$ = 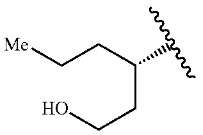<br>W = 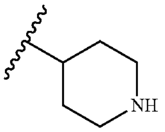<br>(3S)-3-[(5-amino-1-{[5-(piperid in-4-yl)quinolin-8-yl]methyl}-1H-pyrazolo[4,3-d]pyrimidin-7-yl)amino]hexan-1-ol | 21.7 | 0.3 | LC-MS $[M + H]^+$ 475.2<br>LC/MS RT (min)/Method: 1.14/D<br>δ 9.09-9.04 (m, 1H), 8.80 (d, J = 8.7 Hz, 1H), 7.73 (dd, J = 8.5, 4.2 Hz, 1H), 7.62 (s, 1H), 7.44 (d, J = 7.7 Hz, 1H), 7.19 (d, J = 7.7 Hz, 1H), 6.33 (d, J = 16.7 Hz, 1H), 6.14 (d, J = 16.7 Hz, 1H), 5.65 (s, 2H), 4.26 (s, 1H), 3.90 (s, 1H), 3.37 (d, J = 12.3 Hz, 1H), 3.24-3.08 (m, 2H), 1.95 (d, J = 12.9 Hz, 1H), 1.91 (s, 7H), 1.86 (s, 2H), 1.56-1.50 (m, 1H), 1.29 (d, J = 8.0 Hz, 2H), 1.06-0.98 (m, 1H), 0.82 (dd, J = 14.3, 7.0 Hz, 2H), 0.60 (t, J = 7.4 Hz, 3H) |

TABLE A-continued

Compounds According to Formula (Ia)

| Cpd. No. | Structure ($R^5$ = H unless noted otherwise) | TLR7 Agonism $EC_{50}$ (nM) | hWB CD69 $EC_{50}$ (nM) | Analytical Data (Mass spectrum, LC/MS Retention Time, $^1H$ NMR (500 MHz, DMSO-d6)) |
|---|---|---|---|---|
| 142 | $R^1$ = 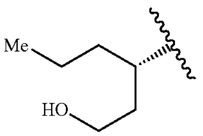 W = 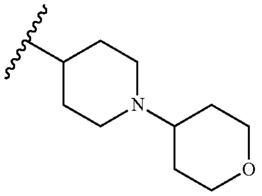 (3S)-3-{[5-amino-1-({5-[1-(oxan-4-yl)piperidin-4-yl]quinolin-8-yl}methyl)-1H-pyrazolo[4,3-d]pyrimidin-7-yl]amino}hexan-1-ol | 8.6 | | LC-MS $[M + H]^+$ 559.3<br>LC/MS RT (min)/method: 1.34/D<br>δ 9.04 (dd, J = 4.2, 1.6 Hz, 1H), 8.74 (d, J = 8.7 Hz, 1H), 7.71 (dd, J = 8.6, 4.2 Hz, 1H), 7.62 (s, 1H), 7.47 (d, J = 7.6 Hz, 1H), 7.19 (d, J = 7.6 Hz, 1H), 6.32 (d, J = 16.6 Hz, 2H), 6.11 (d, J = 16.6 Hz, 1H), 5.71 (s, 2H), 4.26 (s, 1H), 3.93 (d, J = 9.2 Hz, 2H), 3.31 (t, J = 11.6 Hz, 1H), 3.18 (t, J = 6.5 Hz, 1H), 2.67 (s, 2H), 2.60-2.50 (m, 2H), 1.91 (s, 7H), 1.81 (d, J = 12.2 Hz, 3H), 1.57-1.49 (m, 4H), 1.34-1.25 (m, 2H), 1.00 (d, J = 9.4 Hz, 1H), 0.82-0.77 (m, 2H), 0.59 (t, J = 7.3 Hz, 3H) |
| 143 | $R^1$ = 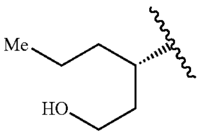 W = 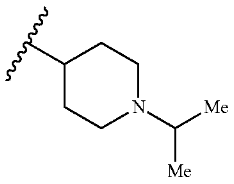 (3S)-3-{[5-amino-1-({5-[1-(propan-2-yl)piperidin-4-yl]quinolin-8-yl}methyl)-1H-pyrazolo[4,3-d]pyrimidin-7-yl]amino}hexan-1-ol | 6.1 | | LC-MS $[M + H]^+$ 517.0<br>LC/MS RT (min)/method: 1.25 |

Pharmaceutical Compositions and Administration

In another aspect, there is provided a pharmaceutical composition comprising a compound of as disclosed herein, or of a conjugate thereof, formulated together with a pharmaceutically acceptable carrier or excipient. It may optionally contain one or more additional pharmaceutically active ingredients, such as a biologic or a small molecule drug. The pharmaceutical compositions can be administered in a combination therapy with another therapeutic agent, especially an anti-cancer agent.

The pharmaceutical composition may comprise one or more excipients. Excipients that may be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., *Remington: The Science and Practice of Pharmacy,* 20th Ed. (Lippincott Williams & Wilkins 2003).

Preferably, a pharmaceutical composition is suitable for intravenous, intramuscular, subcutaneous, parenteral, spinal or epidermal administration (e.g., by injection or infusion). Depending on the route of administration, the active compound may be coated in a material to protect it from the action of acids and other natural conditions that may inactivate it. The phrase "parenteral administration" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the pharmaceutical composition can be administered via a non-parenteral route, such as a topical, epidermal or mucosal route of administration, for example, intranasally, orally, vaginally, rectally, sublingually or topically.

Pharmaceutical compositions can be in the form of sterile aqueous solutions or dispersions. They can also be formulated in a microemulsion, liposome, or other ordered structure suitable to achieve high drug concentration. The compositions can also be provided in the form of lyophilates, for reconstitution in water prior to administration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide a therapeutic response. For example, a single bolus may be administered, several divided doses may be administered over time, or the dose may be proportionally reduced or increased as indicated by the exigencies of the situation. It is especially advantageous to formulate parenteral compositions in dosage unit form for ease of administration and uniformity of dosage. "Dosage unit form" refers to physically discrete units suited as unitary dosages for the subjects to be treated; each unit containing a predetermined quantity of active compound calculated to produce the desired therapeutic response, in association with the required pharmaceutical carrier.

The dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg, or alternatively 0.1 to 5 mg/kg. Exemplary treatment regimens are administration once per week, once every two weeks, once every three weeks, once every four weeks, once a month, once every 3 months, or once every three to 6 months. Preferred dosage regimens include 1 mg/kg body weight or 3 mg/kg body weight via intravenous administration, using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 μg/mL and in some methods about 25-300 μg/mL.

A "therapeutically effective amount" of a compound of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective amount" preferably inhibits tumor growth by at least about 20%, more preferably by at least about 40%, even more preferably by at least about 60%, and still more preferably by at least about 80% relative to untreated subjects. A therapeutically effective amount of a therapeutic compound can decrease tumor size, or otherwise ameliorate symptoms in a subject, which is typically a human but can be another mammal. Where two or more therapeutic agents are administered in a combination treatment, "therapeutically effective amount" refers to the efficacy of the combination as a whole, and not each agent individually.

The pharmaceutical composition can be a controlled or sustained release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., *Sustained and Controlled Release Drug Delivery Systems*, J. R. Robinson, ed., Marcel Dekker, Inc., New York, 1978.

Therapeutic compositions can be administered via medical devices such as (1) needleless hypodermic injection devices; (2) microinfusion pumps; (3) transdermal devices; (4) infusion devices; and (5) osmotic devices.

In certain embodiments, the pharmaceutical composition can be formulated to ensure proper distribution in vivo. For example, to ensure that the therapeutic compounds of the invention cross the blood-brain barrier, they can be formulated in liposomes, which may additionally comprise targeting moieties to enhance selective transport to specific cells or organs.

Industrial Applicability and Uses

TLR7 agonist compounds disclosed herein can be used for the treatment of a disease or condition that can be ameliorated by activation of TLR7.

In one embodiment, the TLR7 agonist is used in combination with an anti-cancer immunotherapy agent—also known as an immuno-oncology agent. An anti-cancer immunotherapy agent works by stimulating a body's immune system to attack and destroy cancer cells, especially through the activation of T cells. The immune system has numerous checkpoint (regulatory) molecules, to help maintain a balance between its attacking legitimate target cells and preventing it from attacking healthy, normal cells. Some are stimulators (up-regulators), meaning that their engagement promotes T cell activation and enhances the immune response. Others are inhibitors (down-regulators or brakes), meaning that their engagement inhibits T cell activation and abates the immune response. Binding of an agonistic immunotherapy agent to a stimulatory checkpoint molecule can lead to the latter's activation and an enhanced immune response against cancer cells. Reciprocally, binding of an antagonistic immunotherapy agent to an inhibitory checkpoint molecule can prevent down-regulation of the immune system by the latter and help maintain a vigorous response against cancer cells. Examples of stimulatory checkpoint molecules are B7-1, B7-2, CD28, 4-1BB (CD137), 4-1BBL, ICOS, CD40, ICOS-L, OX40, OX40L, GITR, GITRL, CD70, CD27, CD40, DR3 and CD28H. Examples of inhibitory checkpoint molecules are CTLA-4, PD-1, PD-L1, PD-L2, LAG-3, TIM-3, Galectin 9, CEACAM-1, BTLA, CD69, Galectin-1, CD113, GPR56, VISTA, 2B4, CD48, GARP, PD1H, LAIR1, TIM-1, CD96 and TIM-4.

Whichever the mode of action of an anti-cancer immunotherapy agent, its effectiveness can be increased by a general up-regulation of the immune system, such as by the activation of TLR7. Thus, in one embodiment, this specification provides a method of treating a cancer, comprising administering to a patient suffering from such cancer a therapeutically effective combination of an anti-cancer immunotherapy agent and a TLR7 agonist as disclosed herein. The timing of administration can be simultaneous, sequential, or alternating. The mode of administration can systemic or local. The TLR7 agonist can be delivered in a targeted manner, via a conjugate.

Cancers that could be treated by a combination treatment as described above include acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, bile duct cancer, endometrial cancer, ependymoma, esophageal cancer, esthesioneuroblastoma, Ewing sarcoma, eye cancer, fallopian tube cancer, gallbladder cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, testicular cancer, throat cancer, thyroid cancer, urethral cancer, uterine cancer, vaginal cancer, and vulvar cancer.

Anti-cancer immunotherapy agents that can be used in combination therapies as disclosed herein include: AMG 557, AMP-224, atezolizumab, avelumab, BMS 936559, cemiplimab, CP-870893, dacetuzumab, durvalumab, enoblituzumab, galiximab, IMP321, ipilimumab, lucatumumab, MEDI-570, MEDI-6383, MEDI-6469, muromonab-CD3, nivolumab, pembrolizumab, pidilizumab, spartalizumab, tremelimumab, urelumab, utomilumab, varlilumab, vonlerolizumab. Table B below lists their alternative name(s) (brand name, former name, research code, or synonym) and the respective target checkpoint molecule.

TABLE B

| Immunotherapy Agent | Alternative Name(s) | Target |
|---|---|---|
| AMG 557 | | B7RP-1 (ICOSL) |
| AMP-224 | | PD-1 |
| Atezolizumab | MPDL3280A, RO5541267, TECENTRIQ ® | PD-L1 |
| Avelumab | BAVENCIO ® | PD-L1 |
| BMS 936559 | | PD-L1 |
| Cemiplimab | LIBTAYO ® | PD-1 |
| CP-870893 | | CD40 |
| Dacetuzumab | | CD40 |
| Durvalumab | IMFINZI ® | PD-L1 |
| Enoblituzumab | MGA271 | B7-H3 |
| Galiximab | | B7-1 (CD80) |
| IMP321 | | LAG-3 |
| Ipilimumab | YERVOY ® | CTLA-4 |
| Lucatumumab | | CD40 |
| MEDI-570 | | ICOS (CD278) |
| MEDI-6383 | | OX40 |
| MEDI-6469 | | OX40 |
| Muromonab-CD3 | | CD3 |
| Nivolumab | OPDIVO ® | PD-1 |
| Pembrolizumab | KEYTRUDA ® | PD-1 |
| Pidilizumab | MDV9300 | PD-1 |
| Spartalizumab | PDR001 | PD-1 |
| Tremelimumab | Ticilimumab, CP-675, CP-675, 206 | CTLA-4 |
| Urelumab | BMS-663513 | CD137 |
| Utomilumab | PF-05082566 | CD137 |
| Varlilumab | CDX 1127 | CD27 |
| Vonlerolizumab | RG7888, MOXR0916, pogalizumab | OX40 |

In one embodiment of a combination treatment with a TLR7 agonist, the anti-cancer immunotherapy agent is an antagonistic anti-CTLA-4, anti-PD-1, or anti-PD-L1 antibody. The cancer can be lung cancer (including non-small cell lung cancer), pancreatic cancer, kidney cancer, head and neck cancer, lymphoma (including Hodgkin's lymphoma), skin cancer (including melanoma and Merkel skin cancer), urothelial cancer (including bladder cancer), gastric cancer, hepatocellular cancer, or colorectal cancer.

In another embodiment of a combination treatment with a TLR7 agonist, the anti-cancer immunotherapy agent is an antagonistic anti-CTLA-4 antibody, preferably ipilimumab.

In another embodiment of a combination treatment with a TLR7 agonist, the anti-cancer immunotherapy agent is an antagonistic anti-PD-1 antibody, preferably nivolumab or pembrolizumab.

The TLR7 agonists disclosed herein also are useful as vaccine adjuvants.

The practice of this invention can be further understood by reference to the following examples, which are provided by way of illustration and not of limitation.

Analytical Procedures

NMR

The following conditions were used for obtaining proton nuclear magnetic resonance (NMR) spectra: NMR spectra were taken in either 400 Mz or 500 Mhz Bruker instrument using either DMSO-d6 or $CDCl_3$ as solvent and internal standard. The crude NMR data was analyzed by using either ACD Spectrus version 2015-01 by ADC Labs or MestReNova software.

Chemical shifts are reported in parts per million (ppm) downfield from internal tetramethylsilane (TMS) or from the position of TMS inferred by the deuterated NMR solvent. Apparent multiplicities are reported as: singlet-s, doublet-d, triplet-t, quartet-q, or multiplet-m. Peaks that exhibit broadening are further denoted as br. Integrations are approximate. It should be noted that integration intensities, peak shapes, chemical shifts and coupling constants can be dependent on solvent, concentration, temperature, pH, and other factors. Further, peaks that overlap with or exchange with water or solvent peaks in the NMR spectrum may not provide reliable integration intensities. In some cases, NMR spectra may be obtained using water peak suppression, which may result in overlapping peaks not being visible or having altered shape and/or integration.

Liquid Chromatography

The following preparative and/or analytical liquid chromatography methods were used:

Preparative HPLC/MS Method A: Column: XBridge C18, 200 mm×19 mm, 5-μm particles; Mobile Phase A: 5:95 acetonitrile: water with 0.05% TFA; Mobile Phase B: 95:5 acetonitrile: water with 0.05% TFA; Gradient: 0-47% B over 20 minutes, then a 0-minute hold at 100% B; Flow Rate: 20 mL/min; Column Temperature: 25° C.

Preparative HPLC/MS Method B: Column: XBridge C18, 150 mm×19 mm, 5-μm particles; Mobile Phase A: water with 0.05% TFA; Mobile Phase B: acetonitrile with 0.05% TFA; Gradient: a 2-minute hold at 10% B, 10-100% B over 20 minutes, then a 3-minute hold at 100% B; Flow Rate: 19 mL/min; Column Temperature: 25° C.

Preparative HPLC/MS Method C: Column: XBridge C18, 200 mm×19 mm, 5-am particles; Mobile Phase A: 5:95 acetonitrile: water with 10 mM ammonium acetate; Mobile Phase B: 95:5 acetonitrile: water with 10 mM 5 ammonium acetate; Gradient: 1-65% B over 20 minutes, then a 0-minute hold at 100% B; Flow rate: 20 mL/min; Column Temperature: 25° C.

Analytical LC/MS Method D: Column: Waters XBridge C18, 2.1 mm×50 mm, 1.7 am particles; Mobile Phase A: 5:95 acetonitrile: water with 0.1% TFA; Mobile Phase B: 95:5 acetonitrile: water 0.1% TFA; Temperature: 50° C.; Gradient: 0% B to 100% B over 3 min, then a 0.50 min hold at 100% B; Flow: 1 mL/min; Detection: MS and UV (220 nm).

Analytical LC/MS Method E: Column: Acquity UPLC BEH C18, 2.1 mm×50 mm, 1.7 am particles; Mobile Phase A: water with 0.1% formic acid; Mobile Phase B: acetonitrile with 0.1% formic acid; Temperature: 40° C.; Gradient: a 0.2 min hold at 5% B; 5% B to 95% B over 2.3 min, then a 0.20 min hold at 95% B; Flow: 1 mL/min; Detection: UV (254 nm & 220 nm).

Analytical LC/MS Method F: Column: Acquity UPLC BEH C18, 2.1 mm×50 mm, 1.7 am particles; Mobile Phase A: water with 0.1% formic acid; Mobile Phase B: acetonitrile with 0.1% formic acid; Temperature: 40° C.; Gradient: a 0.2 min hold at 50% B; 50% B to 95% B over 2.3 min, then a 0.20 min hold at 95% B; Flow: 1 mL/min; Detection: UV (254 nm & 220 nm).

Synthesis—General Procedures

Generally, the procedures disclosed herein produce a mixture of regioisomers, alkylated at the 1H or 2H position of the pyrazolopyrimidine ring system (which are also referred to as N1 and N2 regioisomers, respectively, alluding to the nitrogen that is alkylated). For brevity, the N2 regioisomers are not shown, but it is to be understood that they are present in the initial product mixture and separated at a later time, for example by preparative HPLC.

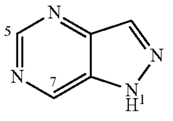

1H-pyrazolo[4,3-d]pyrimidine

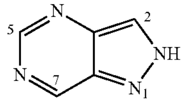

2H-pyrazolo[4,3-d]pyrimidine

The mixture of regioisomers can be separated at an early stage of the synthesis and the remaining synthetic steps carried out with the 1H regioisomer or, alternatively, the synthesis can be progressed carrying the mixture of regioisomers and separation effected at a later stage, as desired.

The compounds of the present disclosure can be prepared by a number of methods well known to one skilled in the art of synthetic organic chemistry. These methods include those described below, or variations thereof. Preferred methods include, but are not limited to, those described below in the Schemes below. The Schemes are intended to be generic, but in some instances a feature may be depicted specifically (e.g., a methyl ester or particular regioisomer) as a matter of convenience.

Scheme 1

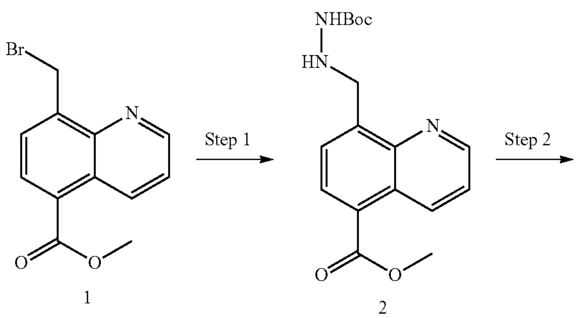

1 2

-continued

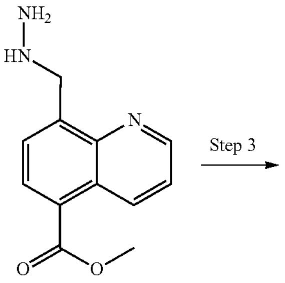

3

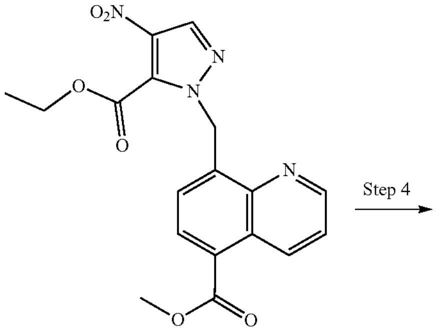

4

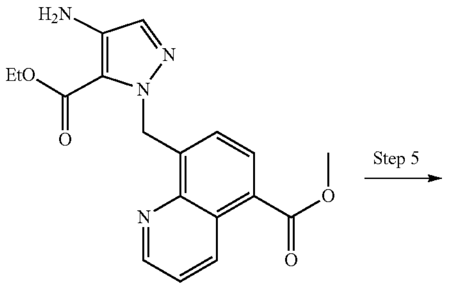

5

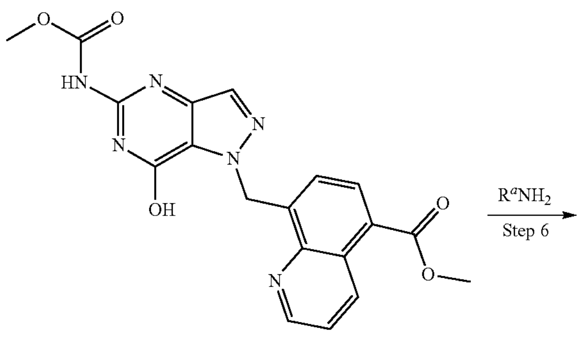

6

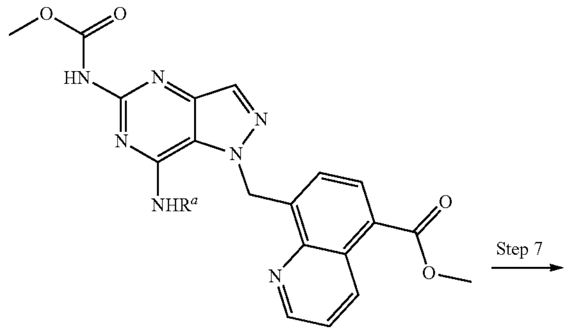

7

-continued

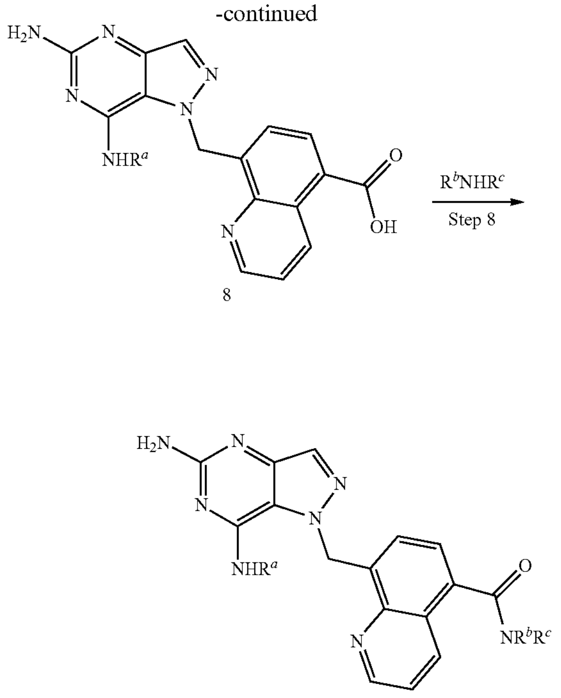

8

9

$R^a$ can be, in Scheme 1 and other occurrences thereof, for example,

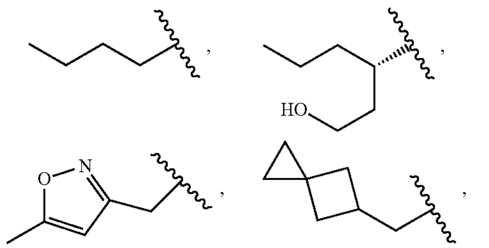

or other suitable moiety. $R^bNHR^c$ is, in Scheme 1 and other occurrences thereof, a primary or secondary amine. $R^a$, $R^b$, and/or $R^c$ can have functional groups masked by protecting group that is removed at the appropriate time during the synthetic process.

Compound 9 can be prepared by a synthetic sequence outlined in Scheme 1. Quinoline 1 (CAS Reg. No. 82867-40-6) is converted to hydrazine intermediate 2 with BOC protected hydrazine. After treatment with hydrochloric acid, intermediate 3 is obtained. Intermediate 4 is obtained by mixing ethyl-2-chloro-2-oxoacetate and (Z)—N,N-dimethyl-2-nitroethen-1-amine, and then adding intermediate 3. Intermediate 4 is converted to intermediate 5 by reducing the nitro group to an amine group with zinc. By treating intermediate 5 with 1,3-bis(methoxycarbonyl)-2-thioseudourea with acetic acid and then sodium methoxide, intermediate 6 is obtained. Intermediate 7 is synthesized by reaction of intermediate 6 with $R^aNH_2$ in the presence of BOP and DBU. After hydroxylation with NaOH, intermediate 8 is obtained. In the last step of Scheme 1, compound 9 is prepared by amide coupling with $R^bNHR^c$.

Scheme 2

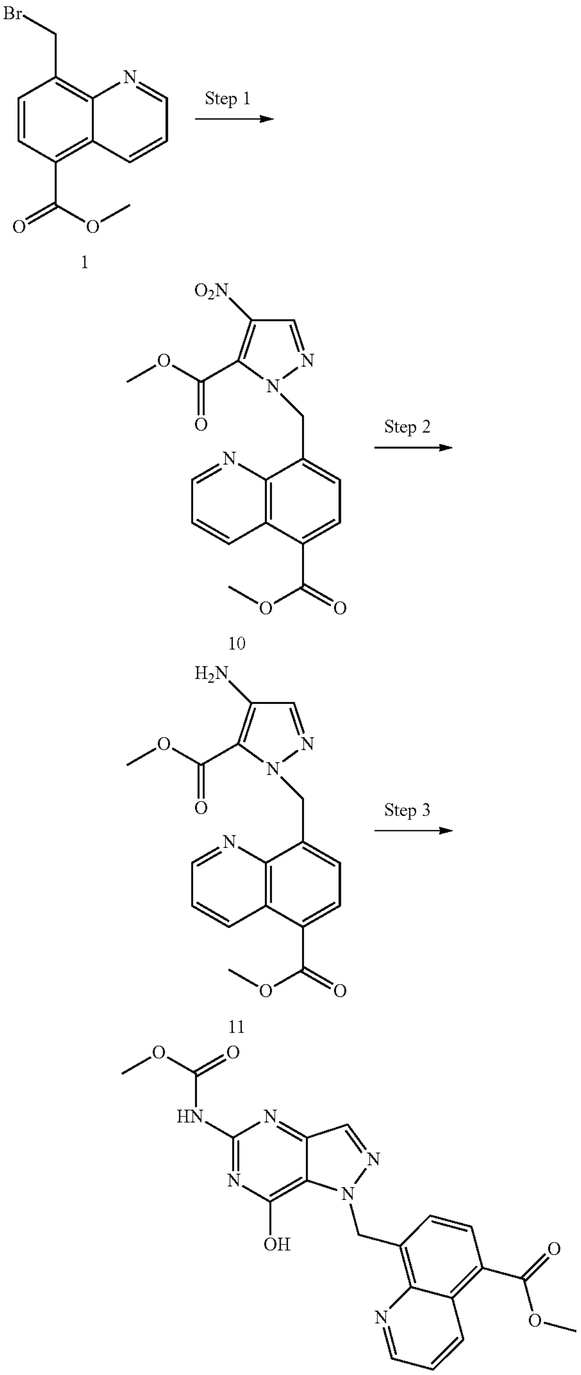

1

10

11

6

Scheme 2 above shows an alternative method for the preparation of intermediate 6, by coupling quinoline 1 and methyl 4-nitro-1H-pyrazole-5-carboxylate (CAS Reg. No. 138786-86-9) to form intermediate 10. Intermediate 11 is obtained by reducing the nitro group of intermediate 10 to an amine group with zinc. Intermediate 6 is obtained by treating intermediate 11 with 1,3-bis(methoxycarbonyl)-2-thiopseudourea with acetic acid and then sodium methoxide, as shown in Step 3 of Scheme 2.

Scheme 3
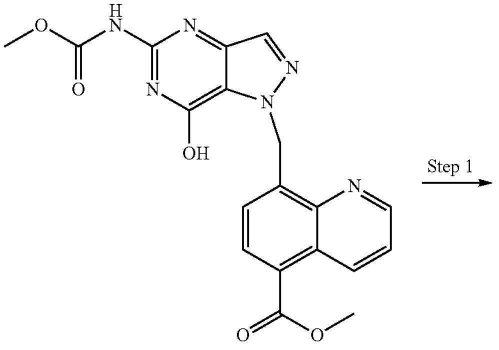
6
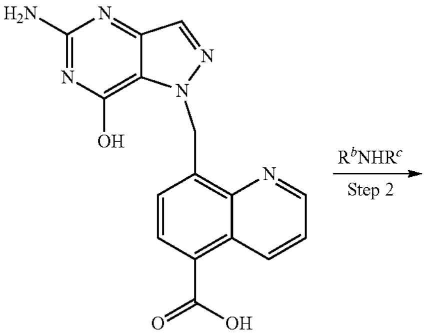
12
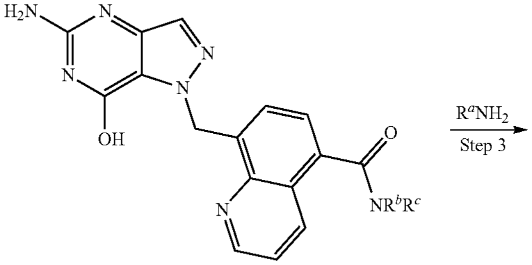
13
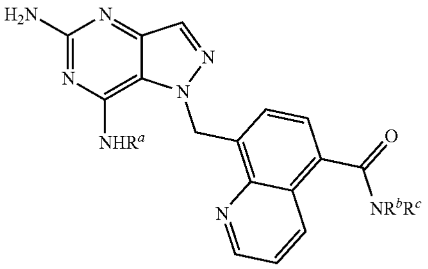
9
Scheme 3 above shows an alternative method for preparing compound 9, by hydroxylation of intermediate 6 to form acid 12. After amide coupling, intermediate 13 is obtained. In the last step, compound 9 is obtained by treating intermediate 13 with $R^aNH_2$ in the presence of BOP and DBU.
Scheme 4
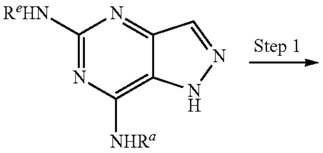
14
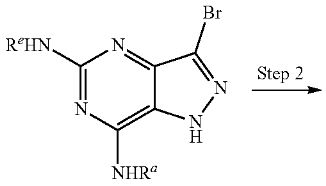
15
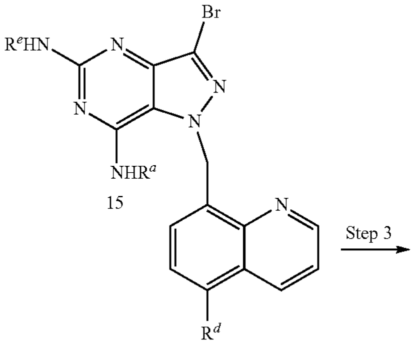
15
16
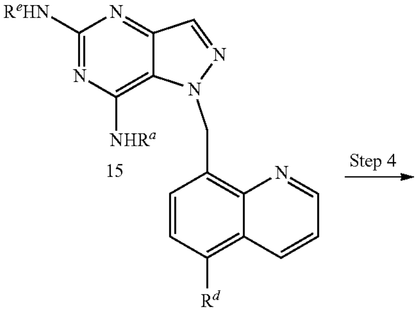
15
17
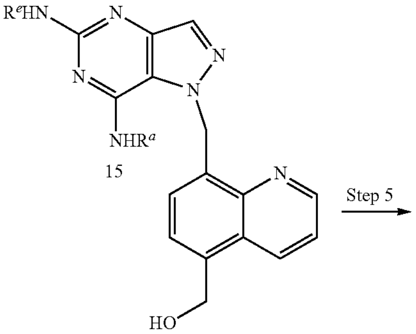
15
18

-continued

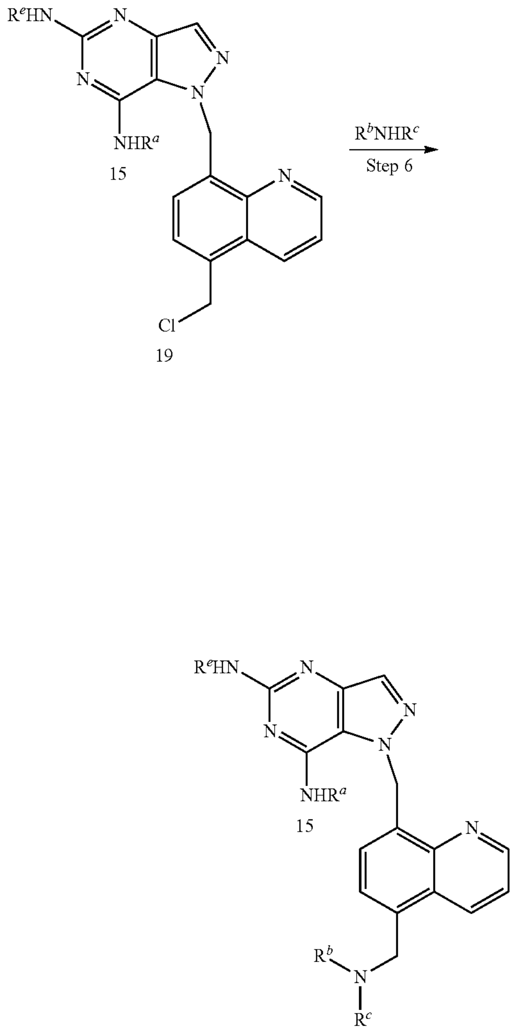

15

19

15

20

$R^d$ is, in Scheme 4 and other occurrences thereof, for example, H, F, $CO_2Me$ (or Et), or cyano. $R^e$ is, in Scheme 4 and other occurrences thereof, for example, H or $CO_2Me$ (or Et) or a protecting group.

The method of Scheme 4 above can be used to to prepare compound 20. Bromination of compound 14 with NBS (N-bromosuccinimide) forms intermediate 15. Intermediate 16 is obtained by coupling intermediate 15 with a quinoline compound where $R^d$ is a carboxylate ester. (We have observed that having a bromine at the $C_3$ position generally leads to a higher N1/N2 ratio in the product mixture.) The bromine group of intermediate 16 is removed by catalytic hydrogenation to afford intermediate 17. The carboxylic ester in intermediate 17 is reduced with $LiAlH_4$ or $LiBH_4$ to generate intermediate 18. Intermediate 19 is obtained by treating intermediate 18 with thionyl chloride. Compound 20 is obtained by treating with an amine $R^bNHR^c$. If $R^e$ comprises a carbamate or other protecting group, the latter may be removed at this stage with sodium hydroxide or appropriate deprotecting reagent.

Scheme 5

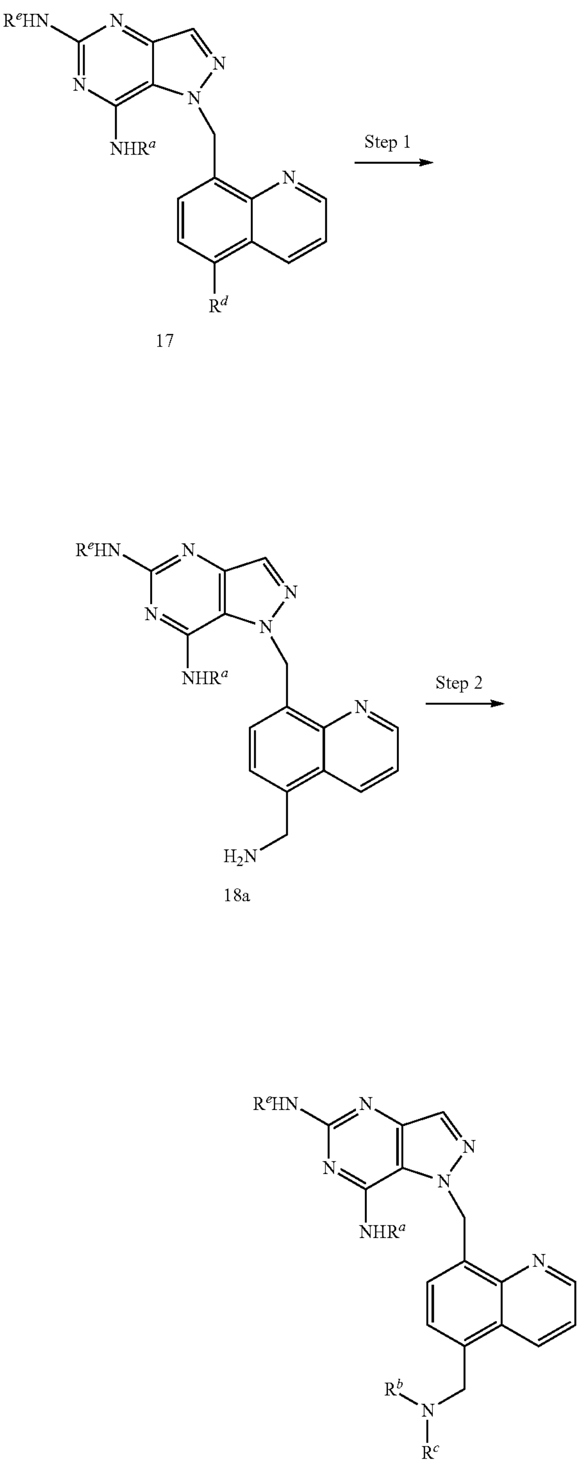

17

18a

20

Scheme 5 above shows an alternative method for the preparation of compound 20 by reductive amination. Intermediate 17 is reduced to amine 18a (in the instance in which $R^d$ is a cyano group). Amine 18a is then subjected to reductive amination with a corresponding ketone to form compound 20.

Scheme 6

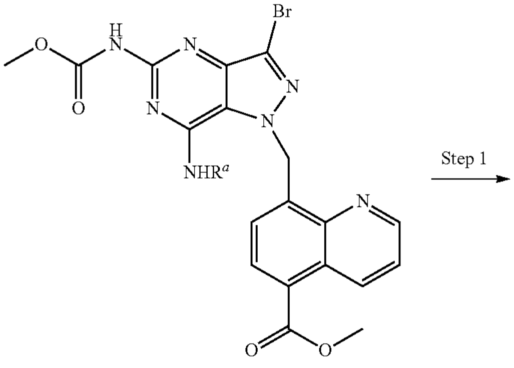

19

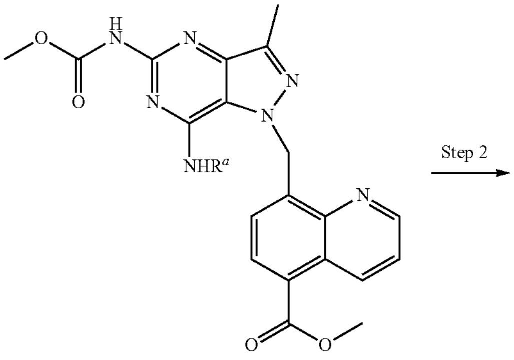

21

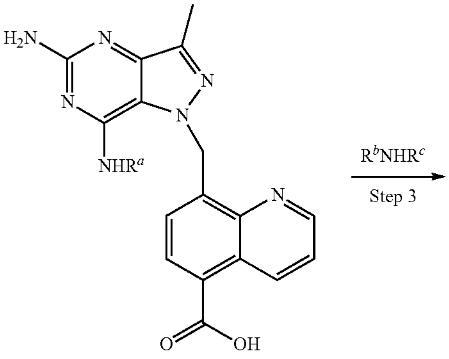

21

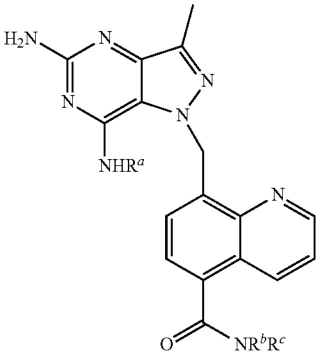

23

Scheme 6 above shows a method for the preparation of compound 23. Starting with intermediate 19 (where $R^d$ is carboxylic ester and $R^e$ is carbamate protecting group), methylation can be effected by treating intermediate 19 with 2,4,6-trimethyl-1,3,5,2,4,6-trioxatriborinane and $PdCl_2$ (dppf)-$CH_2Cl_2$ adduct to afford intermediate 21. After hydrolysis with sodium hydroxide, intermediate 22 is obtained. In the final step, compound 23 is obtained by amide formation of intermediate 22 with $R^bNHR^c$.

Scheme 7

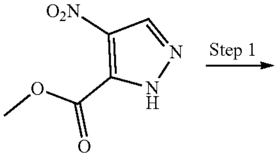

24

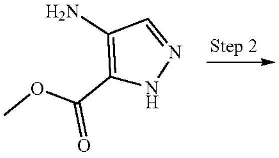

25

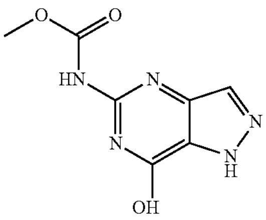

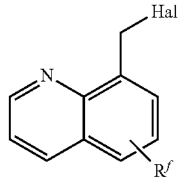

27

Step 3

26

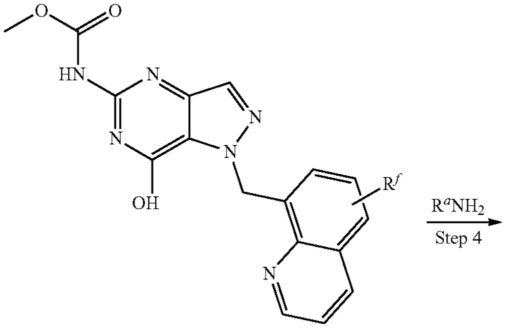

28

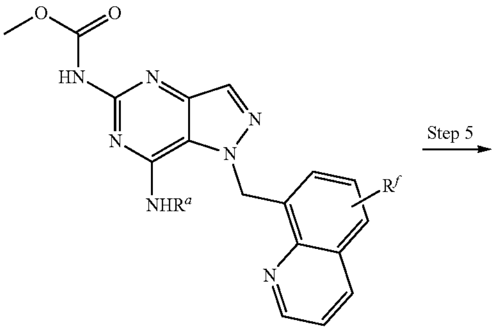

29

-continued

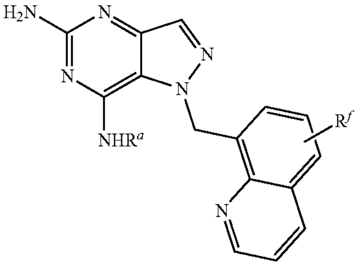

30

$R^f$ is, in Scheme 7 and other occurrences thereof, an amide or amine moiety and Hal is halogen, such as Cl or Br.

Compound 30 can be prepared the method of Scheme 7 above, by coupling a pyrazolopyrimidine core and a quinoline moiety. The nitro group of starting material 24 is reduced to an amine group of compound 25. Pyrazolopyrimidine 26 is obtained by treating intermediate 25 with 1,3-bis(methoxycarbonyl)-2-thiopseudourea with acetic acid and then sodium methoxide. Quinoline compound 27 is prepared similarly to the reactions described in other Schemes hereinabove. The coupling of pyrazolopyrimidine 26 with quinoline 27 affords intermediate 28. Intermediate 29 is obtained by treating intermediate 28 with amine $R^aNH_2$ in the presence of BOP and DBU. In the last step, carbamate protecting group of intermediate 29 is removed with sodium hydroxide to generate compound 30.

Scheme 8

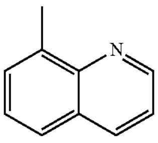

31

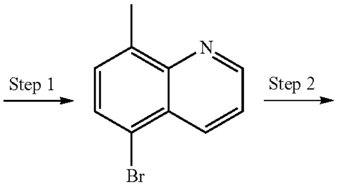

32

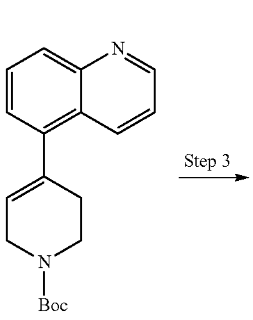

33

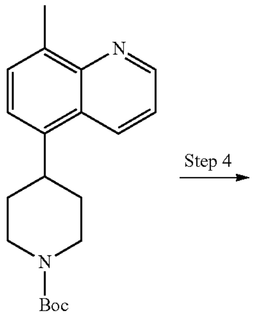

34

-continued

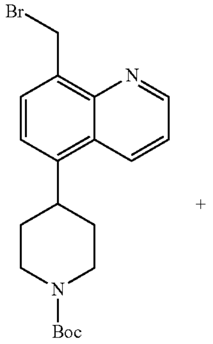

35

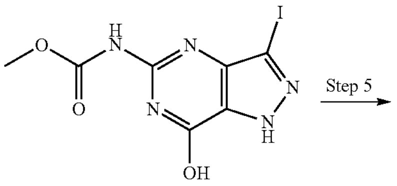

36

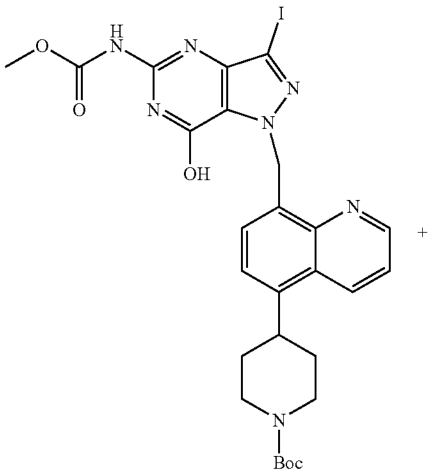

37

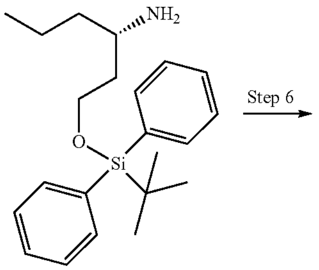

38

-continued

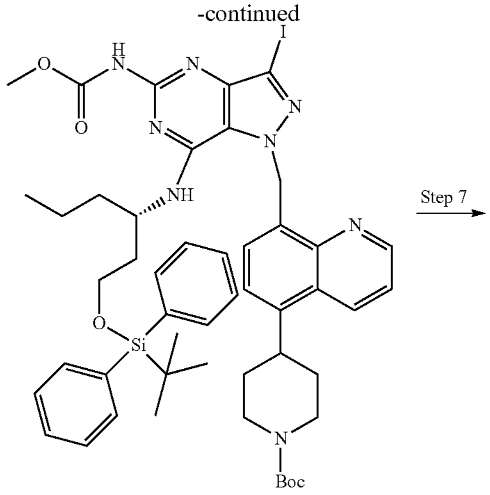

39

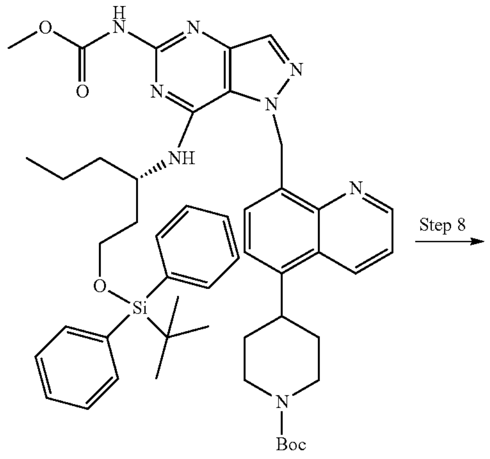

40

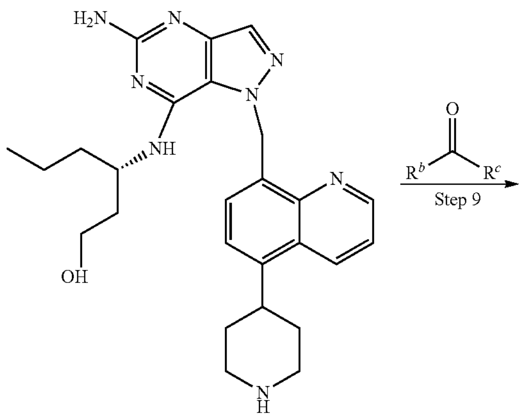

41

-continued

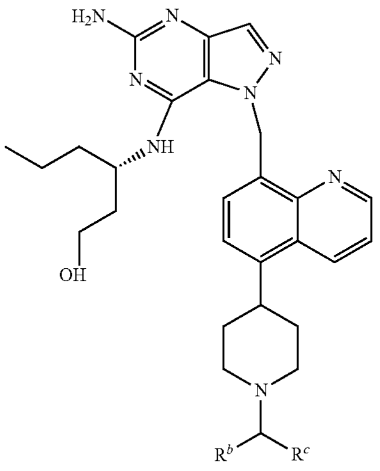

42

Scheme 8 above shows how compounds where W is

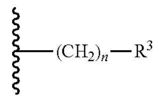

with n equals 0 can be made.

Starting material 31 (CAS Reg. No. 611-32-5) is converted to intermediate 32 by bromination. After coupling with tert-butyl 4-(3,3,4,4-tetramethylborolan-1-yl)-3,6-dihydropyridine-1(2H)-carboxylate, intermediate 33 is obtained. Intermediate 34 is obtained by hydrogenation. After treated with NBS and AIBN, Intermediate 35 is obtained. Intermediate 37 is obtained by mixing intermediate 35 and 36 with base. By coupling with intermediate 38, Intermediate 37 is converted to intermediate 39. Iodo group of intermediate 39 is removed by reduction to form intermediate 40. By hydrolysis with Sodium Hydroxide and acids, Compound 41 is obtained. Compound 42 is obtained by reductive amination of Compound 41 with a ketone $R^bR^c(=O)$.

Synthesis—Specific Examples

To further illustrate the foregoing, the following non-limiting, the following exemplary synthetic schemes are included. Variations of these examples within the scope of the the claims are within the purview of one skilled in the art and are considered to fall within the scope of this disclosure. The reader will recognize that the skilled artisan, provided with the present disclosure and skilled in the relevant art, will be able to prepare and use the compounds disclosed herein without exhaustive examples.

Analytical data for compounds numbered 100 and higher are found in Table A.

Example 1—Compound 111

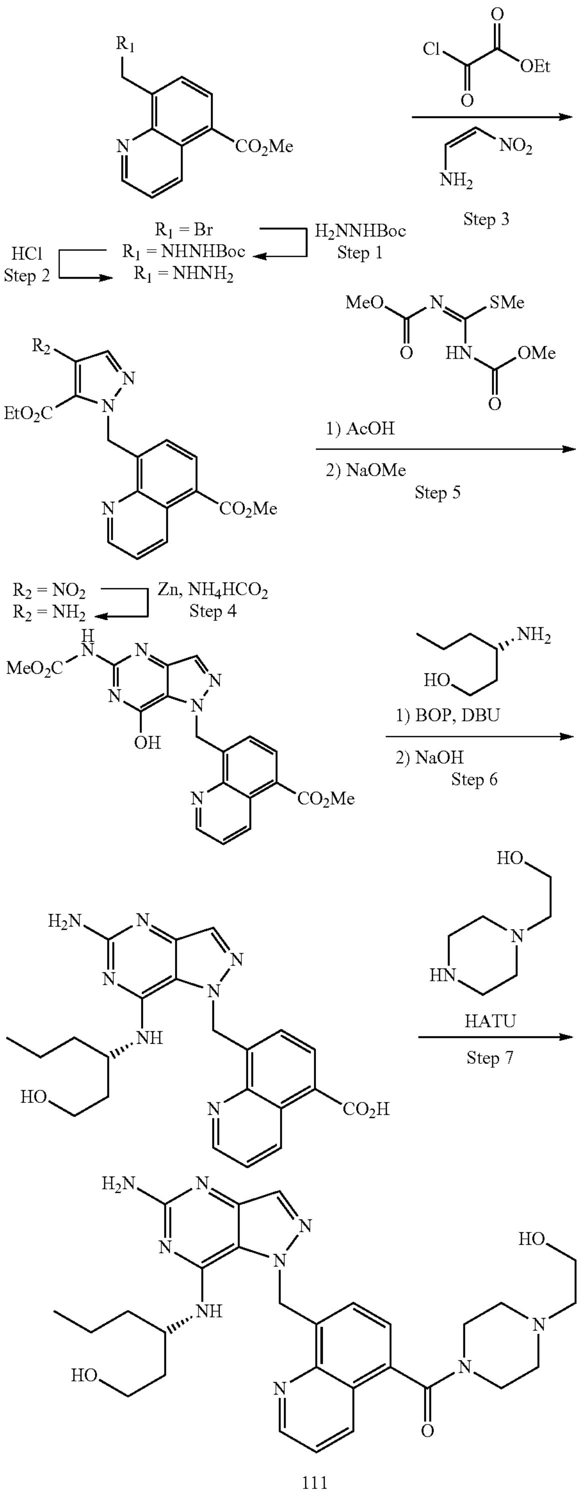

111

Step 1. TEA (1.493 mL, 10.71 mmol) was added to a solution of methyl 8-(bromo-methyl)quinoline-5-carboxylate (1 g, 3.57 mmol), tert-butyl hydrazinecarboxylate (2.359 g, 17.85 mmol) in DMF (4 mL). The reaction mixture was stirred at 75° C. for 4 h, diluted with 100 mL of water, and extracted with EtOAc (3×75 mL). The organic phases were combined, concentrated and purified by column chromatography: Column: 40 g CombiFlash column; Mobile Phase A: hexanes; Mobile Phase B: ethyl acetate; Gradient: a 1 min hold at 0% B, 0-50% B over 14 min, then a 3 min hold at 100% B; Flow Rate: 40 mL/min; Column Temperature: 25° C. The fractions containing expected product were combined, concentrated and dried under high vacuum for 1 h. to yield methyl 8-((2-(tert-butoxycarbonyl)hydrazineyl)methyl)quinoline-5-carboxylate (0.71 g, 60.0% yield).

LC-MS m/z 332.2 $[M+H]^+$; Retention Time: 1.61 min (Method E).

Step 2. HCl in dioxane (5.36 mL, 21.43 mmol) was added to a solution of methyl 8-((2-(tert-butoxycarbonyl)hydrazineyl)methyl)quinoline-5-carboxylate (0.71 g, 2.143 mmol) in MeOH (10 mL). The reaction mixture was stirred at RT overnight, after which it turned into a slurry. The precipitate was collected by filtration and dried under high vacuum for 1 h to yield the HCl salt of methyl 8-(hydrazineylmethyl)quinoline-5-carboxylate (0.58 g, 1.705 mmol, 79.6% yield).

LC-MS m/z 232.1 $[M+H]^+$; Retention Time: 1.05 min (Method E).

Step 3. A solution of (Z)—N,N-dimethyl-2-nitroethen-1-amine (1.528 g, 13.16 mmol) in DCM (26 mL) and pyridine (17.49 mL, 216 mmol) was cooled to −10° C. Ethyl 2-chloro-2-oxoacetate (2.226 mL, 19.89 mmol) was added slowly. The reaction mixture was warmed to RT over 2 h and stirred at RT overnight. The reaction mixture was concentrated to 20 mL. Methyl 8-(hydrazineylmethyl)quinoline-5-carboxylate HCl salt (1 g, 4.32 mmol) was added. The resultant mixture was stirred at RT for 2 h. The reaction mixture was concentrated and purified by reverse phase column chromatography: Column: 50 g CombiFlash Aq column; Mobile Phase A: water with 0.05 TFA; Mobile Phase B: acetonitrile with 0.05% TFA; Gradient: a 1 min hold at 0% B, 0-50% B over 12 min, then a 3 min hold at 100% B; Flow Rate: 40 mL/min; Column Temperature: 25° C. The fractions containing the expected product were combined and freeze-dried to yield methyl 8-((5-(ethoxycarbonyl)-4-nitro-1H-pyrazol-1-yl)methyl)quinoline-5-carboxylate (627 mg, 1.633 mmol, 37.8% yield) as a solid.

LC-MS m/z 385.2 $[M+H]^+$; Retention Time: 2.22 min (Method E).

Step 4. Zinc (358 mg, 5.48 mmol) was added to a solution of methyl 8-((5-(ethoxycarbonyl)-4-nitro-1H-pyrazol-1-yl)methyl)quinoline-5-carboxylate (421 mg, 1.095 mmol) and ammonium formate (691 mg, 10.95 mmol) in MeOH (3 mL) and THF (5 mL). The reaction mixture was stirred at RT for 1 h. LCMS analysis showed the reaction was complete. The reaction mixture was filtered, concentrated, and freeze-dried with acetonitrile and water to yield crude methyl 8-((4-amino-5-(ethoxycarbonyl)-1H-pyrazol-1-yl)methyl)quinoline-5-carboxylate (285 mg, 0.804 mmol, 73.5%).

LC-MS m/z 355.2 $[M+H]^+$; Retention Time: 1.83 min (Method E).

Step 5. Acetic acid (0.64623 mL, 11.28 mmol) and TFA (0.07 mL) were added to a mixture of 1,3-bis(methoxycarbonyl)-2-methyl-2-thiopseudourea (279 mg, 1.355 mmol) and methyl 8-((4-amino-5-(ethoxycarbonyl)-1H-pyrazol-1-yl)methyl)quinoline-5-carboxylate (400 mg, 1.129 mmol) in MeOH (20 mL). The reaction mixture was stirred at RT overnight. LCMS analysis showed conversion to an intermediate (LC-MS m/z 513.3 $[M+H]^+$). NaOMe (4.2 mL, 33.87 mmol) was added. The reaction mixture stirred at RT for 1 h. Acetic acid was added to adjust the pH to 5. The product was collected by filtration and dried under high vacuum for overnight to yield methyl 8-((7-hydroxy-5-((methoxycarbonyl)amino)-1H-pyrazolo[4,3-d]pyrimidin-1-yl)methyl)quinoline-5-carboxylate (313 mg, 0.765 mmol, 67.9% yield).

LC-MS m/z 409.2 $[M+H]^+$; Retention Time: 1.67 min (Method E).

Step 6. ((1H-Benzo[d][1,2,3]triazol-1-yl)oxy)tris(dimethylamino)phosphonium hexafluorophosphate(V) (401 mg, 0.906 mmol) was added to a solution of methyl 8-((7-hydroxy-5-((methoxycarbonyl)amino)-1H-pyrazolo[4,3-d]pyrimidin-1-yl)methyl)quinoline-5-carboxylate (185 mg, 0.453 mmol), (S)-3-aminohexan-1-ol (HCl salt, 348 mg, 2.265 mmol) and 2,3,4,6,7,8,9,10-octahydropyrimido[1,2-a]azepine (0.305 mL, 2.039 mmol) in DMSO (1.5 mL). The reaction mixture was stirred at 70° C. overnight and worked up with EtOAc, brine, and water. The combined organic phases were concentrated and dried under high vacuum to yield a crude intermediate (165 mg, LC-MS m/z 508.2 $[M+H]^+$). To a solution of the crude intermediate (165 mg) in dioxane (0.6 mL), NaOH (10 N, 0.3 mL) was added. The reaction mixture was stirred at 70° C. for 5 h, neutralized with 0.2 mL of acetic acid, and purified by Method B. The fractions containing expected product were combined and freeze-dried to yield (S)-8-((5-amino-7-((1-hydroxyhexan-3-yl)amino)-1H-pyrazolo[4,3-d]pyrimidin-1-yl)methyl)-quinoline-5-carboxylic acid (82 mg, 0.188 mmol, 41.6% yield for 2 steps).

LC-MS m/z 436.2 $[M+H]^+$; Retention Time: 1.33 min (Method E).

Step 7. DIPEA (0.032 mL, 0.184 mmol) was added to a solution of (S)-8-((5-amino-7-((1-hydroxyhexan-3-yl)amino)-1H-pyrazolo[4,3-d]pyrimidin-1-yl)methyl)quinoline-5-carboxylic acid (20 mg, 0.046 mmol), 2-(piperazin-1-yl)ethan-1-ol (0.023 mL, 0.184 mmol) and HATU (26.2 mg, 0.069 mmol) in DMF (0.5 mL). The reaction mixture was stirred at 20° C. for 3 h, neutralized with 0.05 mL acetic acid, and purified by Method C. Fractions containing Compound 111 were combined and dried via centrifugal evaporation (2.74 mg, 0.005 mmol, 14.5%).

The following compounds were analogously prepared: Compound 108, Compound 112, Compound 113, Compound 114, Compound 125, Compound 126, Compound 127, Compound 128, Compound 129, Compound 130, Compound 131, Compound 132, Compound 133, Compound 134, Compound 135, Compound 136, and Compound 137.

Example 2—Compound 121

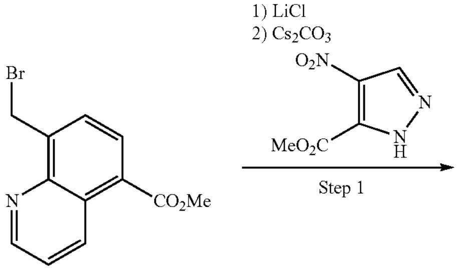

-continued

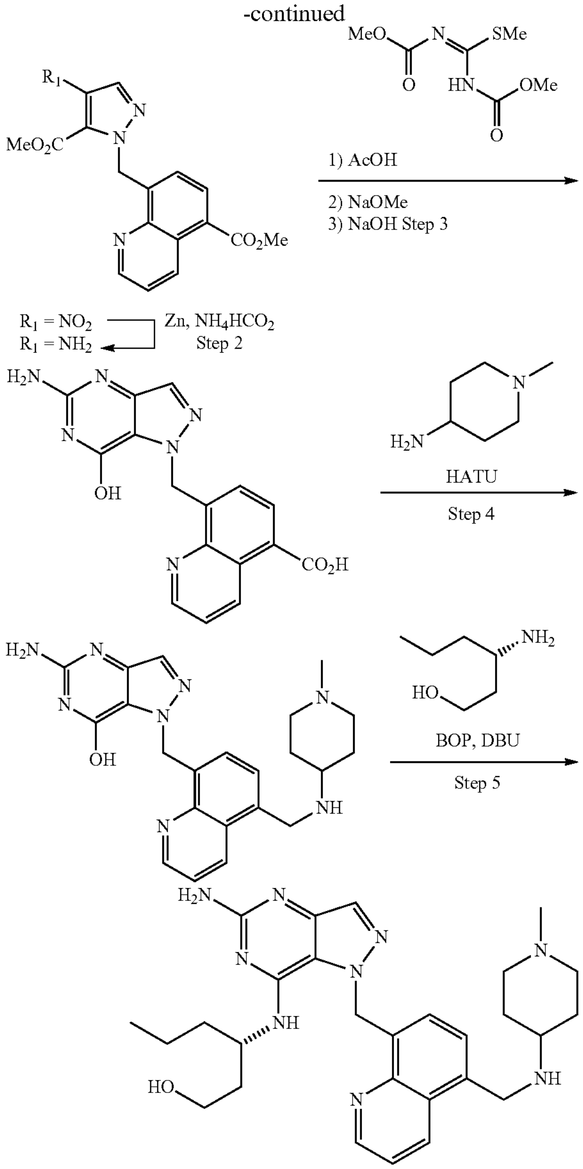

121

Step 1. LiCl (0.908 g, 21.42 mmol) was added to a solution of methyl 8-(bromo-methyl)quinoline-5-carboxylate (3 g, 10.71 mmol) in DMF (20 mL). The reaction mixture was stirred at RT for 30 min. LCMS analysis showed the starting material converted to a chloro intermediate (LC-MS m/z 236.1 $[M+H]^+$). Methyl 4-nitro-1H-pyrazole-5-carboxylate (3 g, 17.53 mmol) and $Cs_2CO_3$ (6.98 g, 21.42 mmol) were added. The reaction mixture was stirred at RT overnight. LCMS analysis showed the reaction was complete and generated 2 isomers (retention time: 1.874 min & 1.992 min at 3 min acidic run, M+H/z 371.1). The reaction mixture was worked up with EtOAc, water and brine. The organic phases were combined, concentrated and purified by column chromatography: Column: 80 g Combi-Flash column; Mobile Phase A: hexanes; Mobile Phase B: ethyl acetate; Gradient: a 2 min hold at 0% B, 0-40% B over 24 min, then a 3 min hold at 100% B; Flow Rate: 60 mL/min; Column Temperature: 25° C. The early fractions with 1.992 min retention time were combined, concentrated and dried under vacuum to yield methyl 8-((5-(methoxycarbonyl)-4-nitro-1H-pyrazol-1-yl)methyl)quinoline-5-carboxylate (635 mg, 1.715 mmol, 16.01% yield).

LC-MS m/z 371.1 $[M+H]^+$; Retention Time: 1.87 min (Method E).

Step 2. Zinc (785 mg, 12.00 mmol) was added portionwise over 1 h to a solution of methyl 8-((5-(methoxycarbonyl)-4-nitro-1H-pyrazol-1-yl)methyl)quinoline-5-carboxylate (635 mg, 1.715 mmol) in MeOH (7 mL) and THF (15 mL). The reaction mixture was stirred at RT for 2 h, diluted with EtOAc (50 mL), and filtered. The filtrate was concentrated and dried to yield methyl 8-((4-amino-5-(methoxycarbonyl)-1H-pyrazol-1-yl)methyl)quinoline-5-carboxylate salt (685 mg, 2.013 mmol, 117% yield).

LC-MS m/z 341.1 $[M+H]^+$; Retention Time: 1.61 min (Method E).

Step 3. Acetic acid (0.530 mL, 9.26 mmol) and TFA (0.4 mL) were added to a solution of 1,3-bis(methoxycarbonyl)-2-methyl-2-thiopseudourea (458 mg, 2.221 mmol) and methyl 8-((4-amino-5-(methoxycarbonyl)-1H-pyrazol-1-yl)methyl)quinoline-5-carboxylate (630 mg, 1.851 mmol) in MeOH (15 mL). The reaction mixture was stirred at RT overnight. LCMS analysis showed the reaction was complete, affording an intermediate (LC-MS m/z 499.2 $[M+H]^+$). Sodium methanolate (5.78 mL, 46.3 mmol) was added. The reaction mixture was stirred at RT for 10 min. LCMS analysis showed reaction was complete and another intermediate had formed (LC-MS m/z 409.2 $[M+H]^+$). The reaction mixture was concentrated to dryness. 2 mL of DMF and 1 mL of NaOH in water (10 N) were added to the residue. The reaction mixture was stirred at 60° C. for 3 h, neutralized with 1 mL of acetic acid, and concentrated under vacuum. The residue was purified by reverse phase column chromatography: Column: 150 g CombiFlash Aq column; Mobile Phase A: water with 0.05 TFA; Mobile Phase B: acetonitrile with 0.05% TFA; Gradient: a 2 min hold at 0% B, 0-40% B over 23 min, then a 4 min hold at 100% B; Flow Rate: 75 mL/min; Column Temperature: 25° C. The fractions containing expected product were combined and freeze-dried to yield 8-((5-amino-7-hydroxy-1H-pyrazolo[4,3-d]pyrimidin-1-yl)methyl)quinoline-5-carboxylic acid (265 mg, 0.788 mmol, 42.6% yield). LC-MS m/z 337.1 $[M+H]^+$; Retention Time: 1.05 min (Method E).

Step 4. DIPEA (50 uL) was added to a solution of 8-((5-amino-7-hydroxy-1H-pyrazolo[4,3-d]pyrimidin-1-yl)methyl)quinoline-5-carboxylic acid (28 mg, 0.083 mmol) and HATU (38.0 mg, 0.100 mmol) in DMF (0.5 mL). The reaction mixture was stirred at RT for 1 h, neutralized with 0.1 ml of acetic acid, and purified by Method B. The fractions containing the expected product were combined and freeze-dried to yield 8-((5-amino-7-hydroxy-1H-pyrazolo[4,3-d]pyrimidin-1-yl)methyl)-N-(1-methylpiperidin-4-yl)quinoline-5-carboxamide(25 mg, 0.058 mmol, 69.7%).

LC-MS m/z 433.2 $[M+H]^+$; Retention Time: 0.96 min (Method E).

Step 5. ((1H-benzo[d][1,2,3]triazol-1-yl)oxy)tris(dimethylamino)phosphonium hexafluorophosphate(V) (51.1 mg, 0.116 mmol) was added to a solution of 8-((5-amino-7-hydroxy-1H-pyrazolo[4,3-d]pyrimidin-1-yl)methyl)-N-(1-methylpiperidin-4-yl)quinoline-5-carboxamide (25 mg, 0.058 mmol), 2,3,4,6,7,8,9,10-octahydropyrimido[1,2-a]azepine (0.039 mL, 0.260 mmol) and (S)-3-aminohexan-1-ol (27.1 mg, 0.231 mmol) in DMSO (1.25 mL). The reaction mixture was stirred at 70° C. for 5 h and freeze-dried with acetonitrile and water. The residue was purified by Method C. Fractions containing the desired product were combined and dried via centrifugal evaporation to yield Compound 121 (9.39 mg, 0.018 mmol, 30.4%).

The following compounds were analogously prepared: Compound 115, Compound 116, Compound 117, Compound 118, Compound 122, Compound 124, and Compound 138.

Example 3—Compound 110

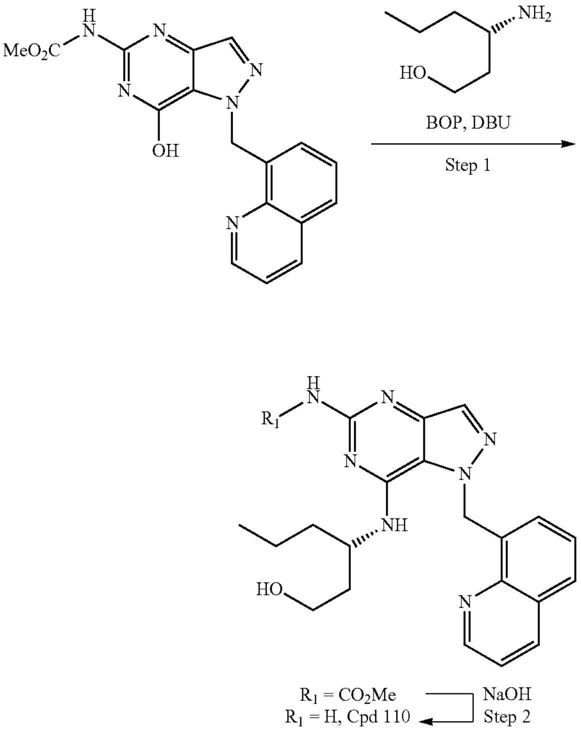

Step 1. ((1H-benzo[d][1,2,3]triazol-1-yl)oxy)tris(dimethylamino)phosphonium hexafluorophosphate(V) (26.0 mg, 0.059 mmol) was added to a solution of methyl (7-hydroxy-1-(quinolin-8-ylmethyl)-1H-pyrazolo[4,3-d]pyrimidin-5-yl)carbamate (10.3 mg, 0.029 mmol; prepared analogously per Example 1 from 8-(bromomethyl)quinoline), (S)-3-aminohexan-1-ol (17.23 mg, 0.147 mmol) and 2,3,4,6,7,8,9,10-octahydropyrimido[1,2-a]azepine (8.79 µl, 0.059 mmol) in DMSO (0.5 mL). The reaction mixture was stirred at 70° C. for 3 h, neutralized with 0.2 mL acetic acid, and purified by Method B. The fractions containing expected product were combined and freeze-dried to yield methyl (S)-(7-((1-hydroxyhexan-3-yl)amino)-1-(quinolin-8-ylmethyl)-1H-pyrazolo[4,3-d]pyrimidin-5-yl)carbamate (7.3 mg, 0.016 mmol, 55.2% yield).

LC-MS m/z 450.1 $[M+H]^+$; Retention Time: 1.64 min (Method E).

Step 2. Aqueous NaOH (0.3 mL, 3.00 mmol) was added to methyl (S)-(7-((1-hydroxy-hexan-3-yl)amino)-1-(quinolin-8-ylmethyl)-1H-pyrazolo[4,3-d]pyrimidin-5-yl)carbamate (7.3 mg, 0.016 mmol) in dioxane (0.6 mL). The reaction mixture was stirred at 70° C. for 4 h, neutralized with HOAc, and purified by Method B to yield Compound 110 (0.80 mg, 0.002 mmol, 12.6%).

Example 4—Compound 119

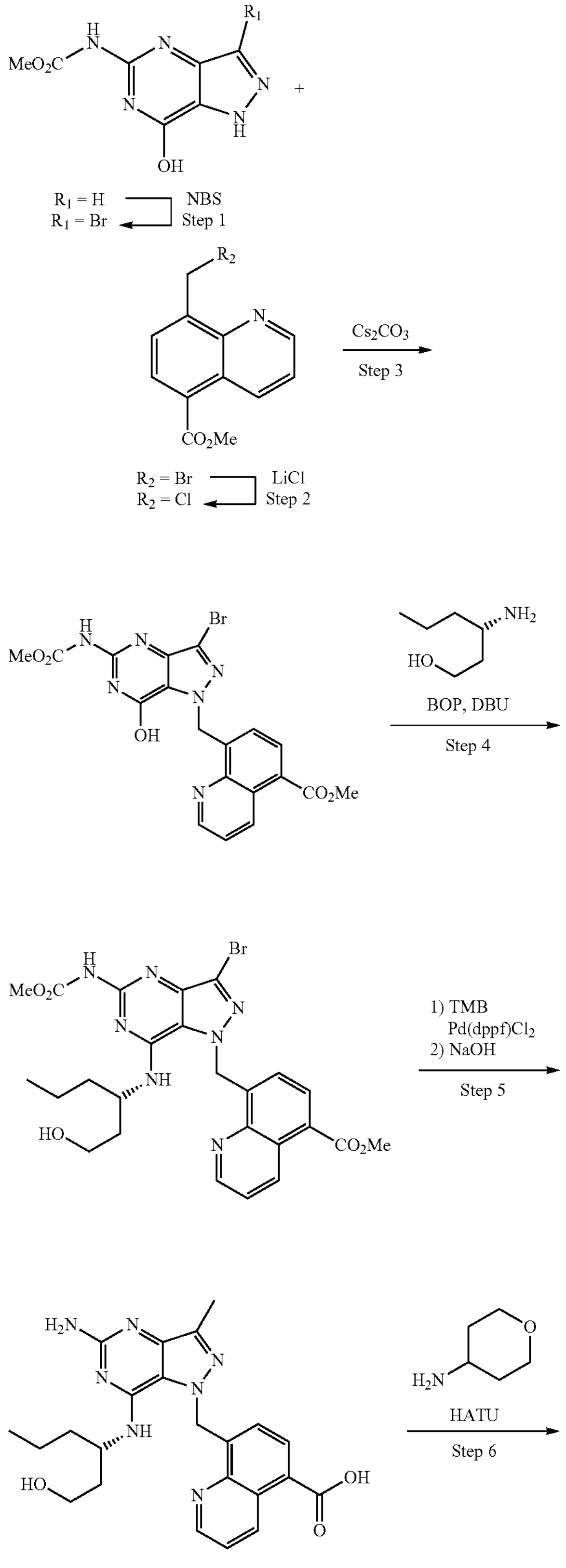

-continued

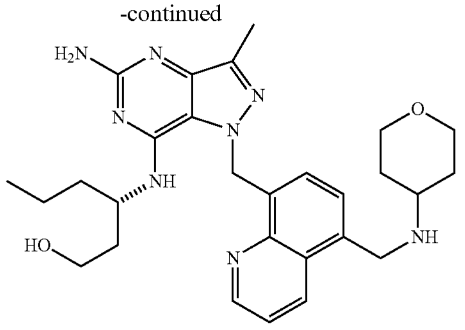

119

Step 1. 1-Bromopyrrolidine-2,5-dione (N-bromo succinimide (NBS), 2.059 g, 11.57 mmol) was added to a solution of methyl (7-hydroxy-1H-pyrazolo[4,3-d]pyrimidin-5-yl) carbamate (2.2 g, 10.52 mmol) in DMF (20 mL). The reaction mixture was stirred at RT for 1 h and with EtOAc, water and brine. The organic phases were combined, concentrated and dried under high vacuum for 1 h to yield methyl (3-bromo-7-hydroxy-1H-pyrazolo[4,3-d]pyrimidin-5-yl)carbamate (2.85 g, 9.89 mmol, 94% yield).

LC-MS m/z 288.0; 290.0 $[M+H]^+$; Retention Time: 1.07 min (Method E).

Steps 2 & 3. LiCl (143 mg, 3.37 mmol) was added to a solution of methyl 8-(bromomethyl)quinoline-5-carboxylate (236 mg, 0.842 mmol) in DMF (3 mL). The reaction mixture was stirred at RT for 30 min. LCMS analysis showed complete formation of the chloro intermediate, LC-MS m/z 236.1 $[M+H]^+$. Methyl (3-bromo-7-hydroxy-1H-pyrazolo[4,3-d]pyrimidin-5-yl)carbamate (291 mg, 1.010 mmol) and $Cs_2CO_3$ (1098 mg, 3.37 mmol) were added. The reaction mixture was stirred at RT for 120 h and worked up with EtOAc, water and brine. The organic phases were combined, concentrated and purified by column chromatography: Column: 24 g CombiFlash column; Mobile Phase A: hexanes; Mobile Phase B: ethyl acetate; Gradient: a 1 min hold at 0% B, 0-70% B over 11 min, then a 2 min hold at 100% B; Flow Rate: 35 mL/min; Column Temperature: 25° C. The fractions containing product were combined, concentrated and dried under high vacuum to yield methyl 8-((3-bromo-7-hydroxy-5-((methoxycarbonyl)amino)-1H-pyrazolo[4,3-d]pyrimidin-1-yl)methyl)quinoline-5-carboxylate (167 mg, 0.343 mmol, 40.7% yield).

LC-MS m/z 487.1; 489.1 $[M+H]^+$; Retention Time: 1.89 min (Method E).

Step 4. ((1H-Benzo[d][1,2,3]triazol-1-yl)oxy)tris(dimethylamino)phosphonium hexafluorophosphate(V) (178 mg, 0.402 mmol) was added to a solution of methyl 8-((3-bromo-7-hydroxy-5-((methoxycarbonyl)amino)-1H-pyrazolo[4,3-d]pyrimidin-1-yl)methyl)quinoline-5-carboxylate (98 mg, 0.201 mmol), (S)-3-aminohexan-1-ol HCl salt (155 mg, 1.006 mmol) and 2,3,4,6,7,8,9,10-octahydropyrimido[1,2-a]azepine (92 mg, 0.603 mmol) in DMSO (2.5 mL). The reaction mixture was stirred at 70° C. overnight, neutralized with HOAc, and purified (Method B). The fractions containing the product were combined and freeze-dried to yield methyl (S)-8-((3-bromo-7-((1-hydroxyhexan-3-yl)amino)-5-((methoxycarbonyl)amino)-1H-pyrazolo[4,3-d]pyrimidin-1-yl)methyl)quinoline-5-carboxylate (63 mg, 0.107 mmol, 53.4% yield). LC-MS m/z 586.2 $[M+H]^+$; Retention Time: 2.00 min (Method E).

Step 5. A mixture of methyl (S)-8-((3-bromo-7-((1-hydroxyhexan-3-yl)amino)-5-((methoxycarbonyl)amino)-1H-pyrazolo[4,3-d]pyrimidin-1-yl)methyl)quinoline-5-carboxylate (50 mg, 0.085 mmol), $K_2CO_3$ (41.2 mg, 0.298 mmol) and $PdCl_2$(dppf)-$CH_2Cl_2$ adduct (6.24 mg, 8.53 μmol) in dioxane (0.35 mL) and $H_2O$ (0.07 mL) was bubbled with $N_2$ for 1 min. 2,4,6-trimethyl-1,3,5,2,4,6-trioxatriborinane (TMB, 107 mg, 0.853 mmol) was added, bubbled with $N_2$ for 1 min, then sealed and stirred at 110° C. overnight. LCMS analysis showed the disappearance of starting material and formation of a new major peak (LC-MS m/z 464.3 $[M+H]^+$). Dioxane (0.43 mL) and 0.2 mL of 5N NaOH were added. The reaction mixture was stirred at 60° C. for 2 h, neutralized with 0.2 mL of acetic acid and purified by Method B. The fractions containing (S)-8-((5-amino-7-((1-hydroxyhexan-3-yl)amino)-3-methyl-1H-pyrazolo[4,3-d]pyrimidin-1-yl)methyl)-quinoline-5-carboxylic acid were combined and freeze-dried (29 mg, 0.065 mmol, 76% yield). LC-MS m/z 450.3 $[M+H]^+$. Retention Time: 1.40 min (Method E).

Step 6. DIPEA (0.019 mL, 0.107 mmol) was added to a solution of (S)-8-((5-amino-7-((1-hydroxyhexan-3-yl)amino)-3-methyl-1H-pyrazolo[4,3-d]pyrimidin-1-yl)methyl)quinoline-5-carboxylic acid (12 mg, 0.027 mmol), tetrahydro-2H-pyran-4-amine (10.80 mg, 0.107 mmol) and HATU (15.23 mg, 0.040 mmol) in DMF (0.5 mL). The reaction mixture was stirred at 20° C. for 0.5 h, neutralized with 0.05 mL acetic acid, and purified by Method C. Fractions containing Compound 119 were combined and dried via centrifugal evaporation (3.49 mg, 0.007 mmol, 24.3%).

Compound 120 and Compound 123 were analogously prepared.

Example 5—Compound 109

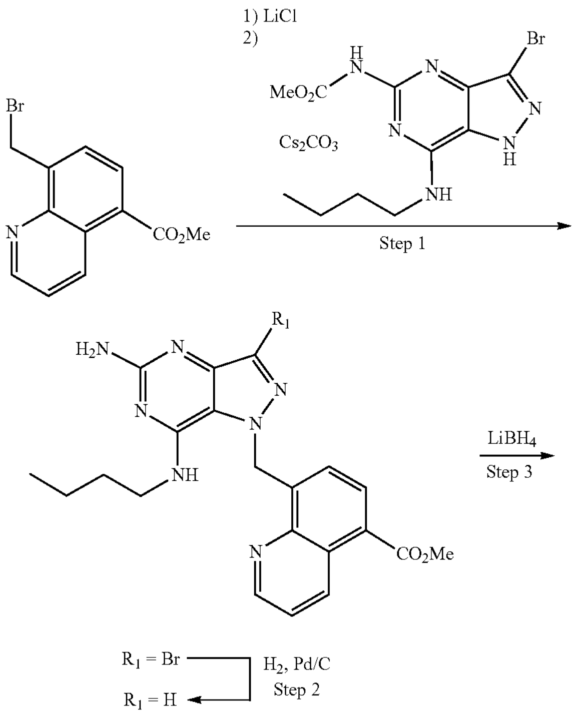

-continued

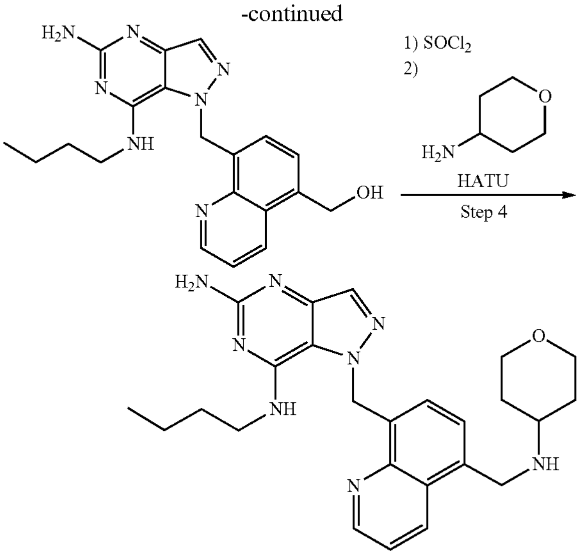

109

Step 1. To a solution of methyl 8-(bromomethyl)quinoline-5-carboxylate (236 mg, 0.842 mmol) in DMF (3 mL), LiCl (236 mg, 5.57 mmol) was added. The reaction mixture was stirred at RT for 2 h. LCMS analysis showed the reaction was complete (chloro intermediate, LC-MS m/z 236.1 $[M+H]^+$). 3-Bromo-N7-butyl-1H-pyrazolo[4,3-d]pyrimidine-5,7-diamine (200 mg, 0.701 mmol) and $Cs_2CO_3$ (914 mg, 2.81 mmol) were added. The reaction mixture was stirred at RT for over weekend. LCMS analysis showed the reaction was complete with 2 isomers corresponding to desired mass (LC-MS m/z 484.2; 486.2 $[M+H]^+$). The reaction mixture was worked up with EtOAc, water and brine. The organic phases were combined, concentrated and purified with column chromatography: Column: 40 g CombiFlash column; Mobile Phase A: hexanes; Mobile Phase B: ethyl acetate; Gradient: a 1 min hold at 0% B, 0-100% over 14 min, then a 3 min hold at 100% B; Flow Rate: 40 mL/min; Column Temperature: 25° C. the fractions containing product were combined, concentrated and dried under high vacuum to yield methyl 8-((5-amino-3-bromo-7-(butylamino)-1H-pyrazolo[4,3-d]pyrimidin-1-yl)methyl)quinoline-5-carboxylate (161 mg, 0.332 mmol, 47.5%).

LC-MS m/z 484.2; 486.2 $[M+H]^+$; Retention Time: 1.85 min (Method E).

Step 2. To a solution of methyl 8-((5-amino-3-bromo-7-(butylamino)-1H-pyrazolo[4,3-d]pyrimidin-1-yl)methyl) quinoline-5-carboxylate (161 mg, 0.332 mmol) in MeOH (10 mL), Pd—C(10%, 53 mg) was added. The reaction mixture was stirred under hydrogen balloon overnight and filtered. The filtrate was concentrated and dried under high vacuum to yield methyl 8-((5-amino-7-(butylamino)-1H-pyrazolo[4,3-d]pyrimidin-1-yl)methyl)quinoline-4-carboxylate (128 mg, 0.316 mmol, 95.2%).

LC-MS m/z 406.3 $[M+H]^+$. Retention Time: 1.67 min (Method E).

Step 3. To a solution of methyl 8-((5-amino-7-(butylamino)-1H-pyrazolo[4,3-d]pyrimidin-1-yl)methyl)quinoline-5-carboxylate (60 mg, 0.148 mmol) in THF (1 mL) and MeOH (0.1 mL), $LiBH_4$ in THF (0.740 mL, 0.740 mmol) was added. The reaction mixture was stirred at 40° C. for 1 h, neutralized with 0.07 mL of HOAc, and purified with Method B. The fractions containing expected product were combined and freeze-dried to yield (8-((5-amino-7-(butylamino)-1H-pyrazolo[4,3-d]pyrimidin-1-yl)methyl)quinolin-5-yl)methanol (25 mg, 0.066 mmol, 44.8%).

LC-MS m/z 378.3 $[M+H]^+$. Retention Time: 1.45 min (Method E).

Step 4. To a solution of (8-((5-amino-7-(butylamino)-1H-pyrazolo[4,3-d]pyrimidin-1-yl)methyl)quinolin-5-yl)methanol (25 mg, 0.066 mmol) in THF (1 mL), sulfurous dichloride (0.024 mL, 0.331 mmol) was added. The reaction mixture was stirred at RT for 5 min. LCMS analysis showed the reaction was complete (LC-MS m/z 396.3 $[M+H]^+$). The reaction mixture was concentrated under vacuum and co-evaporated with dry DCM (2×5 mL). The residue was dried under high vacuum for 10 min and dissolved in DMF (1 mL). Tetrahydro-2H-pyran-4-amine (67.0 mg, 0.662 mmol) was added. The reaction mixture was stirred at 25° C. for 4 h and purified with Method A. Fractions containing the desired product were combined and dried via centrifugal evaporation to yield Compound 109 (14.49 mg, 0.021 mmol, 31.9%).

Compound 101 and Compound 107 were analogously prepared.

Example 6—Compound 102

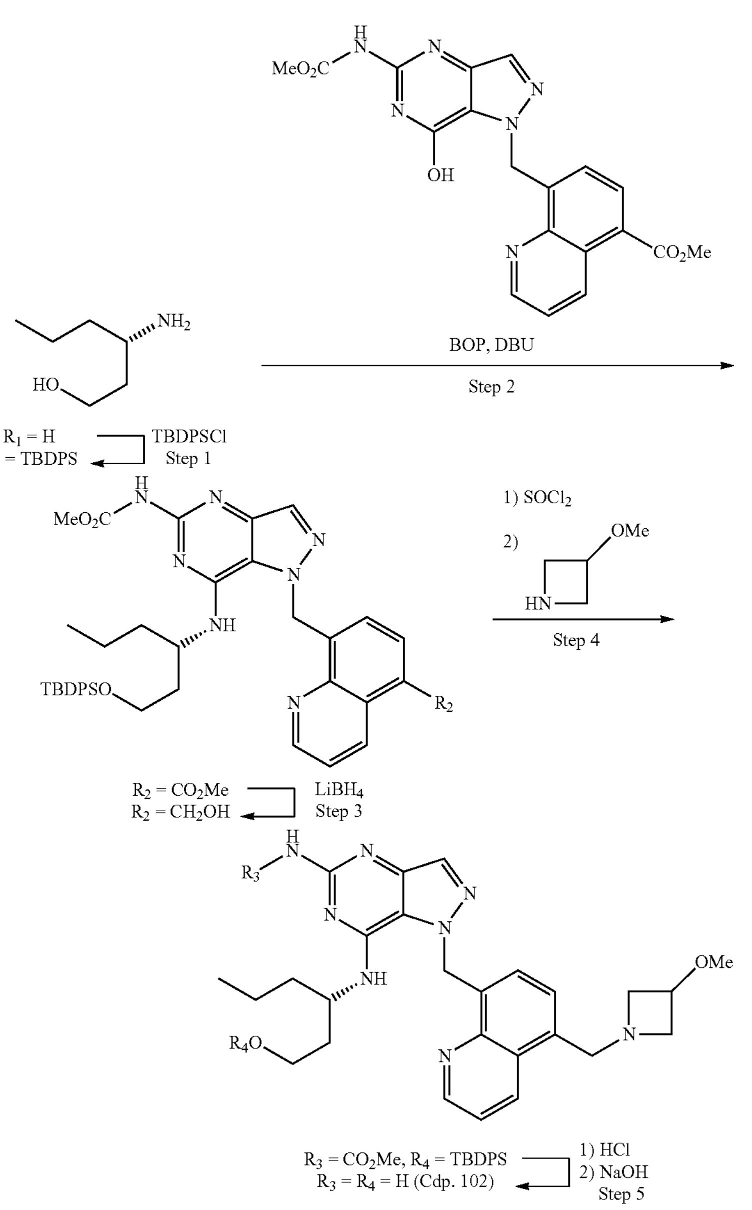

Step 1. Imidazole (1.452 g, 21.33 mmol) was added to a solution of (S)-3-aminohexan-1-ol (1 g, 8.53 mmol) and tert-butylchlorodiphenylsilane (TBPDSCl3.28 mL, 12.80 mmol) in DMF (6 mL). The reaction mixture was stirred at RT overnight and worked up with EtOAc, water and brine. The organic phases were combined, concentrated and purified by column chromatography: Column: 40 g CombiFlash column; Mobile Phase A: hexanes; Mobile Phase B: ethyl acetate; Gradient: a 1 min hold at 0% B, 0-100% over 14 min, then a 3 min hold at 100% B; Flow Rate: 40 mL/min; Column Temperature: 25° C. The fractions containing the expected product were combined, concentrated and dried under high vacuum to yield (S)-1-((tert-butyldiphenylsilyl)oxy)hexan-3-amine (2.09 g, 5.88 mmol, 68.9% yield).

LC-MS m/z 356.2 $[M+H]^+$; Retention Time: 2.51 min (Method E).

Step 2. BOP (433 mg, 0.979 mmol) was added to a solution of methyl 8-((7-hydroxy-5-((methoxycarbonyl)amino)-1H-pyrazolo[4,3-d]pyrimidin-1-yl)methyl)quinoline-5-carboxylate (200 mg, 0.490 mmol), (S)-1-((tert-butyldiphenylsilyl)oxy)hexan-3-amine (871 mg, 2.449 mmol) and DBU (0.148 mL, 0.979 mmol) in DMSO (3 mL). The reaction mixture was stirred at 70° C. for 3 h, neutralized with 0.2 mL acetic acid, and purified by reverse phase column chromatography: Column: 50 g CombiFlash Aq column; Mobile Phase A: water with 0.05 TFA; Mobile Phase B: acetonitrile with 0.05% TFA; Gradient: a 0.75 min hold at 0% B, 0-50% B over 8.75 min, then a 1.5 min hold at 100% B; Flow Rate: 35 mL/min; Column Temperature: 25° C. The fractions containing methyl (S)-8-((7-((1-((tert-butyldiphenylsilyl)oxy)hexan-3-yl)amino)-5-((methoxycarbonyl)amino)-1H-pyrazolo[4,3-d]pyrimidin-1-yl)methyl)quinoline-5-carboxylate were combined and freeze-dried (258 mg, 0.346 mmol, 70.6% yield).

LC-MS m/z 746.3 $[M+H]^+$. Retention Time: 2.57 min (Method E).

Step 3. $LiBH_4$ (2N, 0.4 mL) was added to a solution of methyl (S)-8-((7-((1-((tert-butyldiphenylsilyl)oxy)hexan-3-yl)amino)-5-((methoxycarbonyl)amino)-1H-pyrazolo[4,3-d]pyrimidin-1-yl)methyl)quinoline-5-carboxylate (121 mg, 0.162 mmol) in THF (1.8 mL) and MeOH (0.2 mL). The reaction mixture was stirred at 40° C. for 1 h, neutralized with 0.2 mL acetic acid, and purified by Method B. The fractions containing methyl (S)-(7-((1-((tert-butyl-diphenylsilyl)oxy)hexan-3-yl)amino)-1-((5-(hydroxymethyl)quinolin-8-yl)methyl)-1H-pyrazolo-[4,3-d]pyrimidin-5-yl)carbamate were combined and freeze-dried (43 mg, 0.060 mmol, 36.9%).

LC-MS m/z 718.3 $[M+H]^+$. Retention Time: 2.51 min (Method E).

Step 4. $SOCl_2$ (0.024 mL, 0.334 mmol) was added to a solution of methyl (S)-(7-((1-((tert-butyldiphenylsilyl)oxy)hexan-3-yl)amino)-1-((5-(hydroxymethyl)quinolin-8-yl)methyl)-1H-pyrazolo[4,3-d]pyrimidin-5-yl)carbamate (48 mg, 0.067 mmol) in THF (1 mL). The reaction mixture was stirred at RT for 5 min. LCMS analysis showed that the starting material was completely converted to a chloro intermediate (LC-MS m/z 736.3 $[M+H]^+$). The reaction mixture was concentrated under vacuum and co-evaporated with dry DCM (2×5 mL). The residue was dried under high vacuum for 10 min to a residue. The residue was dissolved in DMF (1 ml) and DIEA (0.070 mL, 0.401 mmol) and 3-methoxyazetidine (34.9 mg, 0.401 mmol) were added. The reaction mixture was stirred at 70° C. for 30 min and freeze-dried with acetonitrile and water to yield crude methyl (S)-(7-((1-((tert-butyldiphenylsilyl)oxy)hexan-3-yl)amino)-1-((5-((3-methoxyazetidin-1-yl)methyl)quinolin-8-yl)methyl)-1H-pyrazolo[4,3-d]pyrimidin-5-yl)carbamate (52.1 mg, 0.066 mmol, 99%).

LC-MS m/z 787.3 $[M+H]^+$. Retention Time: 2.60 min (Method E).

Step 5. NaOH in water (0.3 ml, 3.00 mmol) was added to a solution of methyl (S)-(7-((1-((tert-butyldiphenylsilyl)oxy)hexan-3-yl)amino)-1-((5-((3-methoxyazetidin-1-yl)methyl)-quinolin-8-yl)methyl)-1H-pyrazolo[4,3-d]pyrimidin-5-yl)carbamate (52.1 mg, 0.066 mmol) in 1,4-dioxane (0.6 mL). The reaction mixture was stirred at 70° C. for 3 h, neutralized with 0.3 mL HCl (12 M), and freeze-dried with acetonitrile and water to afford a crude intermediate. To a mixture of intermediate (143 mg crude) in MeOH (0.8 ml), HCl (12M, 0.3 mL) was added. The slurry was stirred at RT for 1 h, diluted with acetonitrile (10 mL) and water (10 mL), and freeze-dried to give crude product. The crude product was dissolved in 1 mL of DMSO and filtered. The filtrate was purified by Method C. Fractions containing the desired product were combined and dried via centrifugal evaporation to yield Compound 102 (7.62 mg, 0.016 mmol, 24.3%).

The following compounds were analogously prepared: Compound 103, Compound 104, Compound 105, Compound 106, Compound 139, and Compound 140.

Example 7—Compound 141

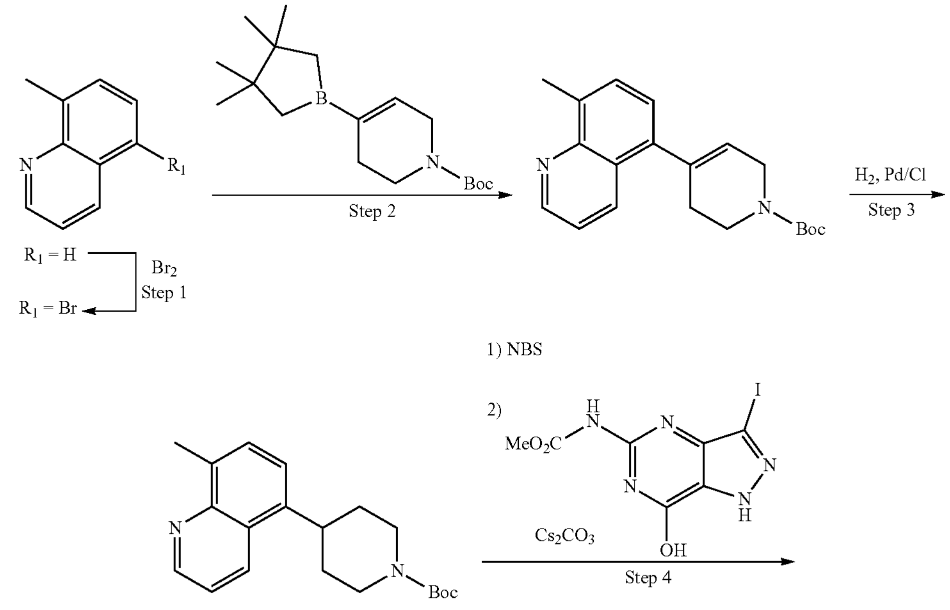

-continued

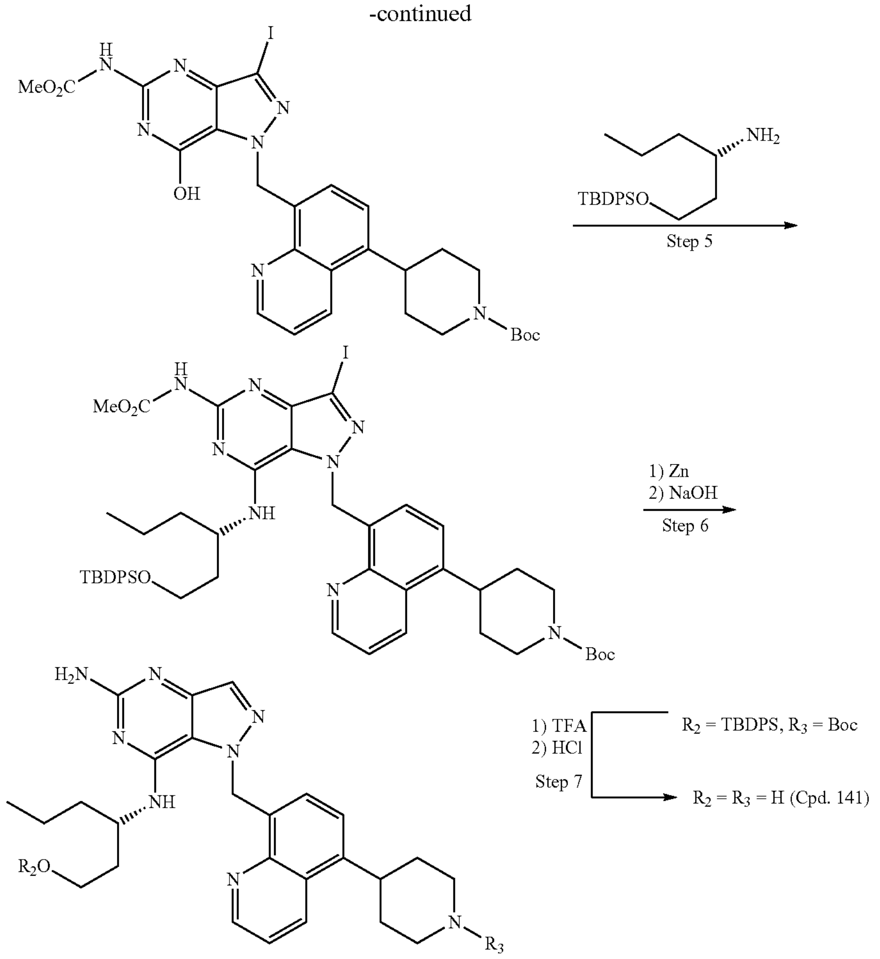

Step 1. Bromine (3.60 ml, 69.8 mmol) was added to a solution of 8-methylquinoline (9.51 ml, 69.8 mmol) and silver sulfate (32.7 g, 105 mmol) in concentrated $H_2SO_4$ (98%, 100 mL) cooled to 0° C. in an ice batch. The reaction mixture was stirred at 25° C. for 4 h and diluted with ice. $NH_4OH$ solution was added slowly (14.8 M) raise the pH above 7. The reaction mixture was extracted with EtOAc (4×250 mL). The organic phases were combined, concentrated and purified by column chromatography: Column: 80 g CombiFlash column; Mobile Phase A: hexanes; Mobile Phase B: ethyl acetate; Gradient: a 3 min hold at 0% B, 0-10% over 45 min, then a 3 min hold at 10% B; Flow Rate: 85 mL/min; hexanes with 0.05% TEA; Column Temperature: 25° C. The fractions containing expected product were combined, concentrated and dried on reduced vacuum for 30 min to yield 5-bromo-8-methylquinoline (13.1 g, 59.0 mmol, 84% yield).

LC-MS m/z 222.1 & 224.1 $[M+H]^+$; Retention Time: 2.05 min (Method E).

Step 2. A mixture of 5-bromo-8-methylquinoline (1 g, 4.50 mmol), tert-butyl 4-(3,3,4,4-tetramethylborolan-1-yl)-3,6-dihydropyridine-1(2H)-carboxylate (1.787 g, 5.85 mmol) and 5-bromo-8-methylquinoline (1 g, 4.50 mmol), tert-butyl 4-(3,3,4,4-tetramethylborolan-1-yl)-3,6-dihydro-pyridine-1(2H)-carboxylate (1.787 g, 5.85 mmol) in DMF (15 mL) was bubbled with $N_2$ for 3 min. $PdCl_2$(dppf) (0.329 g, 0.450 mmol) was added. $N_2$ was bubbled for another 2 min. The reaction vessel was sealed. The reaction mixture was stirred at 80° C. for 5 h, diluted with EtOAc, and filtered through CELITE. The filtrate was concentrated and was purified by column chromatography: Column: 80 g Combi-Flash column; Mobile Phase A: hexanes; Mobile Phase B: ethyl acetate; Gradient: a 3 min hold at 0% B, 0-10% over 45 min, then a 3 min hold at 10% B; Flow Rate: 85 mL/min; hexanes with 0.05% TEA; Column Temperature: 25° C. The desired fractions were concentrated to yield tert-butyl 4-(8-methylquinolin-5-yl)-3,6-dihydro-pyridine-1(2H)-carboxylate (1.28 g, 3.95 mmol, 88% yield).

LC-MS m/z 324.9 $[M+H]^+$; Retention Time: 1.98 min (Method E).

$^1$H NMR (400 MHz, DMSO-d6) δ 8.93 (dd, J=4.1, 1.8 Hz, 1H), 8.35 (dd, J=8.5, 1.8 Hz, 1H), 7.64-7.49 (m, 2H), 7.32 (d, J=7.2 Hz, 1H), 5.74 (s, 1H), 4.06 (q, J=2.8 Hz, 2H), 3.64 (t, J=5.6 Hz, 2H), 2.71 (d, J=0.9 Hz, 3H), 2.44 (ddt, J=7.9, 5.6, 2.7 Hz, 2H), 1.46 (s, 9H).

Step 3. A mixture of tert-butyl 4-(8-methylquinolin-5-yl)-3,6-dihydropyridine-1(2H)-carboxylate (1.35 g, 4.16 mmol) and Pd—C(0.222 g, 0.21 mmol) in MeOH (15 mL) was stirred under hydrogen balloon. The reaction was monitored with LCMS. The reaction was 40% completed in 8 hrs. The reaction mixture was filtered and the filtrate was concentrated and purified by column chromatography: Column: 40 g CombiFlash column; Mobile Phase A: hexanes; Mobile Phase B: ethyl acetate; Gradient: a 1 min hold at 0% B, 0-10% over 14 min, then a 1 min hold at 10% B; Flow Rate: 40 mL/min; hexanes with 0.05% TEA; Column Temperature: 25° C. The fractions containing expected product were combined, concentrated and dried under high vacuum to yield tert-butyl 4-(8-methylquinolin-5-yl)piperidine-1-carboxylate (0.412 g, 1.262 mmol, 30.3% yield).

LC-MS m/z 324.9 $[M+H]^+$; Retention Time: 1.98 min (Method E).

$^1$H NMR (400 MHz, DMSO-d6) δ 8.93 (dd, J=4.1, 1.6 Hz, 1H), 8.64 (dd, J=8.7, 1.6 Hz, 1H), 7.61-7.53 (m, 2H), 7.38 (dd, J=7.5, 1.5 Hz, 1H), 4.13 (d, J=12.9 Hz, 2H), 3.64-3.46 (m, 1H), 3.31 (s, 1H), 2.69 (s, 3H), 1.87-1.78 (m, 2H), 1.60 (qd, J=12.5, 4.1 Hz, 2H), 1.44 (s, 9H).

Step 4. AIBN (14.59 mg, 0.089 mmol) was added to a solution of tert-butyl 4-(8-methylquinolin-5-yl)piperidine-1-carboxylate (290 mg, 0.888 mmol) and NBS (190 mg, 1.066 mmol) in $CCl_4$ (4 mL). The reaction mixture was stirred at RT overnight. LCMS analysis showed 30% conversion to an intermediate (2.393 min at Method E, M+H/z=405.2; 407.2). Extra AIBN (14.59 mg, 0.089 mmol) was added. The reaction mixture was stirred at RT overnight. LCMS analysis showed 50% conversion. The reaction mixture was worked up with EtOAc, water and brine. The organic phases were concentrated and dried under vacuum to yield crude intermediate tert-butyl 4-(8-(bromomethyl)quinolin-5-yl)piperidine-1-carboxylate (349 mg).

$Cs_2CO_3$ (868 mg, 2.67 mmol) was added to a solution of methyl (7-hydroxy-3-iodo-1H-pyrazolo[4,3-d]pyrimidin-5-yl)carbamate (298 mg, 0.888 mmol) and crude intermediate tert-butyl 4-(8-(bromomethyl)quinolin-5-yl)piperidine-1-carboxylate (349 mg) in DMF (3 mL). The reaction mixture was stirred at 25° C. for 30 min. LCMS showed reaction was completed. The reaction mixture was worked up with EtOAc, water and brine. The organics were combined, concentrated and purified by column chromatography: Column: 24 g CombiFlash column; Mobile Phase A: hexanes; Mobile Phase B: ethyl acetate; Gradient: a 1 min hold at 0% B, 0-100% over 14 min, then a 1 min hold at 100% B; Flow Rate: 25 mL/min; Column Temperature: 25° C. The fractions containing desired product were concentrated to yield tert-butyl 4-(8-((7-hydroxy-3-iodo-5-((methoxycarbonyl)amino)-1H-pyrazolo[4,3-d]pyrimidin-1-yl)methyl)quinolin-5-yl)piperidine-1-carboxylate (135 mg, 0.205 mmol, 23.04% yield).

LC-MS m/z [M+H]+; Retention Time: min (Method E).

Step 5. DBU (0.371 mL, 2.464 mmol) was added to a solution of tert-butyl 4-(8-((7-hydroxy-3-iodo-5-((methoxycarbonyl)amino)-1H-pyrazolo[4,3-d]pyrimidin-1-yl)methyl)quinolin-5-yl)piperidine-1-carboxylate (325 mg, 0.493 mmol), (S)-1-((tert-butyldiphenylsilyl)oxy)hexan-3-amine (350 mg, 0.986 mmol) and BOP (436 mg, 0.986 mmol) in DMSO (4.5 mL). The reaction mixture was stirred at 45° C. for 4 h and worked up with EtOAc, water and brine. The organic phases were combined, concentrated and purified by column chromatography: Column: 12 g CombiFlash column; Mobile Phase A: hexanes; Mobile Phase B: ethyl acetate; Gradient: a 1 min hold at 0% B, 0-10% over 15 min, then a 1 min hold at 10% B; Flow Rate: 20 mL/min; Column Temperature: 25° C. The fractions containing desired product were concentrated and dried under reduced pressure to yield tert-butyl (S)-4-(8-((7-((1-((tert-butyldiphenylsilyl)oxy)hexan-3-yl)amino)-3-iodo-5-((methoxycarbonyl)amino)-1H-pyrazolo[4,3-d]pyrimidin-1-yl)methyl)-quinolin-5-yl)piperidine-1-carboxylate (315 mg, 0.316 mmol, 64.1% yield).

LC-MS m/z 997.6 [M+H]+; Retention Time: 2.56 min (Method F).

$^1$H NMR (400 MHz, DMSO-d6) δ 9.72 (s, 1H), 8.98 (dd, J=4.2, 1.6 Hz, 1H), 8.78-8.70 (m, 1H), 7.66 (dd, J=8.7, 4.2 Hz, 1H), 7.53-7.46 (m, 2H), 7.42-7.13 (m, 10H), 6.82 (s, 1H), 6.21 (s, 2H), 4.56 (s, 2H), 3.58 (s, 4H), 3.48 (s, 2H), 2.91 (s, 5H), 2.68 (s, 1H), 2.53 (s, 1H), 1.74 (d, J=12.8 Hz, 2H), 1.58 (s, 1H), 1.53-1.47 (m, 1H), 1.43 (s, 9H), 0.99 (s, 1H), 0.86 (s, 9H), 0.72 (t, J=7.3 Hz, 3H).

Step 6. Zinc (168 mg, 2.57 mmol) was added to a solution of tert-butyl (S)-4-(8-((7-((1-((tert-butyldiphenylsilyl)oxy)hexan-3-yl)amino)-3-iodo-5-((methoxycarbonyl)amino)-1H-pyrazolo[4,3-d]pyrimidin-1-yl)methyl)quinolin-5-yl)piperidine-1-carboxylate (256 mg, 0.257 mmol) in MeOH (4 mL) and AcOH (2 mL). The reaction mixture was stirred at 25° C. for 1 h and worked up with EtOAc, water and brine. The organic phases were combined, concentrated and generated intermediate tert-butyl (S)-4-(8-((7-((1-((tert-butyldiphenylsilyl)oxy)hexan-3-yl)amino)-5-((methoxycarbonyl)amino)-1H-pyrazolo[4,3-d]pyrimidin-1-yl)methyl)quinolin-5-yl)piperidine-1-carboxylate (186 mg).

LC-MS m/z 871.7 [M+H]+; Retention Time: 1.82 min (Method F).

NaOH (10 N, 1 mL) was added to a solution of the intermediate (186 mg) in dioxane (4 mL). The reaction mixture was stirred at 78° C. overnight and worked up with EtOAc, water and brine. The organic phases were concentrated and dried under vacuum to yield tert-butyl (S)-4-(8-((5-amino-7-((1-((tert-butyldiphenylsilyl)oxy)hexan-3-yl)amino)-1H-pyrazolo[4,3-d]pyrimidin-1-yl)methyl)quinolin-5-yl)piperidine-1-carboxylate (151 mg, 0.186 mmol, 72.3% yield).

LC-MS m/z 813.7 [M+H]+; Retention Time: 2.48 min (Method E).

Step 7. TFA (0.5 mL) was added to a solution of tert-butyl (S)-4-(8-((5-amino-7-((1-((tert-butyldiphenylsilyl)oxy)hexan-3-yl)amino)-1H-pyrazolo[4,3-d]pyrimidin-1-yl)methyl)-quinolin-5-yl)piperidine-1-carboxylate (32 mg, 0.039 mmol) in DCM (0.5 mL), The reaction mixture was stirred at 25° C. for 30 min. LCMS showed Boc protecting group removed. The reaction mixture was concentrated and dissolved in Dioxane (0.5 ml). To it, HCl (12 N, 0.5 mL) was added. The reaction mixture was stirred at RT for 15 min and concentrated and purified by Method C. Fractions containing the desired product were combined and dried via centrifugal evaporation to yield Compound 141 (2.4 mg, 0.005 mmol, 13.0%).

Example 8—Compound 142

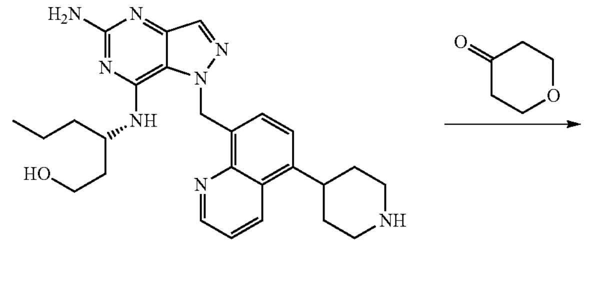

-continued

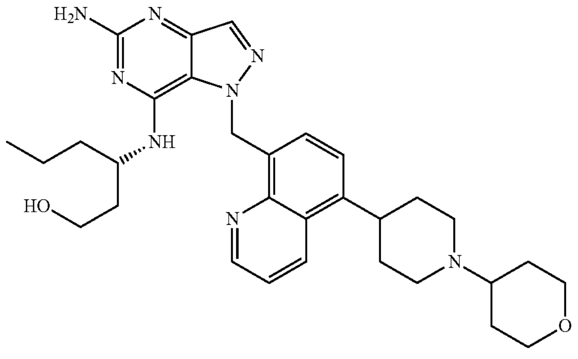

142

A solution of (S)-3-((5-amino-1-((5-(piperidin-4-yl)quinolin-8-yl)methyl)-1H-pyrazolo[4,3-d]pyrimidin-7-yl)amino)hexan-1-ol (20 mg, 0.042 mmol) in DMF (0.6 mL) was treated with Molecular Sieves, tetrahydro-4H-pyran-4-one (21.09 mg, 0.211 mmol) and 1 drop of HOAc, followed by sodium triacetoxyborohydride (35.7 mg, 0.169 mmol). The reaction mixture was stirred at RT overnight and purified by Method C to yield Compound 142 (5.0 mg, 8.55 μmol, 20.28% yield).

Compound 143 was analogously prepared.

Example 9—Starting Materials and Intermediates

The Charts below show schemes for making compounds that could be useful as starting materials or intermediates for the preparation of TLR7 agonists disclosed herein. The schemes can be adapted to make other, analogous compounds that could be used as starting materials or intermediates. The reagents employed are well known in the art and in many instances their use has been demonstrated in the preceding Examples.

Chart 1

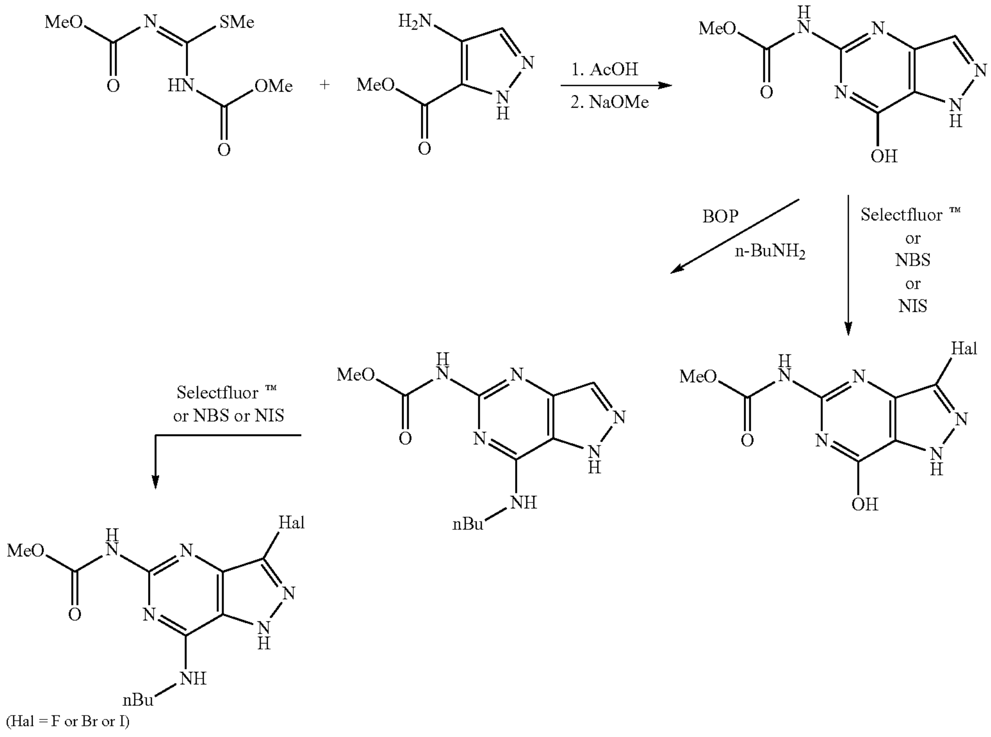

Chart 2

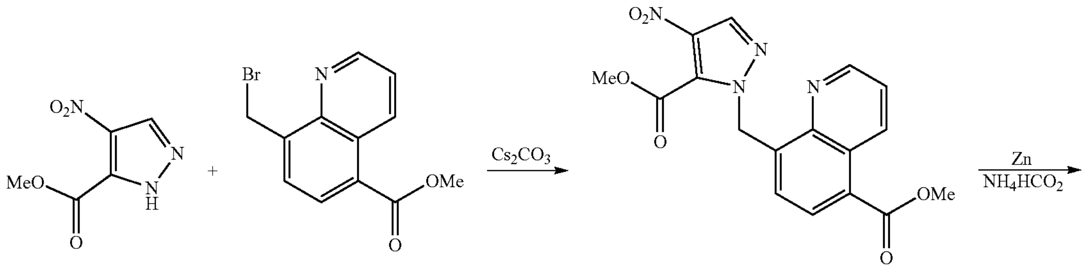

-continued
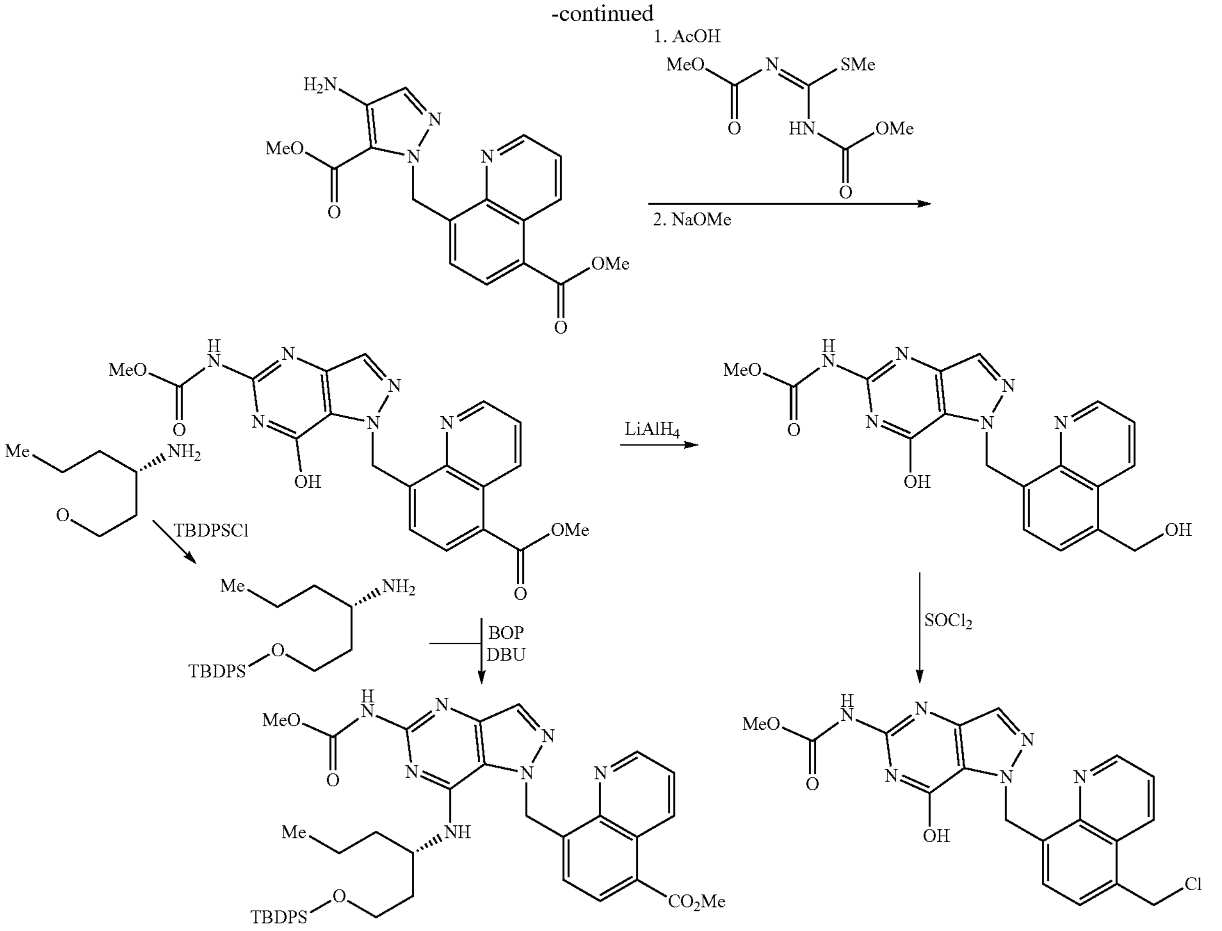
Chart 3
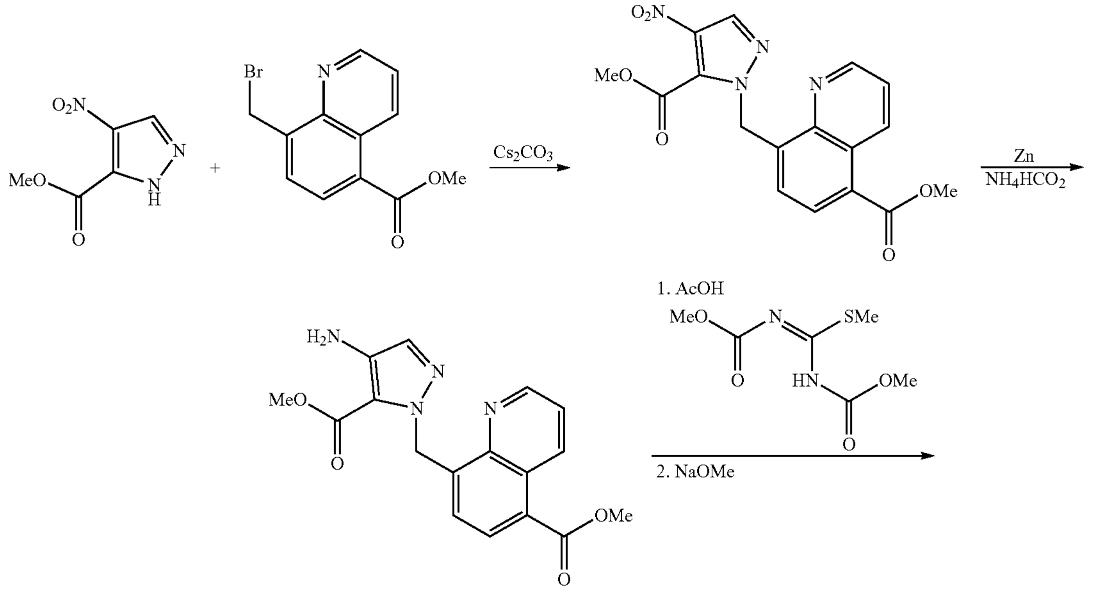

-continued

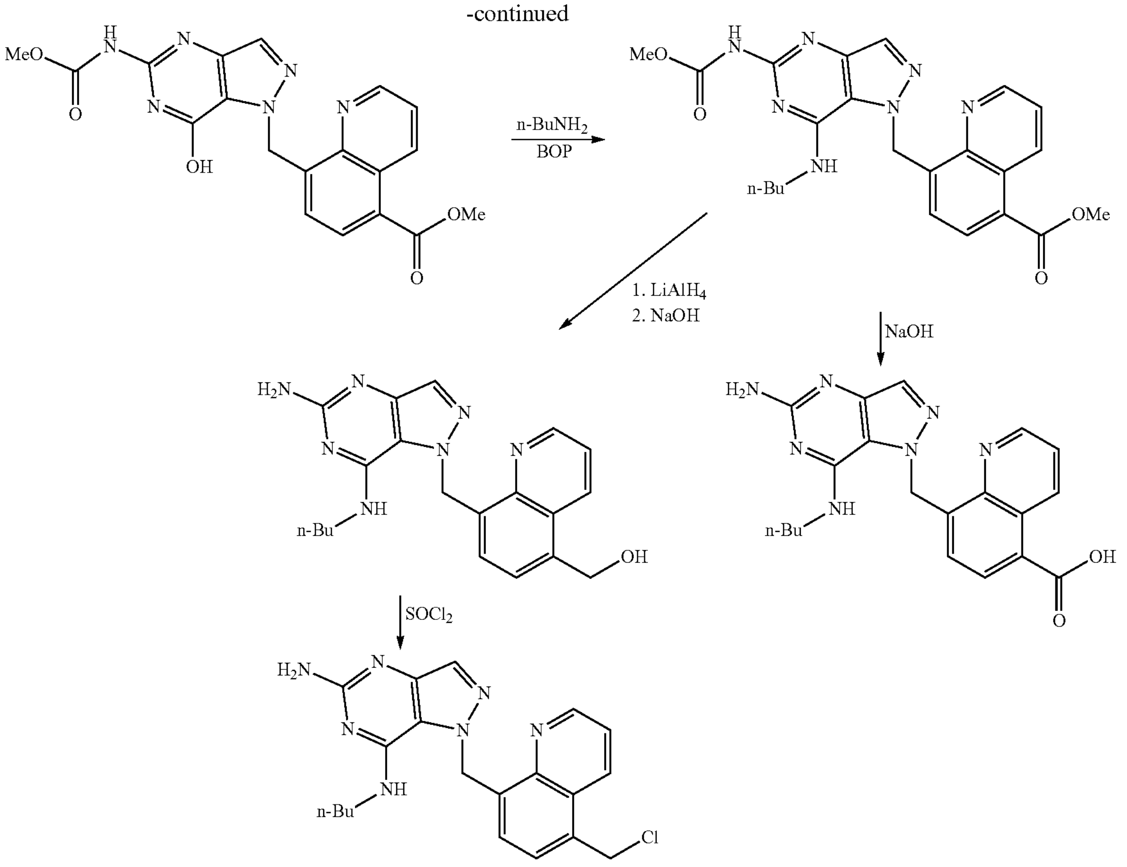

Biological Activity

The biological activity of compounds disclosed herein as TLR7 agonists can be assayed by the procedures following.

Human TLR7 Agonist Activity Assay

This procedure describes a method for assaying human TLR7 (hTLR7) agonist activity of the compounds disclosed in this specification.

Engineered human embryonic kidney blue cells (HEK-Blue™ TLR cells; Invivogen) possessing a human TLR7-secreted embryonic alkaline phosphatase (SEAP) reporter transgene were suspended in a non-selective, culture medium (DMEM high-glucose (Invitrogen), supplemented with 10% fetal bovine serum (Sigma)). HEK-Blue™ TLR7 cells were added to each well of a 384-well tissue-culture plate (15,000 cells per well) and incubated 16-18 h at 37° C., 5% $CO_2$. Compounds (100 nl) were dispensed into wells containing the HEK-Blue™ TLR cells and the treated cells were incubated at 37° C., 5% $CO_2$. After 18 h treatment ten microliters of freshly-prepared Quanti-Blue™ reagent (Invivogen) was added to each well, incubated for 30 min (37° C., 5% $CO_2$) and SEAP levels measured using an Envision plate reader (OD=620 nm). The half maximal effective concentration values ($EC_{50}$; compound concentration which induced a response halfway between the assay baseline and maximum) were calculated.

Induction of Type I Interferon Genes (MX-1) and CD69 in Human Blood

The induction of Type I interferon (IFN) MX-1 genes and the B-cell activation marker CD69 are downstream events that occur upon activation of the TLR7 pathway. The following is a human whole blood assay that measures their induction in response to a TLR7 agonist.

Heparinized human whole blood was harvested from human subjects and treated with test TLR7 agonist compounds at 1 mM. The blood was diluted with RPMI 1640 media and Echo was used to predot 10 nL per well giving a final concentration of 1 uM (10 nL in 10 uL of blood). After mixing on a shaker for 30 sec, the plates were covered and placed in a 37° C. chamber for o/n=17 hrs. Fixing/lysis buffer was prepared (5x→1x in $H_2O$, warm at 37° C.; Cat #BD 558049) and kept the perm buffer (on ice) for later use.

For surface markers staining (CD69): prepared surface Abs: 0.045 ul hCD14-FITC (ThermoFisher Cat #MHCD1401)+0.6 ul hCD19-ef450 (ThermoFisher Cat #48-0198-42)+1.5 ul hCD69-PE (cat #BD555531)+0.855 ul FACS buffer. Added 3 ul/well, spin 1000 rpm for 1 min and mixed on shaker for 30 sec, put on ice for 30 min. Stop stimulation after 30 minutes with 70 uL of prewarmed 1x fix/lysis buffer and use Feliex mate to resuspend (15 times, change tips for each plate) and incubate at 37 C for 10 minutes.

Centrifuge at 2000 rpm for 5 minutes aspirate with HCS plate washer, mix on shaker for 30 sec and then wash with 70 uL in dPBS and pelleted 2xs (2000 rpm for 5 min) and 50 ul wash in FACS buffer pelleted 1xs (2000 rpm for 5 min). Mix on shaker for 30 sec. For Intracellular markers staining (MX-1): Add 50 ul of BD Perm buffer III and mix on shaker for 30 sec. Incubate on ice for 30 minutes (in the dark). Wash with 50 uL of FACS buffer 2x (spin @2300 rpmx5 min after perm) followed by mixing on shaker for 30 sec. Resuspended in 20 ul of FACS buffer containing MX1 antibody ( )(4812)-Alexa 647: Novus Biologicals #NBP2-43704AF647) 20 ul FACS bf+0.8 ul hIgG+0.04 ul MX-1. Spin 1000 rpm for 1 min, mix on shaker for 30 se and the samples were incubated at RT in the dark for 45 minutes followed by washing 2×FACS buffer (spin @2300 rpm×5 min after perm). Resuspend 20 ul (35 uL total per well) of FACS buffer and cover with foil and place in 4° C. to read the following day. Plates were read on iQuePlus. The results were loaded into toolset and IC50 curves are generated in curve master. The y-axis 100% is set to 1 uM of resiquimod.

Induction of TNF-Alpha and Type I IFN Response Genes in Mouse Blood

The induction of TNF-alpha and Type I IFN response genes are downstream events that occur upon activation of the TLR7 pathway. The following is an assay that measures their induction in whole mouse blood in response to a TLR7 agonist.

Heparinized mouse whole blood was diluted with RPMI 1640 media with Pen-Strep in the ratio of 5:4 (50 uL whole blood and 40 uL of media). A volume of 90 uL of the diluted blood was transferred to wells of Falcon flat bottom 96-well tissue culture plates, and the plates were incubated at 4° C. for 1 h. Test compounds in 100% DMSO stocks were diluted 20-fold in the same media for concentration response assays, and then 10 uL of the diluted test compounds were added to the wells, so that the final DMSO concentration was 0.5%. Control wells received 10 uL media containing 5% DMSO. The plates were then incubated at 37° C. in a 5% $CO_2$ incubator for 17 h. Following the incubation, 100 uL of the culture medium as added to each well. The plates were centrifuged and 130 uL of supernatant was removed for use in assays of TNFa production by ELISA (Invitrogen, Catalog Number 88-7324 by Thermo-Fisher Scientific). A 70 uL volume of mRNA catcher lysis buffer (1×) with DTT from the Invitrogen mRNA Catcher Plus kit (Cat #K1570-02) was added to the remaining 70 uL sample in the well, and was mixed by pipetting up and down 5 times. The plate was then shaken at room temperature for 5-10 min, followed by addition of 2 uL of proteinase K (20 mg/mL) to each well. Plates were then shaken for 15-20 min at RT. The plates were then stored at −80° C. until further processing.

The frozen samples were thawed and mRNA was extracted using the Invitrogen mRNA Catcher Plus kit (Cat #K1570-02) according to the manufacturer's instructions. Half yield of mRNA from RNA extraction were used to synthesize cDNA in 20 μL reverse transcriptase reactions using Invitrogen SuperScript IV VILO Master Mix (Cat #11756500). TaqMan® real-time PCR was performed using QuantStudio Real-Time PCR system from ThermoFisher (Applied Biosystems). All real-time PCR reactions were run in duplicate using commercial predesigned TaqMan assays for mouse IFIT1, IFIT3, MX1 and PPIA gene expression and TaqMan Master Mix. PPIA was utilized as the housekeeping gene. The recommendations from the manufacturer were followed. All raw data (Ct) were normalized by average housekeeping gene (Ct) and then the comparative Ct (ΔΔCt) method were utilized to quantify relative gene expression (RQ) for experimental analysis.

DEFINITIONS

"Aliphatic" means a straight- or branched-chain, saturated or unsaturated, non-aromatic hydrocarbon moiety having the specified number of carbon atoms (e.g., as in "$C_3$ aliphatic," "$C_{1-5}$ aliphatic," "$C_1$-$C_5$ aliphatic," or "$C_1$ to $C_5$ aliphatic," the latter three phrases being synonymous for an aliphatic moiety having from 1 to 5 carbon atoms) or, where the number of carbon atoms is not explicitly specified, from 1 to 4 carbon atoms (2 to 4 carbons in the instance of unsaturated aliphatic moieties). A similar understanding is applied to the number of carbons in other types, as in $C_{2-4}$ alkene, $C_4$-$C_7$ cycloaliphatic, etc. In a similar vein, a term such as "$(CH_2)_{1-3}$" is to be understand as shorthand for the subscript being 1, 2, or 3, so that such term represents $CH_2$, $CH_2CH_2$, and $CH_2CH_2CH_2$.

"Alkyl" means a saturated aliphatic moiety, with the same convention for designating the number of carbon atoms being applicable. By way of illustration, $C_1$-$C_4$ alkyl moieties include, but are not limited to, methyl, ethyl, propyl, isopropyl, isobutyl, t-butyl, 1-butyl, 2-butyl, and the like. "Alkanediyl" (sometimes also referred to as "alkylene") means a divalent counterpart of an alkyl group, such as

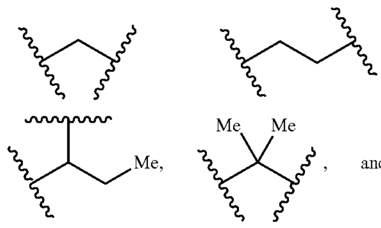

and

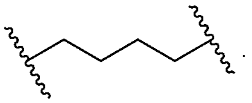

"Alkenyl" means an aliphatic moiety having at least one carbon-carbon double bond, with the same convention for designating the number of carbon atoms being applicable. By way of illustration, $C_2$-$C_4$ alkenyl moieties include, but are not limited to, ethenyl (vinyl), 2-propenyl (allyl or prop-2-enyl), cis-1-propenyl, trans-1-propenyl, E- (or Z—) 2-butenyl, 3-butenyl, 1,3-butadienyl (but-1,3-dienyl) and the like.

"Alkynyl" means an aliphatic moiety having at least one carbon-carbon triple bond, with the same convention for designating the number of carbon atoms being applicable. By way of illustration, $C_2$-$C_4$ alkynyl groups include ethynyl (acetylenyl), propargyl (prop-2-ynyl), 1-propynyl, but-2-ynyl, and the like.

"Cycloaliphatic" means a saturated or unsaturated, non-aromatic hydrocarbon moiety having from 1 to 3 rings, each ring having from 3 to 8 (preferably from 3 to 6) carbon atoms. "Cycloalkyl" means a cycloaliphatic moiety in which each ring is saturated. "Cycloalkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl. "Cycloalkanediyl" (sometimes also referred to as "cycloalkylene") means a divalent counterpart of a cycloalkyl group. Similarly, "bicycloalkanediyl" (osr "bicycloalkylene") and "spiroalkanediyl" (or "spiroalkylene") refer to divalent counterparts of a bicycloalkyl and spiroalkyl (or "spirocycloalkyl") group. By way of illustration, an example of a

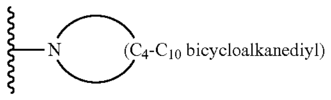 [SMILES: "(C4-C10 bicycloalkanediyl)" ; *N]

moiety is

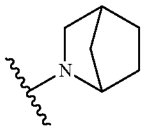 [SMILES: *N1CC2CCC1C2]

and an example of a

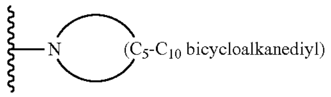

moiety is

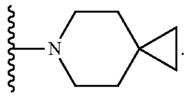 [SMILES: *N1CCC2(CC1)CC2]

"Heterocycloaliphatic" means a cycloaliphatic moiety wherein, in at least one ring thereof, up to three (preferably 1 to 2) carbons have been replaced with a heteroatom independently selected from N, O, or S, where the N and S optionally may be oxidized and the N optionally may be quaternized. Preferred cycloaliphatic moieties consist of one ring, 5- to 6-membered in size. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like. "Heterocycloalkylene" means a divalent counterpart of a heterocycloalkyl group.

"Alkoxy," "aryloxy," "alkylthio," and "arylthio" mean —O(alkyl), —O(aryl), —S(alkyl), and —S(aryl), respectively. Examples are methoxy, phenoxy, methylthio, and phenylthio, respectively.

"Halogen" or "halo" means fluorine, chlorine, bromine or iodine, unless a narrower meaning is indicated.

"Aryl" means a hydrocarbon moiety having a mono-, bi-, or tricyclic ring system (preferably monocyclic) wherein each ring has from 3 to 7 carbon atoms and at least one ring is aromatic. The rings in the ring system may be fused to each other (as in naphthyl) or bonded to each other (as in biphenyl) and may be fused or bonded to non-aromatic rings (as in indanyl or cyclohexylphenyl). By way of further illustration, aryl moieties include, but are not limited to, phenyl, naphthyl, tetrahydronaphthyl, indanyl, biphenyl, phenanthryl, anthracenyl, and acenaphthyl. "Arylene" means a divalent counterpart of an aryl group, for example 1,2-phenylene, 1,3-phenylene, or 1,4-phenylene.

"Heteroaryl" means a moiety having a mono-, bi-, or tricyclic ring system (preferably 5- to 7-membered monocyclic) wherein each ring has from 3 to 7 carbon atoms and at least one ring is an aromatic ring containing from 1 to 4 heteroatoms independently selected from from N, O, or S, where the N and S optionally may be oxidized and the N optionally may be quaternized. Such at least one heteroatom containing aromatic ring may be fused to other types of rings (as in benzofuranyl or tetrahydroisoquinolyl) or directly bonded to other types of rings (as in phenylpyridyl or 2-cyclopentylpyridyl). By way of further illustration, heteroaryl moieties include pyrrolyl, furanyl, thiophenyl (thienyl), imidazolyl, pyrazolyl, oxazolyl, isoxazolyl, thiazolyl, isothiazolyl, triazolyl, tetrazolyl, pyridyl, N-oxopyridyl, pyridazinyl, pyrimidinyl, pyrazinyl, quinolinyl, isoquinolynyl, quinazolinyl, cinnolinyl, quinozalinyl, naphthyridinyl, benzofuranyl, indolyl, benzothiophenyl, oxadiazolyl, thiadiazolyl, phenothiazolyl, benzimidazolyl, benzotriazolyl, dibenzofuranyl, carbazolyl, dibenzothiophenyl, acridinyl, and the like. "Heteroarylene" means a divalent counterpart of a heteroaryl group.

Where it is indicated that a moiety may be substituted, such as by use of "unsubstituted or substituted" or "optionally substituted" phrasing as in "unsubstituted or substituted $C_1$-$C_5$ alkyl" or "optionally substituted heteroaryl," such moiety may have one or more independently selected substituents, preferably one to five in number, more preferably one or two in number. Substituents and substitution patterns can be selected by one of ordinary skill in the art, having regard for the moiety to which the substituent is attached, to provide compounds that are chemically stable and that can be synthesized by techniques known in the art as well as the methods set forth herein. Where a moiety is identified as being "unsubstituted or substituted" or "optionally substituted," in a preferred embodiment such moiety is unsubstituted.

"Arylalkyl," (heterocycloaliphatic)alkyl," "arylalkenyl," "arylalkynyl," "biarylalkyl," and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl," "alkenylcycloalkyl," and the like mean an aryl, cycloalkyl, etc., moiety, as the case may be, substituted with an alkyl, alkenyl, etc., moiety, as the case may be, for example as in methylphenyl (tolyl) or allylcyclohexyl. "Hydroxyalkyl," "haloalkyl," "alkylaryl," "cyanoaryl," and the like mean an alkyl, aryl, etc., moiety, as the case may be, substituted with one or more of the identified substituent (hydroxyl, halo, etc., as the case may be).

For example, permissible substituents include, but are not limited to, alkyl (especially methyl or ethyl), alkenyl (especially allyl), alkynyl, aryl, heteroaryl, cycloaliphatic, heterocycloaliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O(haloalkyl) (especially —$OCF_3$), —O(cycloalkyl), —O(heterocycloalkyl), —O(aryl), alkylthio, arylthio, =O, =NH, =N(alkyl), =NOH, =NO(alkyl), —C(=O)(alkyl), —C(=O)H, —$CO_2$H, —C(=O)NHOH, —C(=O)O(alkyl), —C(=O)O(hydroxyalkyl), —C(=O)$NH_2$, —C(=O)NH(alkyl), —C(=O)N$(alkyl)_2$, —OC(=O)(alkyl), —OC(=O)(hydroxyalkyl), —OC(=O)O(alkyl), —OC(=O)O(hydroxyalkyl), —OC(=O)$NH_2$, —OC(=O)NH(alkyl), —OC(═O)N(alkyl)$_2$, azido, —$NH_2$, —NH(alkyl), —N(alkyl)$_2$, —NH(aryl), —NH(hydroxyalkyl), —NHC(═O)(alkyl), —NHC(═O)H, —NHC(═O)$NH_2$, —NHC(═O)NH(alkyl), —NHC(═O)N(alkyl)$_2$, —NHC(═NH)$NH_2$, —$OSO_2$(alkyl), —SH, —S(alkyl), —S(aryl), —S(cycloalkyl), —S(═O)alkyl, —$SO_2$(alkyl), —$SO_2NH_2$, —$SO_2$NH(alkyl), —$SO_2$N(alkyl)$_2$, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, ═O, ═NH, ═N(alkyl), ═NOH, ═NO(alkyl), —$CO_2H$, —C(═O)NHOH, —C(═O)O(alkyl), —C(═O)O(hydroxyalkyl), —C(═O)$NH_2$, —C(═O)NH(alkyl), —C(═O)N(alkyl)$_2$, —OC(═O)(alkyl), —OC(═O)(hydroxyalkyl), —OC(═O)O(alkyl), —OC(═O)O(hydroxyalkyl), —OC(═O)$NH_2$, —OC(═O)NH(alkyl), —OC(═O)N(alkyl)$_2$, azido, —$NH_2$, —NH(alkyl), —N(alkyl)$_2$, —NH(aryl), —NH(hydroxyalkyl), —NHC(═O)(alkyl), —NHC(═O)H, —NHC(═O)$NH_2$, —NHC(═O)NH(alkyl), —NHC(═O)N(alkyl)$_2$, —NHC(═NH)$NH_2$, —$OSO_2$(alkyl), —SH, —S(alkyl), —S(aryl), —S(═O)alkyl, —S(cycloalkyl), —$SO_2$(alkyl), —$SO_2NH_2$, —$SO_2$NH(alkyl), and —$SO_2$N(alkyl)$_2$. More preferred substituents are halo, hydroxyl, cyano, nitro, alkoxy, —O(aryl), ═O, ═NOH, ═NO(alkyl), —OC(═O)(alkyl), —OC(═O)O(alkyl), —OC(═O)$NH_2$, —OC(═O)NH(alkyl), —OC(═O)N(alkyl)$_2$, azido, —$NH_2$, —NH(alkyl), —N(alkyl)$_2$, —NH(aryl), —NHC(═O)(alkyl), —NHC(═O)H, —NHC(═O)$NH_2$, —NHC(═O)NH(alkyl), —NHC(═O)N(alkyl)$_2$, and —NHC(═NH)$NH_2$. Especially preferred are phenyl, cyano, halo, hydroxyl, nitro, $C_1$-$C_4$ alkyoxy, O($C_2$-$C_4$ alkanediyl)OH, and O($C_2$-$C_4$ alkanediyl)halo.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O(hydroxyalkyl), —O(haloalkyl), —O(aryl), —O(cycloalkyl), —O(heterocycloalkyl), alkylthio, arylthio, —C(═O)(alkyl), —C(═O)H, —$CO_2H$, —C(═O)NHOH, —C(═O)O(alkyl), —C(═O)O(hydroxyalkyl), —C(═O)$NH_2$, —C(═O)NH(alkyl), —C(═O)N(alkyl)$_2$, —OC(═O)(alkyl), —OC(═O)(hydroxyalkyl), —OC(═O)O(alkyl), —OC(═O)O(hydroxyalkyl), —OC(═O)$NH_2$, —OC(═O)NH(alkyl), —OC(═O)N(alkyl)$_2$, azido, —$NH_2$, —NH(alkyl), —N(alkyl)$_2$, —NH(aryl), —NH(hydroxyalkyl), —NHC(═O)(alkyl), —NHC(═O)H, —NHC(═O)$NH_2$, —NHC(═O)NH(alkyl), —NHC(═O)N(alkyl)$_2$, —NHC(═NH)$NH_2$, —$OSO_2$(alkyl), —SH, —S(alkyl), —S(aryl), —S(cycloalkyl), —S(═O)alkyl, —$SO_2$(alkyl), —$SO_2NH_2$, —$SO_2$NH(alkyl), and —$SO_2$N(alkyl)$_2$. More preferred substituents are alkyl, alkenyl, halo, haloalkyl, hydroxyl, hydroxyalkyl, cyano, nitro, alkoxy, —O(hydroxyalkyl), —C(═O)(alkyl), —C(═O)H, —$CO_2H$, —C(═O)NHOH, —C(═O)O(alkyl), —C(═O)O(hydroxyalkyl), —C(═O)$NH_2$, —C(═O)NH(alkyl), —C(═O)N(alkyl)$_2$, —OC(═O)(alkyl), —OC(═O)(hydroxyalkyl), —OC(═O)O(alkyl), —OC(═O)O(hydroxyalkyl), —OC(═O)$NH_2$, —OC(═O)NH(alkyl), —OC(═O)N(alkyl)$_2$, —$NH_2$, —NH(alkyl), —N(alkyl)$_2$, —NH(aryl), —NHC(═O)(alkyl), —NHC(═O)H, —NHC(═O)$NH_2$, —NHC(═O)NH(alkyl), —NHC(═O)N(alkyl)$_2$, and —NHC(═NH)$NH_2$. Especially preferred are $C_1$-$C_4$ alkyl, cyano, nitro, halo, and $C_1$-$C_4$alkoxy.

Where a range is stated, as in "$C_1$-$C_5$ alkyl" or "5 to 10%," such range includes the end points of the range, as in $C_1$ and $C_5$ in the first instance and 5% and 10% in the second instance.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature or symbols), all stereoisomers are included within the scope of the invention, as pure compounds as well as mixtures thereof. Unless otherwise indicated, racemates, individual enantiomers (whether optically pure or partially resolved), diastereomers, geometrical isomers, and combinations and mixtures thereof are all encompassed by this invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Pharmaceutically acceptable ester" means an ester that hydrolyzes in vivo (for example in the human body) to produce the parent compound or a salt thereof or has per se activity similar to that of the parent compound. Suitable esters include $C_1$-$C_5$ alkyl, $C_2$-$C_5$ alkenyl or $C_2$-$C_5$ alkynyl esters, especially methyl, ethyl or n-propyl.

"Pharmaceutically acceptable salt" means a salt of a compound suitable for pharmaceutical formulation. Where a compound has one or more basic groups, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic groups, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenylcyclohexylamine salt, benzathine salt, sodium salt, tetramethylammonium salt, and the like. Polymorphic crystalline forms and solvates are also encompassed within the scope of this invention.

"Subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. The "treatment of cancer", refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

In the formulae of this specification, a wavy line ( ) transverse to a bond or an asterisk (*) at the end of the bond denotes a covalent attachment site. For instance, a statement that R is

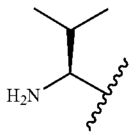

or that R is

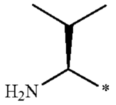 [SMILES: *[C@@H](N)C(C)C]

in the formula

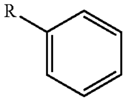

means

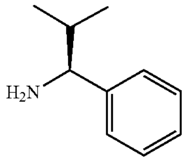

In the formulae of this specification, a bond traversing an aromatic ring between two carbons thereof means that the group attached to the bond may be located at any of the positions of the aromatic ring made available by removal of the hydrogen that is implicitly there (or explicitly there, if written out). By way of illustration:

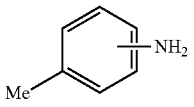

represents

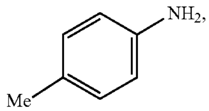

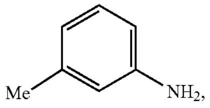

or

-continued

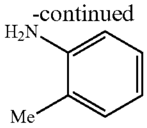

;

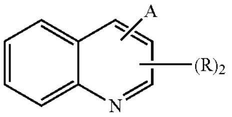

represents

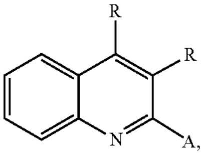

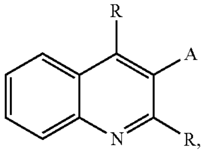

or

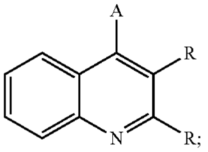

and

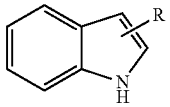

represents

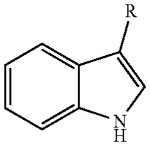

,

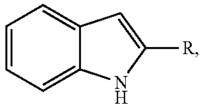

or

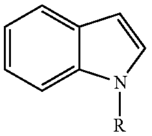

.

This disclosure includes all isotopes of atoms occurring in the compounds described herein. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. By way of example, a $C_1$-$C_3$ alkyl group can be undeuterated, partially deuterated, or fully deuterated and "$CH_3$" includes $CH_3$, $^{13}CH_3$, $^{14}CH_3$, $CH_2T$, $CH_2D$, $CHD_2$, $CD_3$, etc. In one embodiment, the various elements in a compound are present in their natural isotopic abundance.

Those skilled in the art will appreciate that certain structures can be drawn in one tautomeric form or another—for example, keto versus enol—and that the two forms are equivalent.

Acronyms and Abbreviations

Table C provides a list of acronyms and abbreviations used in this specification, along with their meanings.

TABLE C

| ACRONYM OR ABBREVIATION | MEANING OR DEFINITION |
|---|---|
| AIBN | Azobisisobutyronitrile |
| Alloc | Allyloxycarbonyl |
| Aq. | Aqueous |
| ACN | Acenonitrile |
| Boc | t-Butyloxycarbonyl |
| BOP | (Benzotriazol-1-yloxy)tris(dimethylamino)-phosphonium hexafluorophosphate (V) |
| BOP | (Benzotriazol-1-yloxy)tris(dimethylamino)-phosphonium hexafluorophosphate (V) |
| DBU | 1,8-Diazabicyclo[5.4.0]undec-7-ene |
| DCM | Dichloromethane |
| DIAD | Diisopropyl azodicarboxylate |
| DIPEA, DIEA | N,N-diisopropylethylamine, also known as Hünig's base |
| DMA | N,N-Dimethylacetamide |
| DMAP | 4-(Dimethylamino)pyridine |
| DMF | N,N-dimethylformamide |
| DMSO | Dimethyl sulfoxide |
| DTDP | 2,2'-dithiodipyridine |
| DTPA | Diethylenetriaminepentaacetic acid |
| EEDQ | Ethyl 2-ethoxyquinoline-1(2H)-carboxylate |
| Fmoc | Fluorenylmethyloxycarbonyl |
| HATU | Hexafluorophosphate Azabenzotriazole Tetramethyl Uronium; 1-[Bis(dimethylamino)-methylene]-1H-1,2,3-triazolo[4,5-b]pyridinium 3-oxide hexafluorophosphate |
| HEPES | 4-(2-Hydroxyethyl)piperazine-1-ethanesulfonic acid, N-(2-Hydroxyethyl)piperazine-N'-(2-ethanesulfonic acid) |
| HPLC | High pressure liquid chromatography |
| Hunig's base | See DIPEA, DIEA |
| LCMS, LC-MS, LC/MS | Liquid chromatography-mass spectrometry |
| mCPBA | m-chloroperbenzoic acid |
| MS | Mass spectrometry |
| MsCl | Methanesylfonyl chloride, mesyl chloride |
| NBS, NCS, NIS | N-Bromosuccinimide, N-chlorosuccinimide, and N-iodosuccinimide, respectively |
| NMR | Nuclear magnetic resonance |
| PEG | Poly(ethylene glycol) |
| PTFE | Poly(tetrafluoroethylene) |
| RT (in context of liquid chromatography) | Retention time, in min |
| RT (in the context of reaction conditions) | Room (ambient) temperature, circa 25° C. |
| Sat. | Saturated |
| Soln | Solution |
| TBDPS | tert-Butyldiphenylsilyl |
| TBS | t-Butyldimethylsilyl group |
| TEA | Triethylamine |
| TEAA | Triethylammonium acetate |
| TFA | Trifluoroacetic acid |
| THF | Tetrahydrofuran |

REFERENCES

Full citations for the following references cited in abbreviated fashion by first author (or inventor) and date earlier in this specification are provided below. Each of these references is incorporated herein by reference for all purposes.

Akinbobuyi et al., *Tetrahedron Lett.* 2015, 56, 458, "Facile syntheses of functionalized toll-like receptor 7 agonists".

Akinbobuyi et al., *Bioorg. Med. Chem. Lett.* 2016, 26, 4246, "Synthesis and immunostimulatory activity of substituted TLR7 agonists."

Barberis et al., US 2012/0003298 A1 (2012).

Beesu et al., *J. Med. Chem.* 2017, 60, 2084, "Identification of High-Potency Human TLR8 and Dual TLR7/TLR8 Agonists in Pyrimidine-2,4-diamines."

Berghöfer et al., *J. Immunol.* 2007, 178, 4072, "Natural and Synthetic TLR7 Ligands Inhibit CpG-A- and CpG-C-Oligodeoxynucleotide-Induced IFN-α Production."

Bonfanti et al., US 2014/0323441 A1 (2015) [2015a].

Bonfanti et al., US 2015/0299221 A1 (2015) [2015b].

Bonfanti et al., US 2016/0304531 A1 (2016).
Carson et al., US 2013/0202629 A1 (2013).
Carson et al., U.S. Pat. No. 8,729,088 B2 (2014).
Carson et al., U.S. Pat. No. 9,050,376 B2 (2015).
Carson et al., US 2016/0199499 A1 (2016).
Chan et al., *Bioconjugate Chem.* 2009, 20, 1194, "Synthesis and Immunological Characterization of Toll-Like Receptor 7 Agonistic Conjugates."
Chan et al., *Bioconjugate Chem.* 2011, 22, 445, "Synthesis and Characterization of PEGylated Toll Like Receptor 7 Ligands."
Chen et al., U.S. Pat. No. 7,919,498 B2 (2011).
Coe et al., U.S. Pat. No. 9,662,336 B2 (2017).
Cortez and Va, *Medicinal Chem. Rev.* 2018, 53, 481, "Recent Advances in Small-Molecule TLR7 Agonists for Drug Discovery".
Cortez et al., US 2017/0121421 A1 (2017).
Cortez et al., U.S. Pat. No. 9,944,649 B2 (2018).
Dellaria et al., WO 2007/028129 A1 (2007).
Desai et al., U.S. Pat. No. 9,127,006 B2 (2015).
Ding et al., WO 2016/107536 A1 (2016).
Ding et al., US 2017/0273983 A1 (2017) [2017a].
Ding et al., WO 2017/076346 A1 (2017) [2017b].
Gadd et al., *Bioconjugate Chem.* 2015, 26, 1743, "Targeted Activation of Toll-Like Receptors: Conjugation of a Toll-Like Receptor 7 Agonist to a Monoclonal Antibody Maintains Antigen Binding and Specificity."
Graupe et al., U.S. Pat. No. 8,993,755 B2 (2015).
Embrechts et al., *J. Med. Chem.* 2018, 61, 6236, "2,4-Diaminoquinazolines as Dual Toll Like Receptor (TLR) 7/8 Modulators for the Treatment of Hepatitis B Virus."
Halcomb et al., U.S. Pat. No. 9,161,934 B2 (2015).
Hashimoto et al., US 2009/0118263 A1 (2009).
He et al., U.S. Pat. No. 10,487,084 B2 (2019) [2019a].
He et al., U.S. Pat. No. 10,508,115 B2 (2019) [2019b].
Hirota et al., U.S. Pat. No. 6,028,076 (2000).
Holldack et al., US 2012/0083473 A1 (2012).
Isobe et al., U.S. Pat. No. 6,376,501 B1 (2002).
Isobe et al., JP 2004137157 (2004).
Isobe et al., *J. Med. Chem.* 2006, 49 (6), 2088, "Synthesis and Biological Evaluation of Novel 9-Substituted-8-Hydroxyadenine Derivatives as Potent Interferon Inducers."
Isobe et al., U.S. Pat. No. 7,521,454 B2 (2009) [2009a].
Isobe et al., US 2009/0105212 A1 (2009) [2009b].
Isobe et al., US 2011/0028715 A1 (2011).
Isobe et al., U.S. Pat. No. 8,148,371 B2 (2012).
Jensen et al., WO 2015/036044 A1 (2015).
Jones et al., U.S. Pat. No. 7,691,877 B2 (2010).
Jones et al., US 2012/0302598 A1 (2012).
Kasibhatla et al., U.S. Pat. No. 7,241,890 B2 (2007).
Koga-Yamakawa et al., *Int. J. Cancer* 2013, 132 (3), 580, "Intratracheal and oral administration of SM-276001: A selective TLR7 agonist, leads to antitumor efficacy in primary and metastatic models of cancer."
Li et al., U.S. Pat. No. 9,902,730 B2 (2018).
Lioux et al., U.S. Pat. No. 9,295,732 B2 (2016).
Lund et al., *Proc. Nat'l Acad. Sci* (*USA*) 2004, 101 (15), 5598, "Recognition of single-stranded RNA viruses by Toll-like receptor 7."
Maj et al., U.S. Pat. No. 9,173,935 B2 (2015).
McGowan et al., US 2016/0168150 A1 (2016) [2016a].
McGowan et al., U.S. Pat. No. 9,499,549 B2 (2016) [2016b].
McGowan et al., *J. Med. Chem.* 2017, 60, 6137, "Identification and Optimization of Pyrrolo[3,2-d]pyrimidine Toll-like Receptor 7 (TLR7) Selective Agonists for the Treatment of Hepatitis B."
Musmuca et al., *J. Chem. Information & Modeling* 2009, 49 (7), 1777, "Small-Molecule Interferon Inducers. Toward the Comprehension of the Molecular Determinants through Ligand-Based Approaches."
Nakamura et al., *Bioorg. Med. Chem. Lett.* 2013, 13, 669, "Synthesis and evaluation of 8-oxoadenine derivatives as potent Toll-like receptor agonists with high water solubility."
Ogita et al., US 2007/0225303 A1 (2007).
Ota et al., WO 2019/124500 A1 (2019).
Pilatte et al., WO 2017/216293 A1 (2017).
Poudel et al., U.S. Pat. No. 10,472,361 B2 (2019) [2019a].
Poudel et al., U.S. Pat. No. 10,494,370 B2 (2019) [2019b].
Poudel et al., US 2020/0038403 A1 (2020) [2020a].
Poudel et al., US 2020/0039986 A1 (2020) [2020b].
Purandare et al., WO 2019/209811 A1 (2019).
Pryde, U.S. Pat. No. 7,642,350 B2 (2010).
Sato-Kaneko et al., *JCI Insight* 2017, 2, e93397, "Combination Immunotherapy with TLR Agonists and Checkpoint Inhibitors Suppresses Head and Neck Cancer".
Smits et al., *The Oncologist* 2008, 13, 859, "The Use of TLR7 and TLR8 Ligands for the Enhancement of Cancer Immunotherapy".
Vasilakos and Tomai, *Expert Rev. Vaccines* 2013, 12, 809, "The Use of Toll-like Receptor 7/8 Agonists as Vaccine Adjuvants".
Vernejoul et al., US 2014/0141033 A1 (2014).
Young et al., U.S. Pat. No. 10,457,681 B2 (2019).
Yu et al., *PLoS One* 2013, 8 (3), e56514, "Toll-Like Receptor 7 Agonists: Chemical Feature Based Pharmacophore Identification and Molecular Docking Studies."
Zhang et al., *Immunity* 2016, 45, 737, "Structural Analysis Reveals that Toll-like Receptor 7 Is a Dual Receptor for Guanosine and Single-Stranded RNA."
Zhang et al., WO 2018/095426 A1 (2018)>
Zurawski et al., US 2012/0231023 A1 (2012).

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various FIGURES and descriptions herein relate to specific embodiments of the invention, it is to be understood that where a specific feature is disclosed in the context of a particular FIGURE or embodiment, such feature can also be used, to the extent appropriate, in the context of another FIGURE or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

What is claimed is:

1. A compound having a structure according to formula I (I)

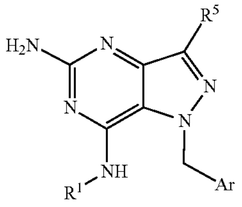

wherein

Ar is

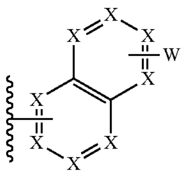

or

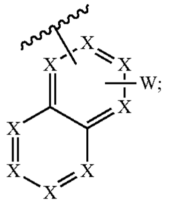

W is H, halo, $C_1$-$C_3$ alkyl, CN, ($C_1$-$C_4$ alkanediyl) OH,

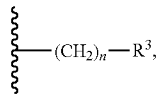

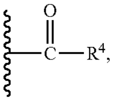

or

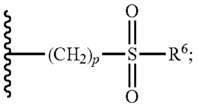

each X is independently N or $CR^2$;

$R^1$ is ($C_1$-$C_5$ alkyl),
($C_2$-$C_5$ alkenyl),
($C_1$-$C_8$ alkanediyl)$_{0-1}$ ($C_3$-$C_6$ cycloalkyl),
($C_1$-$C_8$ alkanediyl)$_{0-1}$ ($C_5$-$C_{10}$ spiroalkyl),
($C_2$-$C_8$ alkanediyl) OH,
($C_2$-$C_8$ alkanediyl)O($C_1$-$C_3$ alkyl),
($C_1$-$C_4$ alkanediyl)$_{0-1}$ (5-6 membered heteroaryl),
($C_1$-$C_4$ alkanediyl)$_{0-1}$phenyl,
($C_1$-$C_4$ alkanediyl) $CF_3$,
($C_2$-$C_8$ alkanediyl) N [C(=O)]($C_1$-$C_3$ alkyl),
or
($C_2$-$C_8$ alkanediyl) $NR^xR^y$;

each $R^2$ is independently H, O($C_1$-$C_3$ alkyl), S ($C_1$-$C_3$ alkyl), $SO_2$ ($C_1$-$C_3$ alkyl), $C_1$-$C_3$ alkyl, O($C_3$-$C_4$ cycloalkyl), S($C_3$-$C_4$ cycloalkyl), $SO_2$ ($C_3$-$C_4$ cycloalkyl), $C_3$-$C_4$ cycloalkyl, Cl, F, CN, or [C(=O)]$_{0-1}$ $NR^xR^y$;

$R^3$ is H, halo, OH, CN,
$NH_2$,
NH [C(=O)]$_{0-1}$ ($C_1$-$C_8$alkyl),
N($C_1$-$C_5$alkyl)$_2$,
NH [C(=O)]$_{0-1}$ ($C_1$-$C_4$ alkanediyl)$_{0-1}$ ($C_3$-$C_8$ cycloalkyl),
NH [C(=O)]$_{0-1}$ ($C_1$-$C_4$ alkanediyl)$_{0-1}$ ($C_4$-$C_{10}$ bicycloalkyl),
NH [C(=O)]$_{0-1}$ ($C_1$-$C_4$ alkanediyl)$_{0-1}$ ($C_5$-$C_{10}$ spiroalkyl),
N($C_3$-$C_6$ cycloalkyl)$_2$,
O($C_1$-$C_4$ alkanediyl)$_{0-1}$ ($C_3$-$C_8$ cycloalkyl),
O($C_1$-$C_4$ alkanediyl)$_{0-1}$ ($C_4$-$C_8$ bicycloalkyl),
O($C_1$-$C_4$ alkanediyl)$_{0-1}$ ($C_5$-$C_{10}$ spiroalkyl),
O($C_1$-$C_4$ alkanediyl)$_{0-1}$ ($C_1$-$C_6$ alkyl),
N [$C_1$-$C_3$ alkyl]C(=O) ($C_1$-$C_6$ alkyl),
NH($SO_2$) ($C_1$-$C_8$alkyl),
NH($SO_2$) ($C_1$-$C_4$ alkanediyl)$_{0-1}$ ($C_3$-$C_8$ cycloalkyl),
NH($SO_2$) ($C_1$-$C_4$ alkanediyl)$_{0-1}$ ($C_4$-$C_{10}$ bicycloalkyl),
NH($SO_2$) ($C_1$-$C_4$ alkanediyl)$_{0-1}$ ($C_5$-$C_{10}$ spiroalkyl),
a 6-membered aromatic or heteroaromatic moiety,
a 5-membered heteroaromatic moiety, or
a moiety having the structure

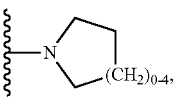

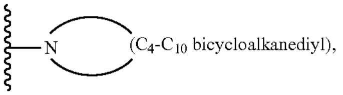

or

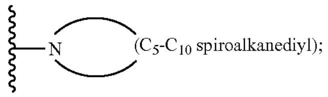

$R^4$ is $NH_2$,
NH($C_1$-$C_5$alkyl),
N($C_1$-$C_5$alkyl)$_2$,
NH($C_1$-$C_4$ alkanediyl)$_{0-1}$ ($C_3$-$C_8$ cycloalkyl),
NH($C_1$-$C_4$ alkanediyl)$_{0-1}$ ($C_4$-$C_{10}$ bicycloalkyl),
NH($C_1$-$C_4$ alkanediyl)$_{0-1}$ ($C_5$-$C_{10}$ spiroalkyl),
N($C_3$-$C_6$ cycloalkyl)$_2$,
or
a moiety having the structure

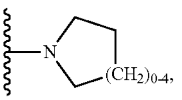

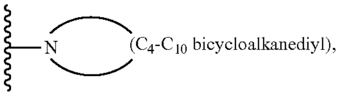

or

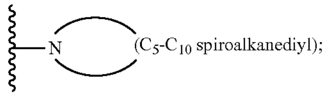

$R^5$ is H, $C_1$-$C_5$alkyl, $C_2$-$C_5$ alkenyl, $C_3$-$C_6$ cycloalkyl, halo, O($C_1$-$C_5$alkyl), ($C_1$-$C_4$ alkanediyl) OH, ($C_1$-$C_4$ alkanediyl)O($C_1$-$C_3$ alkyl), phenyl, NH($C_1$-$C_5$ alkyl), 5 or 6 membered heteroaryl,

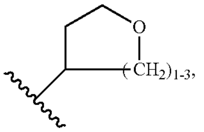

or

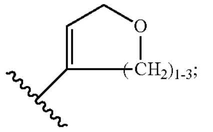

$R^6$ is $NH_2$, $(NH)_{0-1}$ ($C_1$-$C_5$alkyl), $N(C_1$-$C_5alkyl)_2$, $(NH)_{0-1}$ ($C_1$-$C_4$ alkanediyl)$_{0-1}$ ($C_3$-$C_8$ cycloalkyl), $(NH)_{0-1}$ ($C_1$-$C_4$ alkanediyl)$_{0-1}$ ($C_4$-$C_{10}$ bicycloalkyl), $(NH)_{0-1}$ ($C_1$-$C_4$ alkanediyl)$_{0-1}$ ($C_5$-$C_{10}$ spiroalkyl), $N(C_3$-$C_6$ cycloalkyl)$_2$, or a moiety having the structure

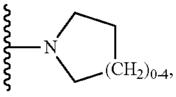

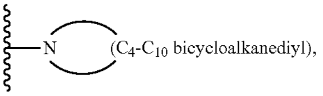

or

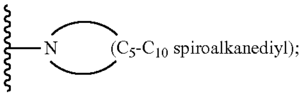

$R^x$ and $R^y$ are independently H or $C_1$-$C_3$ alkyl or $R^x$ and $R^y$ combine with the nitrogen to which they are bonded to form a 3- to 7-membered heterocycle;

n is 1, 2, or 3;

and p is 0, 1, 2, or 3;

wherein in $R^1$, $R^2$, $R^3$, $R^4$, $R^5$, and $R^6$ an alkyl, cycloalkyl, alkanediyl, bicycloalkyl, spiroalkyl, cyclic amine, 6-membered aromatic or heteroaromatic moiety, 5-membered heteroaromatic moiety or a moiety of the formula

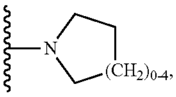

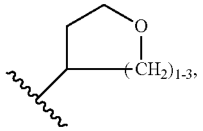

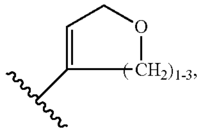

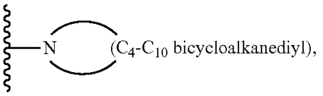

or

-continued

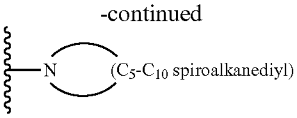

is optionally substituted with one or more substituents selected from OH, halo, CN, ($C_1$-$C_3$ alkyl), O($C_1$-$C_3$ alkyl), C(=O) ($C_1$-$C_3$ alkyl), $SO_2$ ($C_1$-$C_3$ alkyl), $NR^xR^y$, ($C_1$-$C_4$ alkanediyl) OH, ($C_1$-$C_4$ alkanediyl)O ($C_1$-$C_3$ alkyl);

and an alkyl, alkanediyl, cycloalkyl, bicycloalkyl, spiroalkyl, or a moiety of the formula

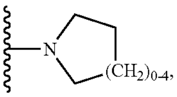

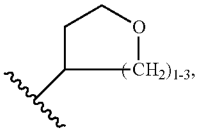

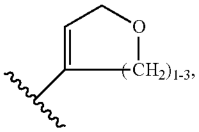

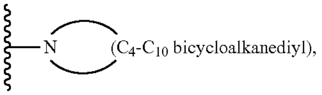

or

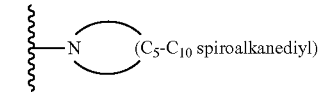

may have a $CH_2$ group replaced by O, $SO_2$, $CF_2$, C(=O), NH,

N [C(=O)]$_{0-1}$ ($C_1$-$C_3$ alkyl),

N [C(=O)]$_{0-1}$ ($C_1$-$C_4$ alkanediyl)$_{0-1}$$CF_3$, or

N [C(=O)]$_{0-1}$ ($C_1$-$C_4$ alkanediyl)$_{0-1}$ ($C_3$-$C_8$ cycloalkyl).

2. The compound according to claim 1, having a structure according to formula (Ia)

(Ia)

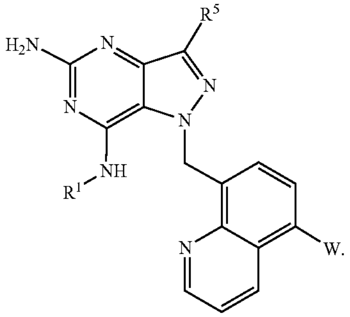

3. The compound according to claim 1, having a structure according to formula (Ib)

(Ib)
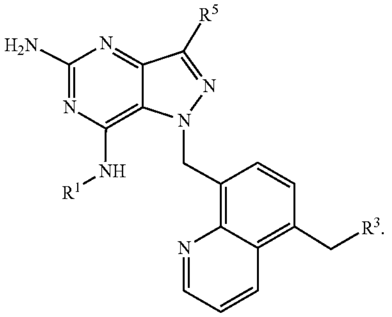
4. The compound according to claim 3, wherein $R^3$ is
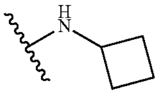,
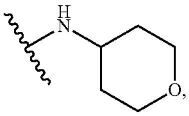,
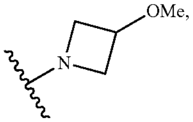,
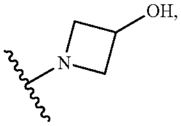,
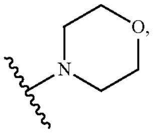, or
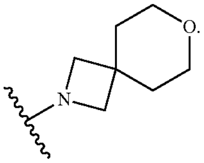.
5. The compound according to claim 4, wherein $R^1$ is
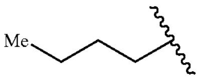,
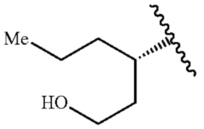,
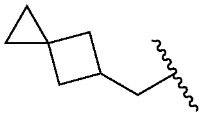, or
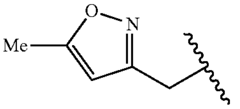;
and
$R^5$ is H or Me.
6. The compound according to claim 1, having a structure according to formula (Ic)
(Ic)
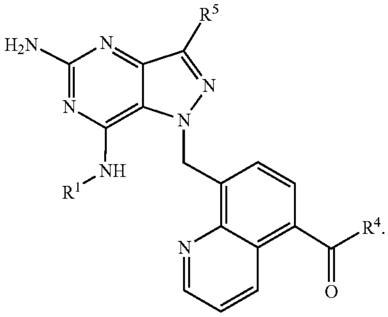
7. The compound according to claim 6, wherein $R^4$ is
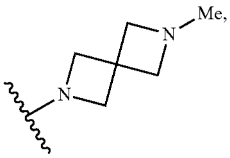,
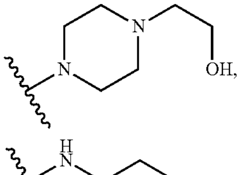,
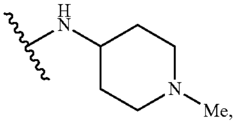, or
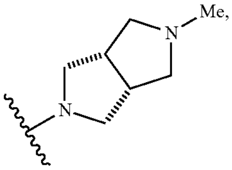
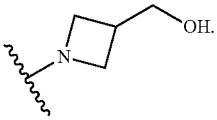.
8. The compound according to claim 7, wherein $R^1$ is
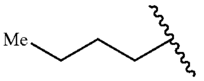,
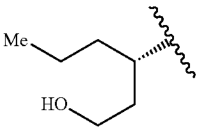,
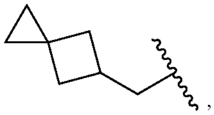, or -continued
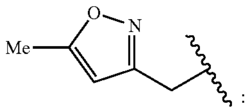
and
$R^5$ is H or Me.
9. A compound having a structure according to formula (Id)
(Id)
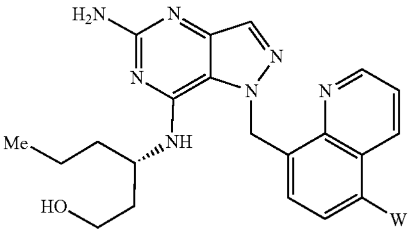
wherein W is
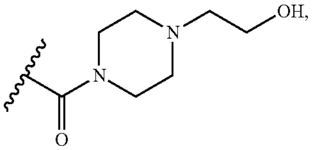
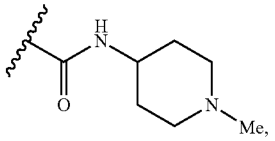
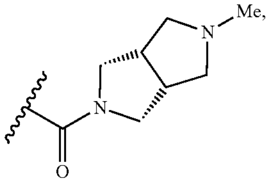
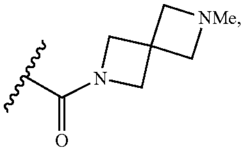
or
-continued
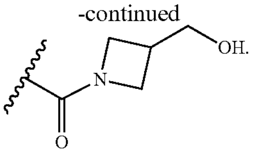
10. A compound having a structure according to formula (Ie)
(Ie)
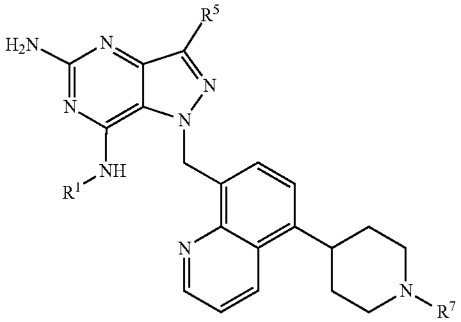
wherein
$R^1$ is
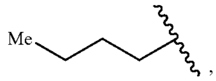
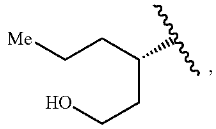
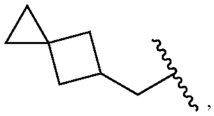
or
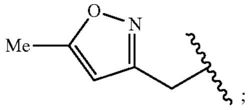
$R^5$ is H or Me; and
$R^7$ is H, $C_1$-$C_8$alkyl, or $C_3$-$C_6$ cycloalkyl; wherein the cycloalkyl group optionally has a $CH_2$ group replaced by O, NH, or N($C_1$-$C_3$)alkyl.
* * * * *